United States Patent
Voskoboynik et al.

(10) Patent No.: US 8,569,532 B2
(45) Date of Patent: Oct. 29, 2013

(54) CATALYSTS

(75) Inventors: Alexander Zelmanovich Voskoboynik, Moscow (RU); Andrei Fyodorovich Asachenko, Chelyabinsk (RU); Dmitry Konanovich, Moscow (RU); Mikhail V. Nikulin, Moscow (RU); Alexey Tzarev, Moscow (RU); Janne Maaranen, Tuusula (FI); Tiina Vanne, Vantaa (FI); Jyrki Kauhanen, Askola (FI); Erik Mansner, Espoo (FI); Esa Kokko, Vantaa (FI); Laura Saarinen, Hyvinkää (FI)

(73) Assignee: Borealis Technology Oy, Porvoo (FI)

( * ) Notice: Subject to any disclaimer, the term of this patent is extended or adjusted under 35 U.S.C. 154(b) by 0 days.

(21) Appl. No.: 13/493,080

(22) Filed: Jun. 11, 2012

(65) Prior Publication Data

US 2012/0252993 A1    Oct. 4, 2012

Related U.S. Application Data

(63) Continuation of application No. 12/675,545, filed as application No. PCT/EP2008/007007 on Aug. 27, 2008.

(30) Foreign Application Priority Data

Aug. 27, 2007 (EP) ..................... 07016767

(51) Int. Cl.
*C07F 17/00* (2006.01)
*B01J 31/22* (2006.01)
*C08F 4/6592* (2006.01)

(52) U.S. Cl.
USPC ............. 556/53; 502/103; 502/152; 526/160; 526/348; 526/943

(58) Field of Classification Search
USPC ............. 556/53; 502/103, 152; 526/160, 348, 526/943
See application file for complete search history.

(56) References Cited

U.S. PATENT DOCUMENTS

| | | | |
|---|---|---|---|
| 5,451,649 A | 9/1995 | Zenk et al. | |
| 6,984,703 B1 * | 1/2006 | Biagini et al. | 526/160 |
| 2006/0160967 A1 * | 7/2006 | Voskoboynikov et al. | 526/127 |

FOREIGN PATENT DOCUMENTS

| | | |
|---|---|---|
| EP | 0 672 675 | 9/1995 |
| WO | WO 96/38458 | 12/1996 |
| WO | WO 97/31035 | 8/1997 |
| WO | WO 01/40238 | 6/2001 |
| WO | WO 03/000744 | 1/2003 |
| WO | WO 2005/105864 | 11/2005 |
| WO | WO 2005/108435 | 11/2005 |
| WO | WO 2006/065809 | 6/2006 |
| WO | WO 2006/065843 | 6/2006 |
| WO | WO 2006/065844 | 6/2006 |
| WO | WO 2006/065906 | 6/2006 |

OTHER PUBLICATIONS

International Search Report for PCT/EP2008/007007 mailed May 19, 2009.
Written Opinion of the International Searching Authority for PCT/EP2008/007007 mailed May 19, 2009.
Resconi et al, "Selectivity in Propene Polymerization with Metallocene Catalysts", Chem. Rev. 2000, 100, 1253-1345.

* cited by examiner

*Primary Examiner* — Caixia Lu
(74) *Attorney, Agent, or Firm* — Nixon & Vanderhye P.C.

(57) ABSTRACT

A complex containing a ligand of formula (I):

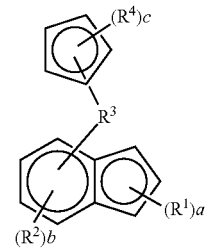

useful in the formation of olefin polymerization catalysts and their use in olefin polymerization.

15 Claims, No Drawings

CATALYSTS

This application is a continuation of U.S. application Ser. No. 12/675,545 filed May 12, 2010, pending, which in turn is the U.S. national phase of International Application No. PCT/EP2008/007007 filed 27 Aug. 2008 which designated the U.S. and claims priority to EP Application No. 07016767.1 filed 27 Aug. 2007, the entire contents of each of which are hereby incorporated by reference.

This invention relates to complexes of bridged asymmetric η-ligands useful in the formation of olefin polymerisation catalysts, as well as the catalysts themselves and the use therefore in olefin polymerisation. In particular, the invention relates to complexes which comprise asymmetric ligands which are bridged between the 4-7 position of an indenyl group and the 5-membered ring of a cyclopentadienyl containing ligand.

The use of metal complexes in the polymerisation of olefins is well known. Countless academic and patent publications describe the use of catalysts such as metallocenes in olefin polymerisation. Metallocenes are now used industrially and polyethylenes in particular are often produced using cyclopentadienyl based catalyst systems with all manner of different substitution patterns.

Most metallocene complexes however, are based on symmetrical Π-bonding ligands systems such as cyclopentadienyls and indenyls in conjunction with a variety of sigma ligands, typically chlorides, and are unbridged. Where bridges are used between ligands, these are typically formed from the 1-position of a to the 1-position of another cyclopentadienyl group. The art is replete with disclosures of such compounds. Moreover, bridged metallocenes tend to be symmetrical giving rise to meso/rac isomerism.

There remains however, a need to find new catalyst materials for olefin polymerisation as each new catalyst can impart different properties to the formed polymer and can exhibit potentially beneficial levels of activity. In particular, new catalysts can provide increased Mw and good comonomer incorporation and hydrogen response. This has special benefits for HDPE and MDPE.

The present inventors have found a new class of olefin polymerisation catalysts not previously described in the art. The complexes required to form the catalysts of the invention are, inter alia, asymmetric and bridged by a bridge linking the 4-7 position of a indenyl ring to a cyclopentadienyl ring.

Bridges from the 4-position of an indenyl ring are not new. WO96/38458 describes complexes bridged between the 4-position of two indenyl ligands.

Asymmetric bridged metallocenes are not new either. WO01/40238 describes a metallocene in which an indenyl group is connected by a methylene bridge via its 4-position to a cyclopentadienyl moiety. WO2006/065906 describes bridged indenyl ligand systems in which halogen substituents are present. WO2006/065809 and WO2005108435 describe indenyl ligands bridged using group 15 and 16 atoms such as phosphorus and WO2005/105864 describes bridged indenyl ligand systems in which aromatic heterocycles are bound to the indenyl ring system.

The present inventors have found that bridged indenyl complexes where the bridge is carbon or silicon based and links the 4-7 position of an indenyl group to the five membered ring of a cyclopentadienyl containing ligand are very valuable in that they provide polymers of high Mw and high productivity. Normally, high molecular weight polymers are formed in processes where catalyst activity is reduced but the present catalysts have been found to produce high Mw polymers without a significant reduction in productivity.

Thus, viewed from one aspect the invention provides a complex comprising a ligand of formula (I):

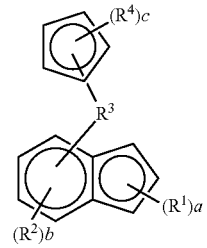

wherein each $R^1$, which may be the same or different, is hydrogen, an optionally substituted $C_{1-20}$ hydrocarbyl group, $N(R^5)_2$, silyl, siloxy; an optionally substituted heteroaryl group, an optionally substituted heterocyclyl group or two $R^1$ groups on adjacent carbon atoms taken together may form an optionally substituted 5- to 8-membered fused ring;

each $R^2$, which may be the same or different is hydrogen, is hydrogen, an optionally substituted $C_{1-20}$ hydrocarbyl group, $N(R^5)_2$, silyl, siloxy; an optionally substituted heteroaryl group, or an optionally substituted heterocyclyl group;

$R^3$, which binds to the 6-membered ring of the indenyl group, is $-(Si(R^5)_2)_p-$, where p is 1 or 2, $-(C(R_5)_2)n-$ where n is an integer of 2 or more;

each $R^4$ which may be the same or different, is hydrogen, an optionally substituted $C_{1-20}$ hydrocarbyl group, $N(R^5)_2$, silyl, siloxy, an optionally substituted heteroaryl group, an optionally substituted heterocyclyl group or two $R^4$ groups on adjacent carbon atoms taken together can form an optionally substituted 5- to 8-membered fused carbon ring;

each $R^5$, which may be the same or different, is hydrogen, an optionally substituted $C_{1-20}$ hydrocarbyl group, or two $R^5$ groups taken together can form an optionally substituted 5- to 8-membered ring;

a is 0 to 3;

b is 0 to 3 c is 0 to 4;

complexed to a metal ion, M.

Viewed from another aspect the invention provides a complex comprising formula (II)

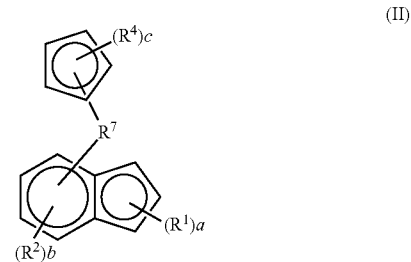

wherein $R^1$, $R^2$, $R^4$, $R^5$, a, b and c are as hereinbefore defined and $R^7$ is $-C(R^5)_2-$;

complexed to a metal ion, M;

with the proviso that $R^7$ binds to the 5 or 6 position of the indenyl ring.

Viewed from another aspect the invention provides an olefin polymerisation catalyst comprising:

(i) a complex comprising a metal ion coordinated by at least one ligand of formula (I) or (II); and (ii) a cocatalyst.

Viewed from another aspect the invention provides use in olefin polymerisation of a catalyst as hereinbefore defined.

Viewed from another aspect the invention provides a process for the polymerisation of at least one olefin comprising reacting said at least one olefin with a catalyst as hereinbefore described.

The compounds required to form the complexes of the invention are also new and form a further aspect of the invention. Viewed from another aspect therefore the invention provides a compound of formula (III) or (IV)

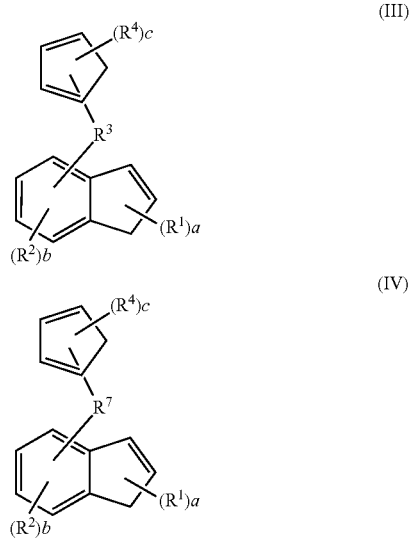

wherein $R^1$, $R^2$, $R^3$, $R^4$, $R^5$, $R^7$, a, b and c are as hereinbefore defined.

Throughout the description the following definitions are employed.

The term $C_{1-20}$ hydrocarbyl group, as used herein, covers any $C_{1-20}$ group comprising carbon and hydrogen only and therefore includes $C_{1-20}$ alkyl, $C_{2-20}$ alkenyl, $C_{2-20}$ alkynyl, $C_{3-20}$ cycloalkyl, $C_{3-20}$ cycloalkenyl, $C_{6-20}$ aryl groups, $C_{7-20}$ alkylaryl groups or $C_{7-20}$ arylalkyl groups. Unless otherwise stated, preferred $C_{1-20}$ hydrocarbyl groups are $C_{1-20}$ alkyl groups or $C_{6-20}$ aryl groups, especially $C_{1-8}$ alkyl groups or $C_{6-10}$ aryl groups. Most especially preferred hydrocarbyl groups are methyl, ethyl, propyl, isopropyl, tertbutyl, phenyl or benzyl.

The term halo includes fluoro, chloro, bromo and iodo groups, especially chloro groups.

The term silyl means a group of formula $(R^5)_3Si$— where $R^5$ has the meaning as hereinbefore defined. Highly preferred silyl groups are those of formula $(C_{1-6}\ alkyl)_3Si$—, especially trimethylsilyl or tertbutyldimethylsiloxy.

The term siloxy means a group of formula $(R^5)_3SiO$— where $R^5$ has the meaning as hereinbefore defined. Highly preferred siloxy groups are those of formula $(C_{1-6}\ alkyl)_3SiO$—, especially trimethylsiloxy or tertbutyldimethylsiloxy.

The term heteroaryl means a monocyclic or multicyclic aromatic ring structure comprising at least one heteroatom. Preferred heteroaryl groups have up to 20 carbon atoms, preferably up to 10 carbon atoms. Preferred heteroaryl groups have 1 to 4 heteroatoms selected from O, S and N, especially O and N. Preferred heteroaryl groups include pyridyl, pyrrolyl, furyl, indolyl, indolizinyl, benzofuranyl or benzothienyl groups.

The term heterocyclyl means a monocyclic or polycyclic (non aromatic) ring structure comprising at least one heteroatom. Preferred heterocyclic groups have up to 20 carbon atoms, preferably up to 10 carbon atoms. Preferred heterocyclic groups have 1 to 3 heteroatoms selected from O, S, and N, especially O and N. Preferred heterocyclic groups include piperidinyl, furanyl, piperazinyl diazines, oxazolinyl, or thionyl.

The term optionally substituted is used herein to allow for the presence of one or more additional substituents on a group. Said optional substituents are selected from the group consisting of $C_{1-20}$ hydrocarbyl, $C_{1-20}$ alkylhalide, $C_{1-20}$ alkylhydroxy, —$N(R^5)_2$, silyl, siloxy, hydroxyl, —$OCOC_{1-20}$ alkyl, —$NO_2$, —$CF_3$, —SH, —$C(=O)R^5$, —$C(=O)OR^5$, —$C(=O)NR^5R^5$, —$SR^5$, —$NR^5C(=O)R^5$, —$OC(=O)R^5$, —$OR^5$, heteroaryl, and heterocyclyl.

Preferred optional substituents are $C_{1-6}$ alkyl, phenyl, $NH_2$, $NMe_2$, and trimethysilyl.

It will be appreciated that the number of optional substituents present can vary depending on the nature of the moiety carrying the optional substituents. Preferably however, 1 to 3 such optional substituents will be present, especially 1. Any optionally substituted moiety can, of course, remain unsubstituted.

The metal ion M can be any metal ion from the periodic table. Preferably the metal ion is a transition metal or lanthanide ion, especially a transition metal ion, e.g. one from groups 3 to 6 of the periodic table, Specific metal ions of interest include Sc, Y, Ti, Zr, Hf, V, Nb, Ta, Cr, Mo and W. However, the metal is preferably Sc, Y, Cr, Ti, Zr or Hf, most especially Zr of Hf.

The oxidation state of the metal ion is governed primarily by the nature of the metal ion in question and the stability of the individual oxidation states of each metal ion. Typically, however the metal ions will be in the 3+ or 4+ oxidation state especially 4+.

It will be appreciated that in the complexes of the invention, the metal ion M will also be coordinated by other ligands so as to satisfy the valency of the metal ion and to fill its available coordination sites. The nature of these further ligands can vary greatly but these will generally be σ-ligands.

By a σ-ligand is meant a group bonded to the metal at one or more places via a single atom, e.g. a hydrogen, halogen, silicon, carbon, oxygen, sulphur or nitrogen atom. Examples of such ligands include:

amido (e.g. $NH_2$)

halogenides (e.g. chloride and fluoride), hydrogen, $triC_{1-12}$ hydrocarbyl-silyl or -siloxy (e.g. trimethylsilyl), $triC_{1-6}$ hydrocarbylphosphimido (e.g. triisopropylphosphimido), $C_{1-12}$ hydrocarbyl or hydrocarbyloxy (e.g. methyl, ethyl, phenyl, benzyl and methoxy), $diC_{1-6}$ hydrocarbylamido (e.g. dimethylamido and diethylamido), and 5 to 7 ring membered heterocyclyl (e.g. pyrrolyl, furanyl and pyrrolidinyl).

Highly preferred σ-ligands are chloro, $C_{1-6}$ alkyl, benzyl and amido (e.g. —$NH_2$ or $NMe_2$.

Preferred complexes of the invention therefore comprise

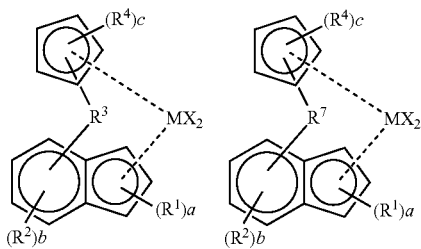

wherein each X is a sigma ligand and all other variables are as herein before defined.

In the ligands of the invention, the subscript "a" is preferably 0, i.e. the 5-membered ring of the indenyl is preferably unsubstituted or "a" is 1 or 2, preferably 1. If one substituent is present then it is preferably in the 2-position of the 5-membered ring.

The substituent is preferably a $C_{1-6}$-alkyl group, especially methyl or tertbutyl, or is phenyl. Highly preferably, the substituent is 2-methyl. Where more than one substituent is present it is preferred if these are the same.

In the ligands of the invention, the subscript "b" is preferably 0, i.e. the 6-membered ring of the indenyl is preferably unsubstituted other than by the bridge or "b" is 1. If a substituent is present then it is preferably not adjacent the bridge. Preferably, the substituent will be on the 5-position of the indenyl ring. The substituent is preferably a $C_{1-6}$-alkyl, especially methyl or tertbutyl, or is phenyl. Highly preferably, the substituent is 5-tertbutyl. Where more than one substituent is present it is preferred if these are the same.

Still more preferred ligands are those carrying 2 and 5 substituents, especially, 2-methyl-5-tertbutyl.

In the ligands of the invention, the subscript "c" may be 0, 1, 2, 3 or 4. If a substituent is present then it is preferably a $C_{1-6}$alkyl group, especially methyl, tert butyl or phenyl. Where more than one substituent is present it is preferred if these are the same.

In a further preferred embodiment therefore, the Cp ring is substituted by 4 $C_{1-6}$-alkyl groups, e.g. 4 methyl groups.

In a further highly preferred embodiment two $R^4$ groups attached to adjacent ring atoms together form an optionally substituted 6-membered fused carbon ring which can be saturated or more preferably unsaturated so as to form an indenyl type structure with the five membered ring. In a further preferred embodiment, the two remaining $R^4$ groups may also be taken together to form an optionally substituted 6-membered fused ring which can be saturated or more preferably unsaturated so as to form an fluorenyl type structure.

It is, of course, possible for one $R^4$ group to represent a $C_{1-6}$ alkyl or the like and two other $R^4$ groups may also be taken together to form an optionally substituted 6-membered fused ring, i.e. c is 3 in this scenario.

Where further ring structures are present, these may be optionally substituted as discussed above, e.g. with $C_{1-6}$ alkyl groups or phenyl. The bridging group $R^3$ however must bind to the five membered ring in any such ligand as depicted in formula (I).

The nature of the $R^5$ substituent will vary depending on the nature of the atom to which it is attached. Preferred $-N(R^5)_2$ groups are $NH_2$ and $NMe_2$. Any $R^5$ groups present are thus preferrably identical and are preferably hydrogen or $C_{1-6}$-alkyl. A further preferred embodiment is where two $R^5$ groups form a 6-membered ring with the N atom to which they are attached.

$R^3$ is preferably bound to the 4 or 7 position of the indenyl group. $R^3$ is preferably $CR^5_2CR^5_2$ or $SiR^5_2$.

Preferably both $R^5$ groups on the bridge are the same. More preferably both $R^5$ groups are $C_{1-6}$alkyl groups, especially methyl, or hydrogen. Highly preferred groups $R^3$ are $SiMe_2$ or $CH_2CH_2$.

$R^7$ is $CR^5_2$ with preferred $R^5$ groups as above. A highly preferred group $R^7$ is $CH_2$.

Highly preferred complexes of the invention are therefore of formula (V)

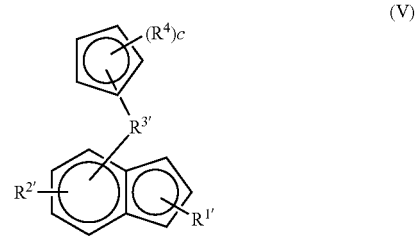

Wherein $R^4$ and c are as hereinbefore defined, $R^{1'}$ is hydrogen or $C_{1-6}$-alkyl; $R^{2'}$ is hydrogen or $C_{1-6}$-alkyl; and $R^{3'}$ is $SiMe_2$ or $CH_2CH_2$.

Certain further complexes also form an aspect of the invention. These catalysts comprise $CR^5_2$, bridges, especially methylene bridges, from the 4 or 7 position of the indenyl ring but have particular substitution patterns on the ring.

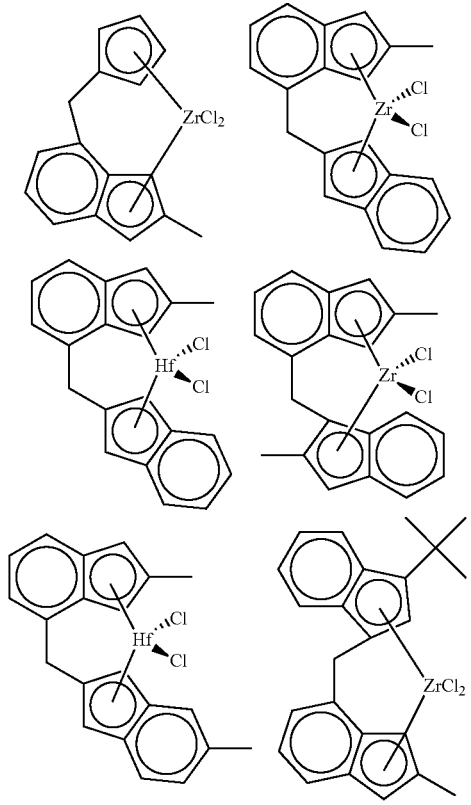

-continued

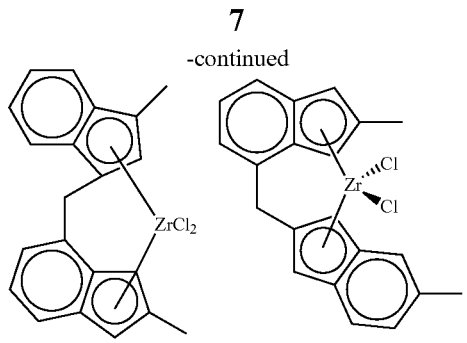

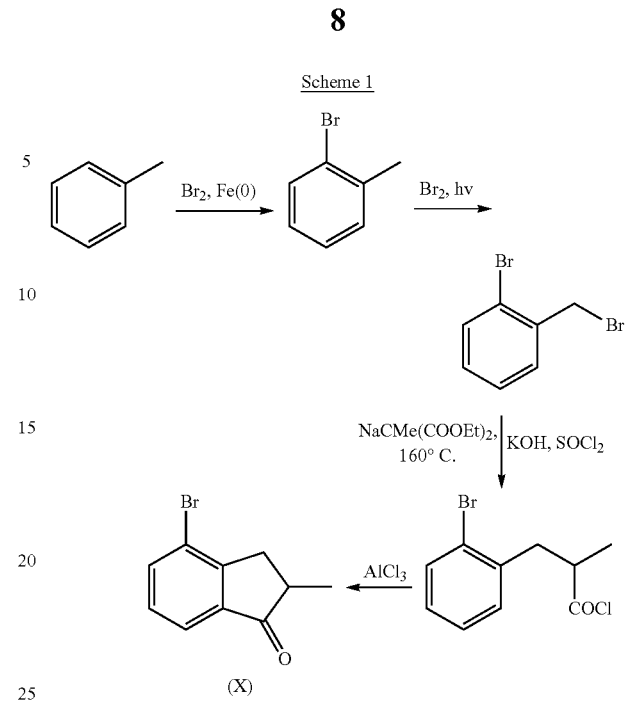

Scheme 1

The catalysts of the invention may exist in diastereomeric forms. The invention covers these forms as a mixture of individually.

Throughout the disclosure above, where a narrower definition of a substituent is presented, that narrower definition is deemed disclosed in conjunction with all broader and narrower definitions of other substituents in the application.

Synthesis

The ligands required to form the cataysts of the invention can be synthesised by any process and the skilled organic chemist would be able to devise various synthetic protocols for the manufacture of the necessary ligand materials. The prior art is replete with description of the formation of bridged metallocenes and the principles by which these compounds are made are applicable here to.

The crucial step in the formation of the ligands of the invention is of course, the formation of the bridging group at the 4 to 7 position of the indenyl ring. Whilst the skilled man is able to devise various methods of achieving this, one such method for each of the preferred bridges of the invention is presented below.

Intermediate

A useful intermediate in the formation of all the necessary bridges is a compound of formula (X)

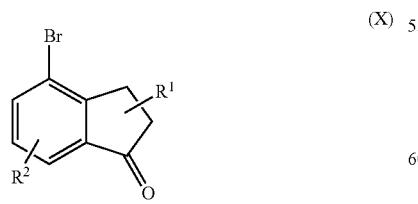

(X)

This compound can be prepared from a toluene analogue which is brominated both alpha to the methyl group and on the methyl group before the formation of the five membered ring as shown below in Scheme 1.

It will be appreciated that different substituents can be introduced onto compounds of formula (X) using known chemistry. For example, an alkyl group could be introduced at the 1 position (carbonyl) if it is reacted with a grignard reagent before the resulting hydroxy group is eliminated.

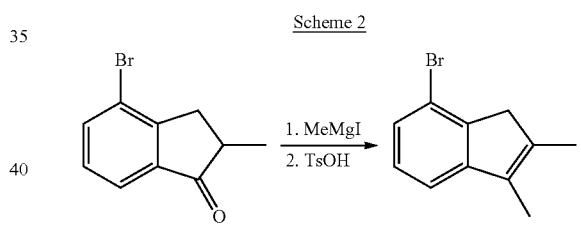

Scheme 2

Silyl Bridges

Once formed the compound of formula (X) or analoguous compounds can be reduced to form a 4-bromoindene structure. Formation of a silyl bridge precursor is then easily effected by conversion of the bromoindene into a grignard type structure using magnesium and nucleophilic substitution with for example, with $SiMe_2Cl_2$.

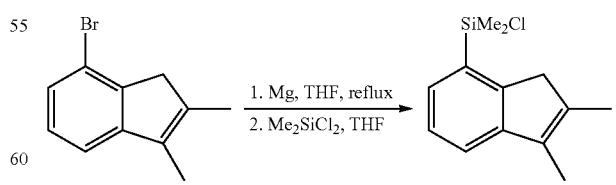

Scheme 3

Ethylene Bridges

To form an ethylene bridge an ethyl group needs to be added to indene group at an appropriate position. This can be achieved through the reaction of a suitable anion with ethylene oxide as shown in Scheme 4 below. The hydroxyl group formed is readily converted into a more active leaving group, e.g. bromide, to allow easy reaction with the other η ligands presented as nucleophiles or through grignard chemistry as above. The indene rings are formed simply by reductive elimination of methanol using tosyl alcohol. This can be effected before bridge formation or after bridge formation.

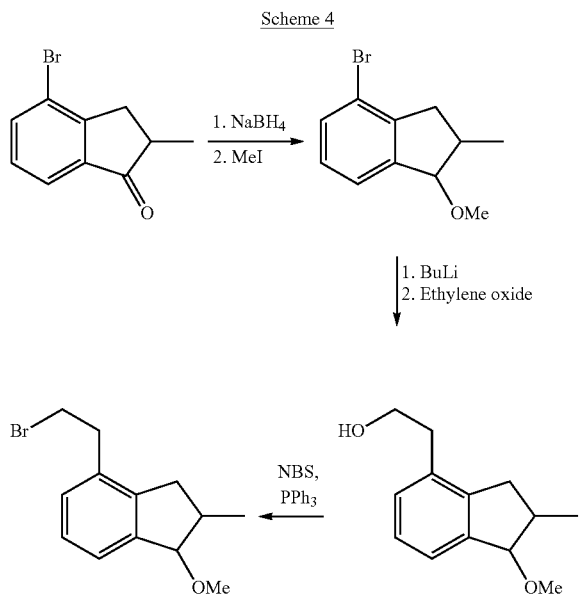

Methylene Bridges

These can also be made from the intermediate above if in a first step the carbonyl is converted to an alkoxy group (e.g. by reduction of the carbonyl and reaction of hydroxide with a suitable electrophile). The Br can then be replaced by —CHO, reduced to hydroxymethyl and activated, e.g. by tosylation or conversion to a bromide to form an electrophilic species capable of reaction with a cyclopentadienyl nucleophile. The indene ring is formed by elimination of the alkoxy group. These reactions are summarised below in Scheme 5.

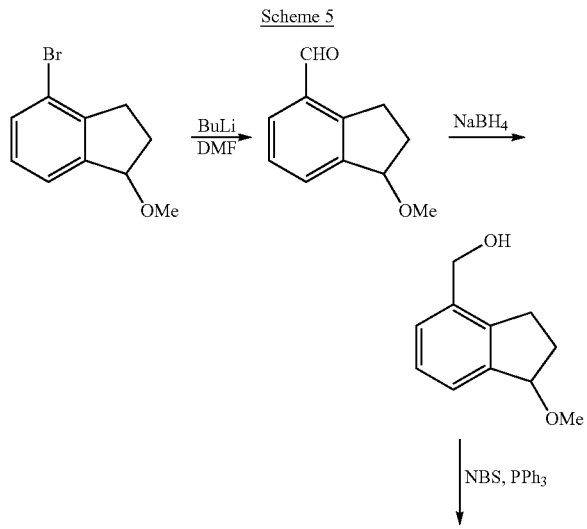

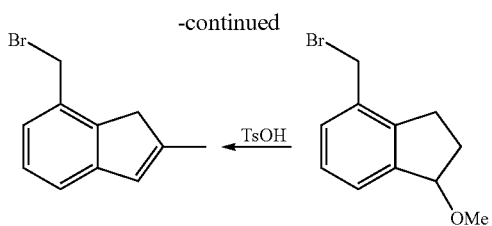

5/6 Position Bridge

Bridges at the 5 or 6 position can be introduced using the available starting material:

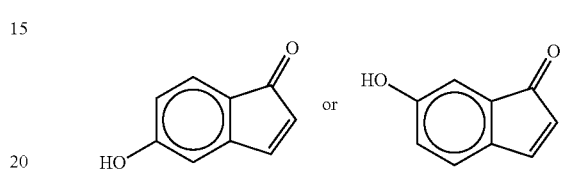

The OH group can be converted to Br using $Ph_3PBr_2$ and the resulting ketobromide manipulated as described above in connection with compound (X) and ethylene or silyl bridges.

Bridge Formation

Once a suitable indene compound has been produced carrying a precursor to a bridge at an appropriate position in the indenyl ring, the actual formation of the bridged complex is trivial as a cyclopentadienyl ion acts as a nucleophile displacing the leaving group from the bridge precursor thereby forming a bridged ligand. The cyclopentadienyl ion employed will, preferably, be functionalised as desired prior to formation of the bridged ligand.

Formation of the desired complex is effected by reacting the desired ligand with an appropriate quantity of base, e.g. an organolithium compound, such as methyllithium or butyllithium.

The ligand can then be metallated conventionally, e.g. by reaction with a halide of the metal, preferably in an organic solvent, e.g. a hydrocarbon or a hydrocarbon/ether mixture or ether (THF). The metal halide can, of course, contain substituents other than halides although typically the ligand is $MCl_3$ or especially $MCl_4$.

An alternative approach to the complexes is also envisaged where the ligand is reacted with $M(NMe_2)_4$ or $M(CH_2Ph)_4$. The resulting complexes may therefore contain amino or benzyl sigma ligands rather than halide ligands. In essence, as long as their are groups to displace, any metal compound can be used to form the complexes of the invention depending on the nature of any other ligands which the skilled man wants to be present.

σ-ligands other than chlorine may, however, also be introduced by displacement of chlorine from a complex metal chloride by reaction with appropriate nucleophilic reagent (e.g. methyl lithium or methylmagnesium chloride) or using, instead of a metal halide, a reagent such as tetrakisdimethylamidotitanium or metal compounds with mixed chloro and dimethylamido ligands.

Catalysts

To form an active catalytic species it is normally necessary to employ a cocatalyst as is well known in the art. Cocatalysts used to activate metallocene catalysts are suitable for use in this invention. Complex and cocatalyst may be introduced into the polymerization reactor separately or together or, more preferably they are pre-reacted and their reaction product is introduced into the polymerization reactor.

As mentioned above, the olefin polymerisation catalyst system of the invention comprises (i) a complex in which the metal ion is coordinated by a ligand of the invention; and normally (ii) an aluminium alkyl compound (or other appropriate cocatalyst), or the reaction product thereof.

While the aluminium alkyl compound may be an aluminium trialkyl (e.g. triethylaluminium (TEA)) or an aluminium dialkyl halide (e.g. diethyl aluminium chloride (DEAC)), it is preferably an alumoxane, either MAO or an alumoxane other than MAO, such as an isobutylalumoxane, e.g. TIBAO (tetraisobutylalumoxane) or HIBAO (hexaisobutylalumoxane). Alternatively, however, the alkylated (e.g. methylated) catalysts of the invention may be used with other cocatalysts, e.g. boron compounds such as $B(C_6F_5)_3$, $C_6H_5N(CH_3)_2H{:}B(C_6F_5)_4$, $(C_6H_5)_3C{:}B(C_6F_5)_4$ or $Ni(CN)_4[B(C_6F_5)_3]_4^{2-}$.

However, when the metal in the catalyst is a group 3 transition metal, i.e. Sc, Y, La or Ac, a co-activator may not necessarily be required since such catalyst species are already in an active form.

If desired the complex, complex/cocatalyst mixture or a complex/cocatalyst reaction product may be used in unsupported form, i.e. complex and MAO can be precipitated without an actual carrier material and used as such. However the complex or its reaction product with the cocatalyst is preferably introduced into the polymerization reactor in supported form, e.g. impregnated into a porous particulate support.

The particulate support material used is preferably an organic or inorganic material, e.g. a polymer (such as for example polyethylene, polypropylene, an ethylene-propylene copolymer, another polyolefin or polystyrene or a combination thereof). Such polymeric supports may be formed by precipitating a polymer or by a prepolymerization, e.g. of monomers used in the polymerization for which the catalyst is intended. However, the support is especially preferably a metal or metalloid oxide such as silica, alumina or zirconia or a mixed oxide such as silica-alumina, in particular silica, alumina or silica-alumina.

Particularly preferably, the support material is acidic, e.g. having an acidity greater than or equal to silica, more preferably greater than or equal to silica-alumina and even more preferably greater than or equal to alumina. The acidity of the support material can be studied and compared using the TPD (temperature programmed desorption of gas) method. Generally the gas used will be ammonia. The more acidic the support, the higher will be its capacity to adsorb ammonia gas. After being saturated with ammonia, the sample of support material is heated in a controlled fashion and the quantity of ammonia desorbed is measured as a function of temperature.

Especially preferably the support is a porous material so that the complex may be loaded into the pores of the support, e.g. using a process analogous to those described in WO94/14856 (Mobil), WO95/12622 (Borealis) and WO96/00243 (Exxon). The particle size is not critical but is preferably in the range 5 to 200 µm, more preferably 20 to 80 µm.

Before loading, the particulate support material is preferably calcined, i.e. heat treated, preferably under a non-reactive gas such as nitrogen. This treatment is preferably at a temperature in excess of 100° C., more preferably 200° C. or higher, e.g. 200-800° C., particularly about 300° C. The calcination treatment is preferably effected for several hours, e.g. 2 to 30 hours, more preferably about 10 hours.

The support may be treated with an alkylating agent before being loaded with the catalyst. Treatment with the alkylating agent may be effected using an alkylating agent in a gas or liquid phase, e.g. in an organic solvent for the alkylating agent. The alkylating agent may be any agent capable of introducing alkyl groups, preferably $C_{1-6}$ alkyl groups and most especially preferably methyl groups. Such agents are well known in the field of synthetic organic chemistry. Preferably the alkylating agent is an organometallic compound, especially an organoaluminium compound (such as trimethylaluminium (TMA), dimethyl aluminium chloride, triethylaluminium) or a compound such as methyl lithium, dimethyl magnesium, triethylboron, etc.

The quantity of alkylating agent used will depend upon the number of active sites on the surface of the carrier. Thus for example, for a silica support, surface hydroxyls are capable of reacting with the alkylating agent. In general, an excess of alkylating agent is preferably used with any unreacted alkylating agent subsequently being washed away.

Following treatment of the support material with the alkylating agent, the support is preferably removed from the treatment fluid and any excess treatment fluid is allowed to drain off.

The optionally alkylated support material is loaded with the catalyst. This loading may be effected by using a solution of the catalyst in an organic solvent therefor, e.g. as described in the patent publications referred to above. Preferably, the volume of catalyst solution used is from 50 to 500% of the pore volume of the carrier, more especially preferably 80 to 120%. The concentration of catalyst compound in the solution used can vary from dilute to saturated depending on the amount of metallocene active sites that it is desired be loaded into the carrier pores.

The active metal (i.e. the metal of the catalyst) is preferably loaded onto the support material at from 0.1 to 4%, preferably 0.5 to 3.0%, especially 1.0 to 2.0%, by weight metal relative to the dry weight of the support material.

After loading of the catalyst onto the support material, the loaded support may be recovered for use in olefin polymerization, e.g. by separation of any excess catalyst solution and if desired drying of the loaded support, optionally at elevated temperatures, e.g. 25 to 80° C.

Alternatively, a cocatalyst, e.g. an alumoxane or an ionic catalyst activator (such as a boron or aluminium compound, especially a fluoroborate) may also be mixed with or loaded onto the catalyst support material. This may be done subsequently or more preferably simultaneously to loading of the complex, for example by including the cocatalyst in the solution of the catalyst, by contacting the catalyst loaded support material with a solution of the cocatalyst or catalyst activator, e.g. a solution in an organic solvent, or by first impregnating the cocatalyst with a support and then contacting the cocatalyst impregnated support with a solution of the catalyst or neat catalyst (e.g. as described in WO96/32423). Alternatively however any such further material may be added to the catalyst-loaded support material in the polymerization reactor or shortly before dosing of the catalyst material into the reactor.

In this regard, as an alternative to an alumoxane it may be preferred to use a fluoroborate catalyst activator for the alkylated catalysts, especially a $B(C_6F_5)_3$ or more especially a —$B(C_6F_5)_4$ compound, such as $C_6H_5N(CH_3)_2H{:}B(C_6F_5)_4$ or $(C_6H_5)_3C{:}B(C_6F_5)_4$. Other borates of general formula $(cation)_a (borate)_b$ where a and b are positive numbers, may also be used.

As an alternative to the loading of the optionally alkylated support material with a solution of the procatalyst in an organic solvent, loading of the catalyst may be effected by mixing it with the optionally alkylated support material in the absence of solvents with said carrier at a temperature of at least 50° C. but less than the vaporisation temperature of the metallocene compound. The particular features of this socalled dry mixing method are disclosed in WO 96/32423 (Borealis). If use of a cocatalyst/catalyst activator in such process is desired, this may be impregnated into the optionally alkylated support material prior to loading of the catalyst.

Where such a cocatalyst or catalyst activator is used, it is preferably used in a mole ratio to the metallocene of from 0.1:1 to 10000:1, especially 1:1 to 50:1, particularly 1:2 to 30:1. More particularly, where an alumoxane cocatalyst is used, then for an unsupported catalyst the aluminium:metallocene metal (M) molar ratio is conveniently 2:1 to 10000:1, preferably 50:1 to 1000:1. Where the catalyst is supported the Al:M molar ratio is conveniently 2:1 to 10000:1 preferably 50:1 to 400:1. Where a borane cocatalyst (catalyst activator) is used, the B:M molar ratio is conveniently 2:1 to 1:2, preferably 9:10 to 10:9, especially 1:1. When a neutral triarylboron type cocatalyst is used the B:M molar ratio is typically 1:2 to 500:1, however some aluminium alkyl would normally also be used. When using ionic tetraaryl borate compounds, it is preferred to use carbonium rather than ammonium counterions or to use B:M molar ratio 1:1.

Where the further material is loaded onto the catalyst loaded support material, the support may be recovered and if desired dried before use in olefin polymerization.

The olefin polymerized using the catalyst of the invention is preferably ethylene or an alpha-olefin or a mixture of ethylene and an α-olefin or a mixture of alpha olefins, for example $C_{2-20}$ olefins, e.g. ethylene, propene, 1-butene, 1-hexene, 4-methyl-1-pentene, 1-octene etc. The olefins polymerized in the method of the invention may include any compound which includes unsaturated polymerizable groups. Thus for example unsaturated compounds, such as $C_{6-20}$ olefins (including cyclic and polycyclic olefins (e.g. norbornene)), and polyenes, especially $C_{4-20}$ dienes, may be included in a comonomer mixture with lower olefins, e.g. $C_{2-5}$ α-olefins. Diolefins (i.e. dienes) are suitably used for introducing long chain branching into the resultant polymer. Examples of such dienes include am linear dienes such as 1,5-hexadiene, 1,6-heptadiene, 1,8-nonadiene, 1,9-decadiene, etc.

In general, where the polymer being produced is a homopolymer it will preferably be polyethylene or polypropylene. Where the polymer being produced is a copolymer it will likewise preferably be an ethylene or propylene copolymer with ethylene or propylene making up the major proportion (by number and more preferably by weight) of the monomer residues. Comonomers, such as $C_{4-6}$ alkenes, will generally be incorporated to contribute to the mechanical strength of the polymer product.

Polymerization in the method of the invention may be effected in one or more, e.g. 1, 2 or 3, polymerization reactors, using conventional polymerization techniques, e.g. gas phase, solution phase, slurry or bulk polymerization.

In general, a combination of slurry (or bulk) and at least one gas phase reactor is often preferred, particularly with the reactor order being slurry (or bulk) then one or more gas phase.

For slurry reactors, the reaction temperature will generally be in the range 60 to 110° C. (e.g. 85-110° C.), the reactor pressure will generally be in the range 5 to 80 bar (e.g. 50-65 bar), and the residence time will generally be in the range 0.3 to 5 hours (e.g. 0.5 to 2 hours). The diluent used will generally be an aliphatic hydrocarbon having a boiling point in the range −70 to +100° C. In such reactors, polymerization may if desired be effected under supercritical conditions.

For gas phase reactors, the reaction temperature used will generally be in the range 60 to 115° C. (e.g. 70 to 110° C.), the reactor pressure will generally be in the range 10 to 25 bar, and the residence time will generally be 1 to 8 hours. The gas used will commonly be a non-reactive gas such as nitrogen together with monomer (e.g. ethylene).

For solution phase reactors, the reaction temperature used will generally be in the range 130 to 270° C., the reactor pressure will generally be in the range 20 to 400 bar and the residence time will generally be in the range 0.005 to 1 hour. The solvent used will commonly be a hydrocarbon with a boiling point in the range 80-200° C.

Generally the quantity of catalyst used will depend upon the nature of the catalyst, the reactor types and conditions and the properties desired for the polymer product. Conventional catalyst quantities, such as described in the publications referred to herein, may be used.

The polymer produced using the catalysts of the invention will generally possess a high Mw, e.g. greater than 200,000, preferably greater than 400,000, more preferably greater than 600,00, especially more than 800,000. Such polymers are ideally used for MDPE and HDPE applications, i.e. where the density of the polymer is 930 kg/m3 or greater, especially 940 kg/m3 or greater.

The polymers made by the catalysts of the invention are useful in all kinds of end articles such as pipes, films, moulded articles (e.g. injection moulded, blow moulded, rotomoulded articles), extusion coatings and so on.

The invention will now be illustrated by reference to the following non-limiting Examples:

EXPERIMENTAL

The following instrumentation was used:
NMR spectroscopy: Bruker DPX 300 NMR spectrometer
IR spectroscopy: Nicolet 5700 FT-IR spectrometer equipped with a Smart Orbit diamond ATR unit
Single crystal structure analysis: Nonius Kappa-CCD equipped with graphite-monochromated Mo—K(alpha) radiation
Ligand and Complex Synthesis Example 1

4-(Bromomethyl)-1-methoxy-2-methylindane

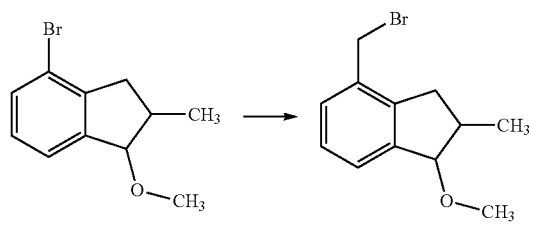

To a solution of 48.2 g (0.2 mol) of 4-bromo-2-methyl-methoxyindane in 700 ml of THF 80.0 ml 2.5 M (0.2 mol) n-BuLi in hexanes was added for 10 min at −80° C. The resulting mixture was stirred for 2 h at this temperature, then cooled to −110° C., and 18.7 ml (17.6 g, 0.241 mol) of DMF was added at vigorous stirring. This mixture was warmed to room temperature, 10 ml of water was added, and then the resulting mixture was evaporated in vacuum. To a solution of the residue in 1050 ml of a mixture of THF-methanol (2:1, vol.), 15.1 g (0.4 mol) of $NaBH_4$ was added in small portions at vigorous stirring for ca. 5 min. This mixture was stirred for 15 min at room temperature and then evaporated to dryness. To the residue 500 ml of warm water was added, and the crude alcohol was extracted with 3×200 ml of methylene dichloride. The combined organic extract was dried over $Na_2SO_4$ and then evaporated to dryness. To a mixture of the residue, 52.5 g (0.2 mol) of PPh$_3$, and 800 ml of THF 35.6 g (0.2 mol) of NBS was added for ca. 5 min at 20° C. The resulting mixture was stirred for 5 min and evaporated to dryness. A mixture of the residue with 500 ml of hexanes was filtered through glass frit (G3). The precipitate was additionally washed by 3×300 ml of hexanes. The combined organic extract was evaporated to dryness. The product was isolated using short column with Silica Gel 60 (40-63 um, d 130 mm, l 100 mm, eluent hexanes/ether=20/1, vol.). Yield 37.8 Г (74%) of a ca. 1 to 1.5 mixture of two diastereomers.

Anal. calc. for C$_{12}$H$_{15}$BrO: C, 56.49; H, 5.93. Found: C, 56.60; H, 6.04.

$^1$H NMR (C$_6$D$_6$): δ 7.11-7.32 (m, 6H, 5,6,7-H in indenyl of both isomers), 4.47 (d, J=5.6 Hz, 1H, MeOCH of minor isomer), 4.41 (s, 2H, CH$_2$Br of major isomer), 4.40 (s, 2H, CH$_2$Br of minor isomer), 4.37 (d, J=4.1 Hz, 1H, MeOCH of major isomer), 3.42 (s, 3H, OMe of major isomer), 3.36 (s, 3H, OMe of minor isomer), 3.22 (dd, J=15.7 Hz, J=7.3 Hz, 1H, 3-CHH' of major isomer), 2.95 (dd, J=15.7 Hz, J=7.1 Hz, 1H, 3-CHH' of minor isomer), 2.41-2.71 (m, 4H, 3-CHH' and CHMe of both isomers), 1.16 (d, J=7.0 Hz, 3H, 2-Me of major isomer), 1.10 (d, J=6.9 Hz, 3H, 2-Me of minor isomer).

$^{13}$C{$^1$H} NMR (C$_6$D$_6$), major isomer: δ 137.9, 137.43, 137.40, 123.4, 121.3, 120.0, 85.4, 50.8, 33.9, 30.7, 25.7, 13.7.

7-(Bromomethyl)-2-methyl-1H-indene

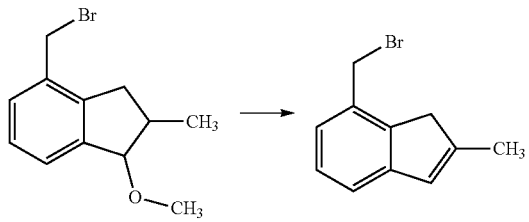

To a solution of 37.5 g (0.147 mol) of 4-(bromomethyl)-1-methoxy-2-methylindane in 600 ml of toluene 3.12 g (16.4 mmol) of TsOH was added at 110° C. This mixture was refluxed with Dean-Stark trap within 12 min and then passed through short column with Silica Gel 60 (40-63 um, d 90 mm, l 80 mm). The Silica Gel layer was additionally washed by 500 ml of toluene. The combined elute was evaporated to dryness. The product was isolated by flash chromatography on short column with Silica Gel 60 (40-63 um, d 90 mm, l 80 mm; eluent: hexanes). Yield 33.2 g (97%).

Anal. calc. for C$_{11}$H$_{11}$Br: C, 59.22; H, 4.97. Found: C, 59.47; H, 5.11.

$^1$H NMR (CDCl$_3$): δ 7.19-7.23 (m, 2H, 4,6-H), 7.10 (m, 1H, 5-H), 6.50 (m, 1H, 3-H), 4.56 (s, 2H, CH$_2$Br), 3.36 (br.s, 2H, 1,1'-H), 2.19 (m, 3H, 2-Me).

$^{13}$C{$^1$H} NMR (CDCl$_3$): δ 146.6, 146.2, 142.4, 132.0, 127.17, 127.14, 124.4, 120.2, 40.9, 31.7, 16.7.

Chloro(dimethyl)(2-methyl-1H-inden-7-yl)silane

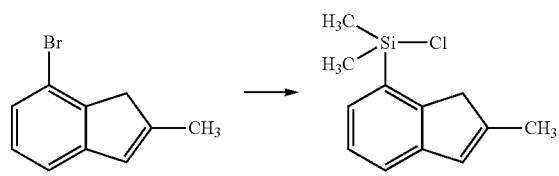

To 1.63 g (67 mmol) of magnesium turnings (activated by 0.2 ml of 1,2-dibromoethane for 10 min) in 50 ml of THF a solution of 11.6 g (55 mmol) of 2-methyl-7-bromoindene in 350 ml of THF was added dropwise at vigorous stirring for ca. 40 min. This mixture was additionally refluxed for 1 h, and then cooled to room temperature. The Grignard reagent obtained was added dropwise at vigorous stirring to a solution of 21.4 g (166 mmol) of dichlorodimethylsilane in 50 ml of THF for 1 h at room temperature. The resulting mixture was stirred for 12 h and then evaporated to dryness. The residue was dissolved in 100 ml of ether, and the solution obtained was filtered through glass frit (G3). The precipitate was additionally washed by 3×50 ml of ether. The combined ether solution was evaporated to dryness, and the residue was distilled in vacuum, by 110-112° C./1 mm Hg. Yield 9.80 Г (80%).

Anal. calc. for C$_{12}$H$_{15}$ClSi: C, 64.69; H, 6.79. Found: C, 64.88; H, 6.55.

$^1$H NMR (CDCl$_3$): δ 7.42-7.47 (m, 2H, 4,6-H), 7.34-7.39 (m, 1H, 5-H), 6.60 (m, 1H, 3-H), 3.55 (br.s, 2H, 1,1'-H), 2.28 (br.s, 3H, 2-Me), 0.86 (s, 6H, Me$_2$SiCl).

$^{13}$C{$^1$H} NMR (CDCl$_3$): δ 148.5, 146.3, 145.6, 129.8, 128.5, 126.8, 125.9, 122.0, 43.6, 16.7, 2.5.

Example 2

2-(1-Methoxy-2-methyl-2,3-dihydro-1H-inden-4-yl)ethanol

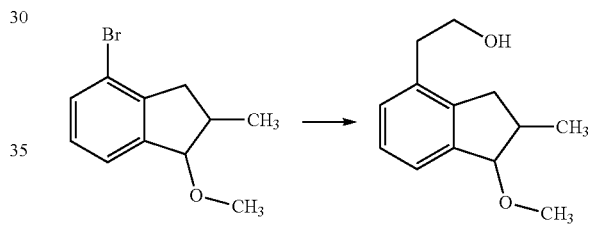

To a solution of 20.0 g (82.9 mmol) of 4-bromo-2-methyl-methoxyindane in 200 ml of THF 33.2 ml of 2.5 M (83.0 mmol) n-BuLi in hexanes was added for 20 min at −80° C. This mixture was stirred for 40 min at this temperature, cooled to −110° C., and 4.38 g (99.4 mmol) of ethylene oxide was added by one portion at vigorous stirring. The resulting mixture was stirred for 12 h at room temperature, and then 10 ml of water was added. The organic layer was separated and evaporated to dryness. To the residue 200 ml of water was added, and the crude product was extracted with 3×100 ml of dichloromethane. The combined organic extract was dried over Na$_2$SO$_4$ and evaporated to dryness. The product was isolated by flash chromatography using short column with Silica Gel 60 (40-63 um, d 110 mm, 190 mm; eluent: hexanes/ether=20/1). Yield 12.7 g (74%) of a ca. 1 to 1.2 mixture of two diastereomers.

Anal. calc. for C$_{13}$H$_{18}$O$_2$: C, 75.69; H, 8.80. Found: C, 75.87; H, 8.93.

$^1$H NMR (CDCl$_3$): δ 7.29 (m, 2H, 6-H of both isomers), 7.23 (m, 2H, 7-H of both isomers), 7.15 (m, 2H, 5-H of both isomers), 4.58 (d, J=5.5 Hz, 1H, CHOMe of minor isomer), 4.48 (d, J=4.0 Hz, 1H, CHOMe of major isomer), 3.53 (s, 3H, OMe of major isomer), 3.48 (s, 3H, OMe of minor isomer), 3.74 (m, 4H, CH$_2$Br of both isomers), 3.27 (dd, J=15.9 Hz, J=7.7 Hz, 1H, 3-CHH' of major isomer), 2.97 (dd, J=15.0 Hz, J=6.8 Hz, 1H, 3-CHH' of minor isomer), 2.82 (m, 4H, CH$_2$CH$_2$Br of both isomers), 2.73 (dd, J=15.0 Hz, J=7.0 Hz, 1H, 3-CHH' of minor isomer), 2.54-2.71 (m, 4H, CHMe and OH of both isomers), 2.46 (dd, J=15.9 Hz, J=5.0 Hz, 1H, 3-CHH' of major isomer), 1.18 (d, J=7.0 Hz, 3H, 2-Me of major isomer), 1.15 (d, J=7.9 Hz, 3H, 2-Me of minor isomer).

$^{13}C\{^1H\}$ NMR (CDCl$_3$): δ 142.6, 142.4, 141.9 (2C), 134.8, 134.6, 128.9, 128.7, 126.6, 126.2, 123.4, 123.2, 91.4, 86.1, 62.3, 62.2, 56.6, 56.2, 39.1, 38.3, 36.8, 36.5, 36.4, 36.2, 19.3, 13.5.

4-(2-Bromoethyl)-1-methoxy-2-methylindane

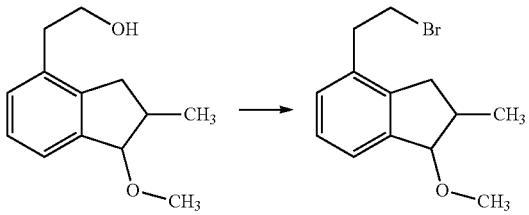

To a mixture of 41.3 g (0.2 mol) of 2-(1-methoxy-2-methyl-2,3-dihydro-1H-inden-4-yl)ethanol and 52.5 g (0.2 mol) PPh$_3$ in 800 ml of THF 35.6 g (0.2 mol) of NBS was added at vigorous stirring for 5 min at 0° C. This mixture was stirred for 2 h at room temperature and then evaporated to dryness. A solution of the residue in 500 ml of hexanes was filtered through glass frit (G3), and the precipitate was additionally washed by 3×300 ml hexanes. The combined organic extract was evaporated to dryness. The product was isolated from the residue using flash chromatography on Silica Gel 60 (40-63 um, d 80 mm, l 250 mm; eluent: hexanes/ether=20/1, vol.). Yield 39.3 g (73%) of ca. 1 to 1 mixture of the diastereomers A and B.

Anal. calc. for C$_{13}$H$_{17}$BrO: C, 58.01; H, 6.37. Found: C, 58.26; H, 6.17.

$^1$H NMR (CDCl$_3$): δ 7.30 (m, 2H, 6-H in indenyl of A and B), 7.20 (m, 2H, 7-H in indenyl of A and B), 7.12 (m, 2H, 5-H in indenyl of A and B), 4.52 (m, 1H, 1-H in indenyl of A), 4.41 (m, 1H, 1-H in indenyl of B), 3.53 (m, 4H, CH$_2$CH$_2$Br of A and B), 3.47 (s, 3H, OMe of B), 3.42 (s, 3H, OMe of A), 3.22 (dd, J=15.8 Hz, J=7.6 Hz, 1H, 3-H in indenyl of B), 3.15 (m, 4H, CH$_2$CH$_2$Br of A and B), 2.92 (dd, J=14.9 Hz, J=6.7 Hz, 1H, 3-H in indenyl of A), 2.48-2.71 (m, 3H, 2,3-H in indenyl of A and 2-H in indenyl of B), 2.42 (dd, J=15.8 Hz, J=4.8 Hz, 1H, 3-H in indenyl of B), 1.18 (d, J=7.1 Hz, 3H, 2-Me in indenyl of B), 1.13 (d, J=6.6 Hz, 3H, 2-Me in indenyl of A).

$^{13}C\{^1H\}$ NMR (CDCl$_3$): δ 143.1, 142.6, 142.2, 141.7, 135.1, 135.0, 128.5, 128.4, 126.8, 126.5, 124.1, 123.8, 91.3, 85.9, 56.7, 56.5, 39.4, 38.5, 36.80, 36.78, 36.7, 36.5, 31.7, 31.6, 19.4, 13.6.

4/7-(2-Bromoethyl)-2-methyl-1H-indene

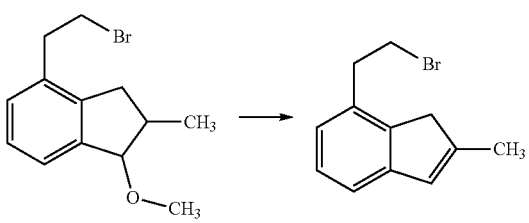

To a hot (110° C.) solution of 10.0 g (37.2 mmol) of 4-(2-bromoethyl)-1-methoxy-2-methylindane in 200 ml of toluene 0.8 g of TsOH was added. This mixture was refluxed with Dean-Stark trap for 10 min and then passed through the layer of Silica Gel 60 (40-63 um, d 80 mm, l 50 mm). The Silica Gel layer was additionally washed by 500 ml of toluene. The combined organic extract was evaporated to dryness. The product was isolated by flash chromatography using a short column with Silica Gel 60 (40-63 um, d 80 mm, l 50 mm; eluent: hexanes). Yield 8.46 g (96%) of a ca. 1 to 1.5 mixture of 4- and 7-(2-bromoethyl)-2-methyl-1H-indenes.

Anal. calc. for C$_{12}$H$_{13}$Br: C, 60.78; H, 5.53. Found: C, 61.00; H, 5.65.

$^1$H NMR (CDCl$_3$): δ 6.92-7.31 (m, 6H, 5,6,7-H and 4,5,6-H of minor and major isomers, respectively), 6.60 (m, 1H, 3-H in indenyl of minor isomer), 6.51 (m, 1H, 3-H in indenyl of major isomer), 3.62 (m, 2H, CH$_2$Br of major isomer), 3.57 (m, 2H, CH$_2$Br of minor isomer), 3.32 (br.s, 2H, 1,1'-H in indenyl of minor isomer), 3.28 (br.s, 2H, 1,1'-H in indenyl of major isomer), 3.27 (m, 2H, CH$_2$CH$_2$Br of minor isomer), 3.23 (m, 2H, CH$_2$CH$_2$Br of major isomer), 2.19 (m, 3H, 2-Me in indenyl of minor isomer), 2.18 (m, 3H, 2-Me in indenyl of major isomer).

Ligand 1

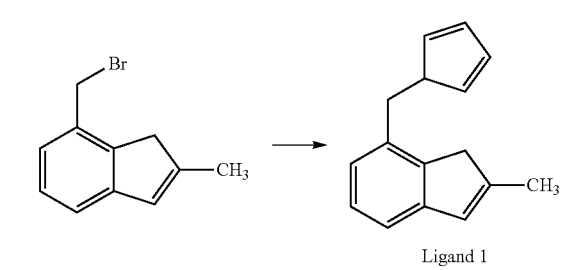

Ligand 1

To a solution of 484 mg (6.72 mmol) of CpLi in 80 ml of THF a solution of 1.50 g (6.72 mmol) of 7-(bromomethyl)-2-methyl-1H-indene in 10 ml of THF was added dropwise for 5 min at −80° C. The reaction mixture was stirred for 1 h at room temperature, 1 ml of water was added, and then evaporated to dryness. To the residue 100 ml of water was added, and the crude product was extracted with 3×50 ml of dichloromethane. The combined extract was dried over Na$_2$SO$_4$ and evaporated to dryness. The product was isolated by flash chromatography using a short column with Silica Gel 60 (40-63 um, d 50 mm, l 50 mm; eluent: hexanes). Yield 1.13 g (81%).

Anal. calc. for C$_{16}$H$_{16}$: C, 92.26; H, 7.74. Found: C, 92.09; H, 7.58.

$^1$H NMR (CDCl$_3$): δ 6.94-7.30 (m, 3H), 6.98-6.66 (m, 4H), 3.76-3.89 (m, 2H), 3.23-3.34 (m, 2H), 2.87-3.03 (m, 2H), 2.18 (m, 3H).

Ligand 3

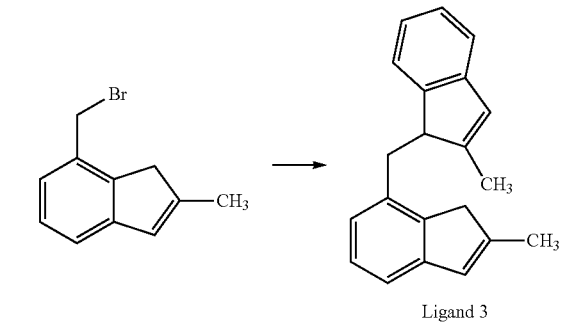

Ligand 3

To a solution of 1.30 g (10 mmol) of 2-methyl-1H-indene in 90 ml of ether 4.0 ml of 2.5 M (10 mmol) n-BuLi in hexanes was added at 0° C. This mixture was stirred for 2 h at room temperature, and then a solution of 2.23 g (10 mmol) of 7-(bromomethyl)-2-methyl-1H-indene in 15 ml of THF was added dropwise at vigorous stirring for 10 min at −80° C. The resulting mixture was stirred for 12 h at room temperature, and then 1 ml of water was added. This mixture was evaporated to dryness, and 100 ml of water was added. The crude product was extracted with 3×50 ml of dichloromethane. The combined organic extract was dried over $Na_2SO_4$ and evaporated to dryness. The product was isolated by flash chromatography using a short column with Silica Gel 60 (40-63 um, d 60 mm, l 70 mm; eluent: hexanes. Yield 2.50 g (92%) of 2-methyl-1-[(2-methyl-1H-inden-7-yl)methyl]-1H-indene.

Anal. calc. for $C_{21}H_{20}$: C, 92.60; H, 7.40. Found: C, 92.77; H, 7.53.

$^1$H NMR ($CDCl_3$): δ 7.19-7.30 (m, 4H), 7.10 (m, 1H), 6.95 (m, 1H), 6.73 (m, 1H), 6.57 (m, 1H), 6.53 (m, 1H), 3.67 (dd, J=10.0 Hz, J=5.6 Hz, 1H, 1-H in 2-methylinden-1-yl), 3.30 (dd, J=13.8 Hz, J=5.6 Hz, 1H, CHH'CH), 3.17 (m, 2H, 1,1'-H in 2-methylinden-4-yl), 2.61 (dd, J=13.8 Hz, J=10.0 Hz, 1H, CHH'CH), 2.17 (br.s, 3H, Me in 2-methylinden-4-yl), 2.13 (br.s, 3H, Me in 2-methylinden-1-yl).

$^{13}C\{^1H\}$ NMR ($CDCl_3$): δ 149.6, 147.1, 145.9, 145.6, 144.4, 142.3, 135.0, 127.5, 126.6 (2C), 126.4, 124.5, 123.5, 123.4, 119.7, 118.0, 52.2, 41.6, 34.6, 16.7, 15.5.

Ligand 4

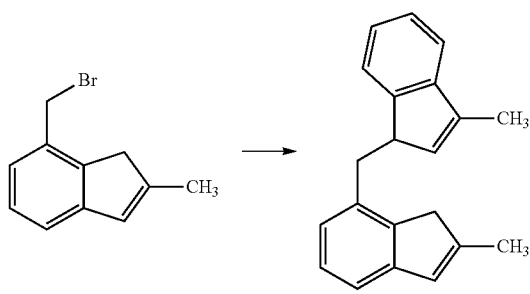

To a solution of 1.30 g (10.0 mmol) of 3-methyl-1H-indene in 90 ml of ether 4.0 ml of 2.5 M (10.0 mmol) n-BuLi in hexanes at 0° C. This mixture was stirred for 2 h at room temperature, then cooled to −80° C., a solution of 2.23 g (10.0 mmol) of 7-(bromomethyl)-2-methyl-1H-indene in 15 ml of THF was added. The resulting mixture was stirred for 12 h at room temperature, and then 1 ml of water was added. This mixture was evaporated to dryness, and 100 ml of water was added. The crude product was extracted by 3×50 ml of dichloromethane. The combined extract was dried over $Na_2SO_4$ and then evaporated to dryness. The product was isolated from the residue by flash chromatography using short column with Silica Gel 60 (40-63 um, d 60 mm, l 50 mm; eluent: hexanes). Yield 2.61 g (96%) of 3-methyl-1-[(2-methyl-1H-inden-7-yl)methyl]-1H-indene.

Anal. calc. for $C_{24}H_{20}$: C, 92.60; H, 7.40. Found: C, 92.69; H, 7.24.

$^1$H NMR ($CDCl_3$): δ 7.09-7.35 (m, 7H, 4,5,6-H in 2-methylinden-4-yl and 4,5,6,7-H in 3-methylinden-1-yl), 6.55 (m, 1H, 3-H in 2-methylinden-4-yl), 6.11 (m, 1H, 2-H in 3-methylinden-1-yl), 3.91 (m, 1-H in 3-methylinden-1-yl), 3.24 (m, 2H, 1,1'-H in 2-methylinden-4-yl), 3.15 (dd, J=13.4 Hz, J=6.8 Hz, 1H, CHH'CH), 2.66 (dd, J=13.5 Hz, J=9.9 Hz, 1H, CHH'CH), 2.18 (br.s, 3H, Me in 2-methylinden-4-yl), 2.16 (m, 3H, Me in 3-methylinden-1-yl).

Ligand 5

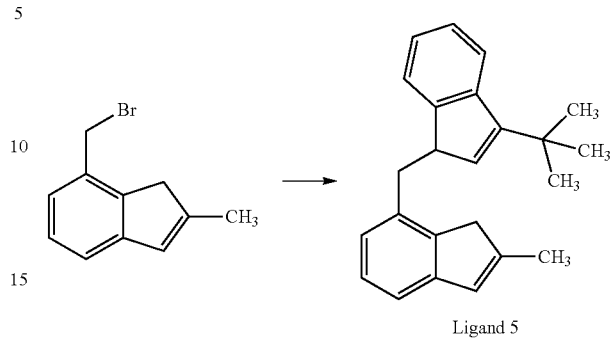

Ligand 5

To a solution of 1.72 g (10.0 mmol) of 3-tert-butyl-1H-indene in 90 ml of ether 4.0 ml of 2.5 M (10.0 mmol) n-BuLi in hexanes was added at 0° C. This mixture was stirred for 2 h at room temperature, then cooled to −80° C., and a solution of 2.23 g (10.0 mmol) of 7-(bromomethyl)-2-methyl-1H-indene in 15 ml of THF was added for 10 min. The resulting mixture was stirred for 12 h at room temperature, and then 1 ml of water was added. This mixture was evaporated to dryness, and 100 ml of water was added. The crude product was extracted with 3×50 ml of dichloromethane. The combined organic extract was dried over $Na_2SO_4$ and then evaporated to dryness. The product was isolated from the residue by flash chromatography using short column with Silica Gel 60 (40-63 um, d 60 mm, 150 mm; eluent: hexanes). Yield 2.89 g (92%) of 3-tert-butyl-1-[(2-methyl-1H-inden-7-yl)methyl]-1H-indene.

Anal. calc. for $C_{24}H_{26}$: C, 91.67; H, 8.33. Found: C, 91.75; H, 5.22.

$^1$H NMR ($CDCl_3$): δ 7.67 (m, 1H), 7.20-7.39 (m, 5H), 7.14 (m, 1H), 6.59 (m, 1H, 3-H in 2-methylinden-4-yl), 6.13 (m, 1H, 2-H in 3-tert-butylinden-1-yl), 3.75 (m, 1-H in 3-tert-butylinden-1-yl), 3.31 (s, 1H, 1-H in 2-methylinden-4-yl), 3.29 (s, 1H, 1'-H in 2-methylinden-4-yl), 3.22 (dd, J=13.4 Hz, J=6.3 Hz, 1H, CHH'CH), 2.68 (dd, J=13.5 Hz, J=9.9 Hz, 1H, CHH'CH), 2.22 (br.s, 3H, Me in 2-methylinden-4-yl), 1.41 (s, 9H, tert-Bu).

$^{13}C\{^1H\}$ NMR ($CDCl_3$): δ 152.0, 149.3, 145.9, 145.6, 143.4, 142.0, 135.4, 131.4, 127.5, 126.7, 126.0, 124.3, 124.1, 123.3, 122.2, 117.9, 48.4, 41.6, 35.8, 33.0, 29.4, 16.8.

Example 3

4-(9H-Fluoren-9-ylmethyl)-2-methyl-2,3-dihydro-1H-inden-1-yl methyl ether

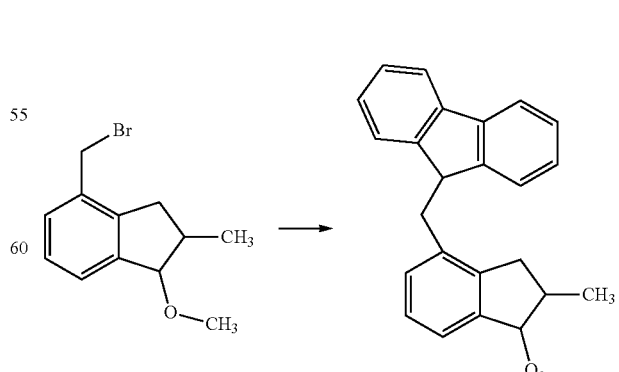

To a solution of 3.32 g (0.20 mol) of 9H-fluorene in 500 ml of ether 80 ml of 2.5 M (0.20 mol) n-BuLi in hexanes was added at 0° C. This mixture was stirred for 12 h, cooled to −80° C., and then a solution of 5.10 g (0.20 mol) of 4-(bromomethyl)-1-methoxy-2-methylindane in 150 ml of ether was added dropwise by vigorous stirring for 30 min at this temperature. The resulting mixture was stirred for 24 h at room temperature, and then 500 ml of water was added. The organic layer was separated, and the aqueous layer was extracted with 3×200 ml of dichloromethane. The combined organic extract was dried over $Na_2SO_4$ and evaporated to dryness. The product was isolated by flash chromatography on Silica Gel 60 (40-63 um, d 60 mm, l 150 mm; eluent: hexanes/ether=20/1). Yield 5.31 g (78%) of a mixture of the diastereomers A and B.

Anal. calc. for $C_{25}H_{24}O$: C, 88.20; H, 7.11. Found: C, 88.39; H, 7.00.

$^1$HNMR ($CDCl_3$): δ 7.83 (m, 4H, 4,5-H in fluorenyl of A and B), 7.09-7.46 (m, 18H, 1,2,3,6,7,8-H in fluorenyl and 5,6,7-H in indenyl of A and B), 4.66 (m, A), 4.53 (m, B), 4.27 (m, 2H, 9-H in fluorenyl of A and B), 3.57 (s, 3H, OMe of B), 3.53 (s, 3H, OMe of A), 2.30-3.17 (m, 12H, $CH_2$ bridge and 1,2,3,3'-H in indenyl of A and B), 1.19 (d, J=7.1 Hz, 3H, 2-Me in indenyl of B), 1.15 (d, J=6.8 Hz, 3H, 2-Me in indenyl of A).

$^{13}C\{^1H\}$ NMR ($CDCl_3$): δ 147.0, 146.90, 146.88, 146.85, 142.8, 142.5, 142.4, 142.3, 140.62, 140.59, 140.57, 140.54, 136.5, 136.4, 129.4, 129.2, 127.05, 127.03, 126.7, 126.6, 126.5, 126.3, 124.73, 124.67, 123.5, 123.3, 119.72, 119.71, 99.8, 91.5, 86.1, 56.7, 56.4, 47.64, 47.62, 39.4, 38.2, 37.52, 37.46, 37.0, 36.7, 19.4, 13.6.

Ligand 6

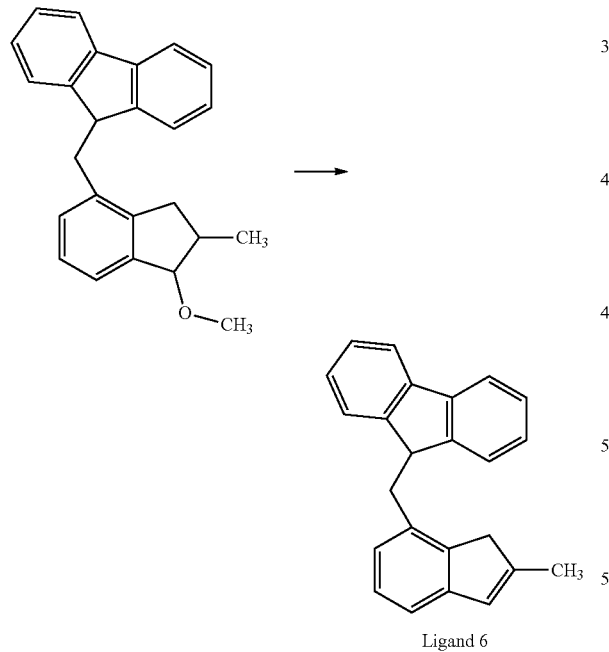

Ligand 6

To a hot (110° C.) solution of 13.8 g (40.5 mmol) of 4-(9H-fluoren-9-ylmethyl)-2-methyl-2,3-dihydro-1H-inden-1-yl methyl ether in 400 ml of toluene 1.40 g (7.36 mmol) of TsOH was added. This mixture was refluxed with a Dean-Stark trap for 40 min, and then passed through short column with Silica Gel 60 (40-63 um, d 80 mm, l 60 mm). The column was additionally washed with 500 ml of toluene. The combined elute was evaporated to dryness. The product was isolated by flash chromatography using a short column with Silica Gel 60 (40-63 um, d 60 mm, l 70 mm; eluent: hexanes/ether=35/1). Yield 12.0 g (96%) of pure 9-[(2-methyl-1H-inden-7-yl)methyl]-9H-fluorene.

Anal. calc. for $C_{24}H_2O$: C, 93.46; H, 6.54. Found: C, 93.57; H, 6.65.

$^1$H NMR ($CDCl_3$): δ 7.82 (m, 2H, 4,5-H in fluorenyl), 7.15-7.43 (m, 9H, 1,2,3,6,7,8-H in fluorenyl and 4,5,6-H in indenyl), 6.58 (m, 1H, 3-H in indenyl), 4.35 (t, J=8.0 Hz, 1H, 9-H in fluorenyl), 3.11-3.16 (m, 4H, 1,1'-H in indenyl and $CH_2$), 2.15 (s, 3H, Me).

Ligand 7

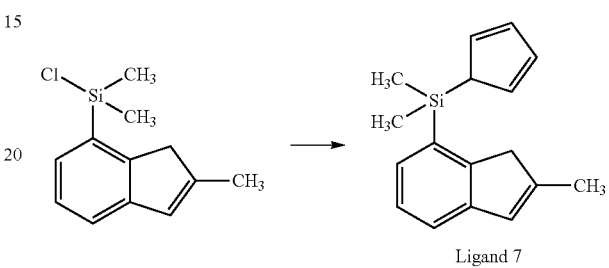

Ligand 7

To a solution of 971 mg (13.5 mmol) of CpLi in 100 ml of THF a solution of 3.0 g (13.5 mmol) of chloro(dimethyl)(2-methyl-1H-inden-7-yl)silane in 10 ml of THF was added dropwise by vigorous stirring for 5 min at −80° C. This mixture was additionally stirred for 1 h at room temperature, and 1 ml of water was added. The mixture was evaporated to dryness, and 100 ml of water was added to the residue. The crude product was extracted with 3×50 ml of dichloromethane. The combined organic extract was dried over $Na_2SO_4$ and evaporated to dryness. The product was isolated from the residue by flash chromatography using a short column with Silica Gel 60 (40-63 um, d 60 mm, l 50 mm; eluent: hexanes). Yield 2.89 g (85%) of pure cyclopenta-2,4-dien-1-yl(dimethyl)(2-methyl-1H-inden-7-yl)silane.

Anal. calc. for $C_{17}H_{20}Si$: C, 80.89; H, 7.99. Found: C, 81.12; H, 8.10.

$^1$H NMR ($CDCl_3$, 20° C.): δ 7.20-7.32 (m, 3H, 4,5,6-H in indenyl), 6.63 (br.s, 2H, 3,4-H in Cp), 6.52 (m, 1H, 3-H in indenyl), 6.47 (br.s, 2H, 2,5-H in Cp), 3.75 (br.s, 1H, 1-H in Cp), 3.38 (s, 2H, 1,1'-H in indenyl), 2.18 (s, 3H, 2-Me in indenyl), 0.22 (s, 6H, $SiMe_2$).

$^{13}C\{^1H\}$ NMR ($CDCl_3$, 20° C.): δ 148.6, 145.8, 145.3, 143.3 (br.), 133.5 (br.), 130.6 (br.), 129.2, 127.1, 125.9, 121.0, 44.2, 16.8, −1.7, −3.7.

Ligand 8

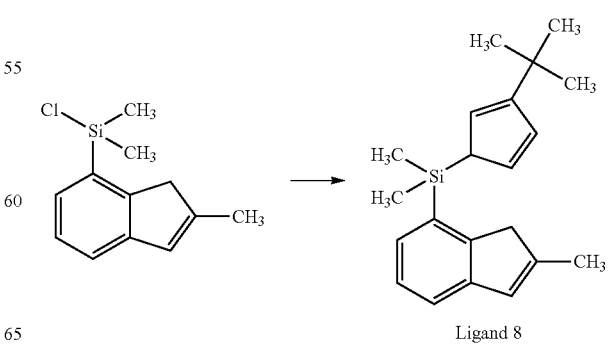

Ligand 8

To a solution of 1.22 g (10.0 mmol) of tert-butylcyclopentadiene in 100 ml of THF 4.0 ml of 2.5 M (10.0 mmol) n-BuLi in hexanes was added at −30° C. This mixture was stirred for 1 h at room temperature, and then a solution of 2.23 g (10.0 mmol) of chloro(dimethyl)(2-methyl-1H-inden-7-yl)silane in 15 ml of THF was added dropwise by vigorous stirring for 5 min at room temperature. This mixture was additionally stirred for 1 h, and 1 ml of water was added. The mixture was evaporated to dryness, and 100 ml of water was added to the residue. The crude product was extracted with 3×50 ml of dichloromethane. The combined organic extract was dried over $Na_2SO_4$ and evaporated to dryness. The product was isolated from the residue by flash chromatography using a short column with Silica Gel 60 (40-63 um, d 60 mm, l 50 mm; eluent: hexanes). Yield 2.56 g (83%) of pure (3-tert-butylcyclopenta-2,4-dien-1-yl)(dimethyl)(2-methyl-1H-inden-7-yl)silane.

Anal. calc. for $C_{21}H_{28}Si$: C, 81.75; H, 9.15. Found: C, 81.67; H, 9.30.

$^1$H NMR ($CDCl_3$, 20° C.): δ 7.24-7.34 (m, 3H, 4,5,6-H in indenyl), 6.68 (br.m, 1H, 4-H in Cp), 6.55 (m, 1H, 3-H in indenyl), 6.46 (br.m, 1H, 5-H in Cp), 6.07 (br.s, 1H, 2-H in Cp), 3.65 (br.s, 1H, 1-H in Cp), 3.41 (br.s, 2H, 1,1'-H in indenyl), 2.21 (s, 3H, 2-Me in indenyl), 1.20 (s, 9H, tert-Bu), 0.26 (s, 6H, $SiMe_2$).

Ligand 9

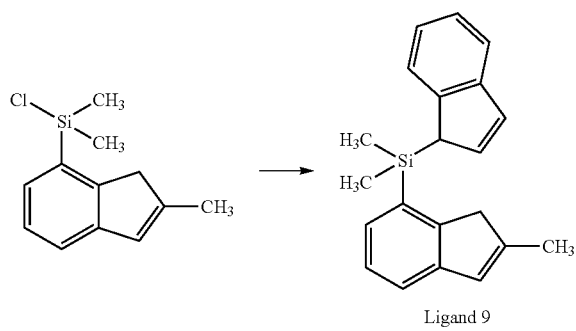 [SMILES: CC1=Cc2cccc([Si](C)(C)Cl)c2C1 ; CC1=Cc2cccc([Si](C)(C)C3C=Cc4ccccc43)c2C1]

Ligand 9

To a solution of 1.29 g (10.0 mmol, 90% purity) of 1H-indene in 90 ml of ether 4.0 ml of 2.5M (10.0 mmol) n-BuLi in hexanes was added at 0° C. This mixture was stirred for 12 h at room temperature, cooled to −30° C., and 449 mg (5.0 mmol) of CuCN was added. The resulting mixture was stirred for 1 h at this temperature, cooled to −80° C., and a solution of 2.23 g (10.0 mmol) of chloro(dimethyl)(2-methyl-1H-inden-7-yl)silane in 15 ml of ether was added dropwise by vigorous stirring for 10 min. This mixture was stirred for 12 h at room temperature, and then 1 ml of water was added. The mixture was stirred for 5 min and passed through short column with Silica Gel 60 (40-63 um, d 50 mm, l 30 mm). The silica gel layer was additionally washed by 100 ml of ether. The combined elute was evaporated to dryness. The product was isolated from the residue by flash chromatography using a short column with Silica Gel 60 (40-63 um, d 60 mm, l 50 mm; eluent: hexanes). Yield 2.69 g (89%) of 1H-inden-1-yl(dimethyl)(2-methyl-1H-inden-7-yl)silane.

Anal. calc. for $C_{24}H_{22}Si$: C, 83.38; H, 7.33. Found: C, 83.51; H, 7.45.

$^1$H NMR ($CDCl_3$): δ 7.48-7.05 (m, 7H, 4,5,6,7-H in indenyl and 4,5,6-H in 2-methylindenyl), 6.92 (m, 1H, 3-H in indenyl), 6.57 (m, 1H, 3-H in 2-methylindenyl), 6.54 (m, 1H, 2-H in indenyl), 3.88 (m, 1H, 1-H in indenyl), 3.31 (m, 2H, 1,1'-H in 2-methylindenyl), 2.17 (s, 3H, 2-Me in 2-methylindenyl), 0.20 (s, 3H, SiMeMe'), 0.16 (s, 3H, SiMeMe').

$^{13}C\{^1H\}$ NMR ($CDCl_3$): δ 148.8, 145.9, 145.3, 144.8, 144.3, 135.6, 131.8, 129.5, 129.3, 127.1, 125.8, 124.9, 123.6, 123.0, 121.1, 120.9, 45.4, 44.2, 16.7, −3.9, −4.3.

Ligand 10

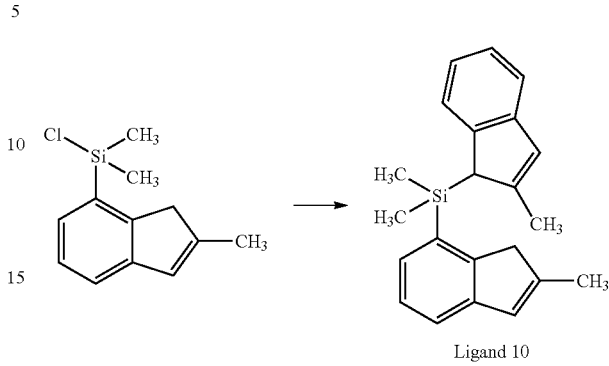

Ligand 10

To a solution of 1.30 g (10.0 mmol) of 2-methyl-1H-indene in 90 ml of ether 4.0 ml of 2.5M (10.0 mmol) n-BuLi in hexanes was added at 0° C. This mixture was stirred for 12 h at room temperature, cooled to −50° C., and 449 mg (5.0 mmol) of CuCN was added. The resulting mixture was stirred for 1 h at −30° C., cooled to −80° C., and a solution of 2.23 g (10.0 mmol) of chloro(dimethyl)(2-methyl-1H-inden-7-yl)silane in 15 ml of ether was added dropwise by vigorous stirring for 10 min. This mixture was stirred for 12 h at room temperature, and then 1 ml of water was added. The mixture was stirred for 5 min and passed through short column with Silica Gel 60 (40-63 um, d 50 mm, l 30 mm). The silica gel layer was additionally washed by 100 ml of ether. The combined elute was evaporated to dryness. The product was isolated from the residue by flash chromatography using a short column with Silica Gel 60 (40-63 um, d 60 mm, l 50 mm; eluent: hexanes). Yield 2.79 g (88%) of dimethyl(2-methyl-1H-inden-1-yl)(2-methyl-1H-inden-7-yl)silane.

Anal. calc. for $C_{22}H_{24}Si$: C, 83.48; H, 7.64. Found: C, 83.20; H, 7.77.

$^1$H NMR ($CDCl_3$): δ 7.15-7.37 (m, 5H, 4,5,7-H in 2-methylinden-1-yl and 4,6-H in 2-methylinden-4-yl), 6.90-6.99 (m, 2H, 6-H in 2-methylinden-1-yl and 5-H in 2-methylinden-4-yl), 6.56 (m, 1H, 3-H in 2-methylinden-4-yl), 6.54 (m, 1H, 3-H in 2-methylinden-1-yl), 3.72 (s, 1H, 1-H in 2-methylinden-1-yl), 3.24 (m, 2H, 1,1'-H in 2-methylinden-4-yl), 2.17 (s, 3H, Me in 2-methylinden-4-yl), 1.98 (s, 3H, Me in 2-methylinden-1-yl), 0.24 (s, 3H, SiMeMe'), 0.23 (s, 3H, SiMeMe').

$^{13}C\{^1H\}$ NMR ($CDCl_3$): δ 148.9, 147.6, 145.8, 145.2, 145.0, 144.7, 131.9, 129.6, 127.0, 125.82, 125.78, 124.8, 123.0, 122.3, 121.1, 119.6, 48.0, 44.1, 17.3, 16.7, −3.7, −4.0.

Ligand 11

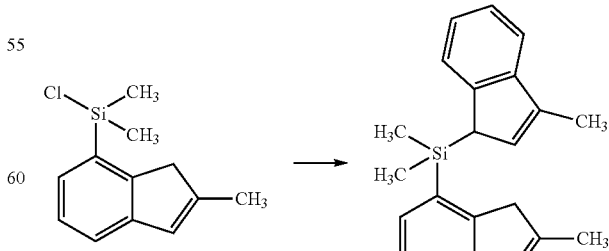

Ligand 11

To a solution of 1.30 g (10.0 mmol) of 3-methyl-1H-indene in 90 ml of ether 4.0 ml of 2.5M (10.0 mmol) n-BuLi in hexanes was added at 0° C. This mixture was stirred for 12 h at room temperature, cooled to −50° C., and 449 mg (5.0 mmol) of CuCN was added. The resulting mixture was stirred for 1 h at −30° C., cooled to −80° C., and a solution of 2.23 g (10.0 mmol) of chloro(dimethyl)(2-methyl-1H-inden-7-yl) silane in 15 ml of ether was added dropwise by vigorous stirring for 10 min. This mixture was stirred for 12 h at room temperature, and then 1 ml of water was added. The mixture was stirred for 5 min and passed through short column with Silica Gel 60 (40-63 um, d 50 mm, l 30 mm). The silica gel layer was additionally washed by 100 ml of ether. The combined elute was evaporated to dryness. The product was isolated from the residue by flash chromatography using a short column with Silica Gel 60 (40-63 um, d 60 mm, l 50 mm; eluent: hexanes). Yield 2.85 g (90%) of dimethyl(2-methyl-1H-inden-7-yl)(3-methyl-1H-inden-1-yl)silane.

Anal. calc. for $C_{22}H_{24}Si$: C, 83.48; H, 7.64. Found: C, 83.62; H, 7.75.

$^1$H NMR (CDCl$_3$): δ 7.16-7.50 (m, 7H, 4,5,6,7-H in 3-methylinden-1-yl and 4,5,6-H in 2-methylinden-4-yl), 6.62 (m, 1H, 3-H in 3-methylinden-1-yl), 6.32 (m, 1H, 3-H in 2-methylinden-4-yl), 3.84 (m, 1H, 1-H in 3-methylinden-1-yl), 3.40 (m, 2H, 1,1'-H in 2-methylinden-4-yl), 2.29 (s, 3H, Me in 3-methylinden-1-yl), 2.26 (s, 3H, Me in 2-methylinden-4-yl), 0.26 (s, 3H, SiMeMe'), 0.24 (s, 3H, SiMeMe').

$^{13}C\{^1H\}$ NMR (CDCl$_3$): δ 148.8, 145.7, 145.4, 145.31, 145.25, 137.4, 132.1, 130.5, 129.6, 127.1, 125.8, 124.7, 123.6, 122.9, 121.0, 118.8, 44.2, 43.3, 16.7, 12.9, −3.8, −4.2. Ligand 12

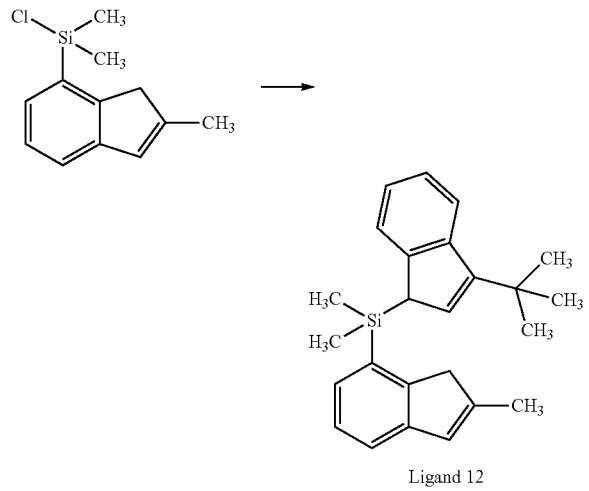

Ligand 12

To a solution of 1.72 g (10.0 mmol) of 3-tert-butyl-1H-indene in 90 ml of ether 4.0 ml of 2.5M (10.0 mmol) n-BuLi in hexanes was added at 0° C. This mixture was stirred for 12 h at room temperature, cooled to −50° C., and 449 mg (5.0 mmol) of CuCN was added. The resulting mixture was stirred for 1 h at −30° C., cooled to −80° C., and a solution of 2.23 g (10.0 mmol) of chloro(dimethyl)(2-methyl-1H-inden-7-yl) silane in 15 ml of ether was added dropwise by vigorous stirring for 10 min. This mixture was stirred for 12 h at room temperature, and then 1 ml of water was added. The mixture was stirred for 5 min and passed through short column with Silica Gel 60 (40-63 um, d 50 mm, l 30 mm). The silica gel layer was additionally washed by 100 ml of ether. The combined elute was evaporated to dryness. The product was isolated from the residue by flash chromatography using a short column with Silica Gel 60 (40-63 um, d 60 mm, l 50 mm; eluent: hexanes). Yield 2.90 g (81%) of (3-tert-butyl-1H-inden-1-yl)(dimethyl)(2-methyl-1H-inden-7-yl)silane.

Anal. calc. for $C_{25}H_{30}Si$: C, 83.74; H, 8.43. Found: C, 83.90; H, 8.59.

$^1$H NMR (CDCl$_3$): δ 7.68-7.72 (m, 1H, 7-H in 3-tert-butylinden-1-yl), 7.10-7.38 (m, 6H, 4,5,6-H in 3-tert-butyl-inden-1-yl and 4,5,6-H in 2-methylinden-4-yl), 6.56 (m, 1H, 3-H in 2-methylinden-1-yl), 6.26 (d, J=2.0 Hz, 1H, 3-H in 3-tert-butylinden-1-yl), 3.75 (m, 1H, 1-H in 3-tert-butylinden-1-yl), 3.26 (m, 2H, 1,1'-H in 2-methylinden-4-yl), 2.20 (s, 3H, Me), 1.39 (s, 9H, tert-butyl), 0.28 (s, 3H, SiMeMe'), 0.24 (s, 3H, SiMeMe').

$^{13}C\{^1H\}$ NMR (CDCl$_3$): δ 151.0, 148.9, 146.7, 145.7, 145.2, 143.1, 131.7, 129.5, 127.8, 127.0, 125.7, 124.2, 123.4, 123.0, 122.0, 121.0, 44.2, 43.0, 33.1, 29.7, 16.7, −3.7, −3.8. Ligand 13

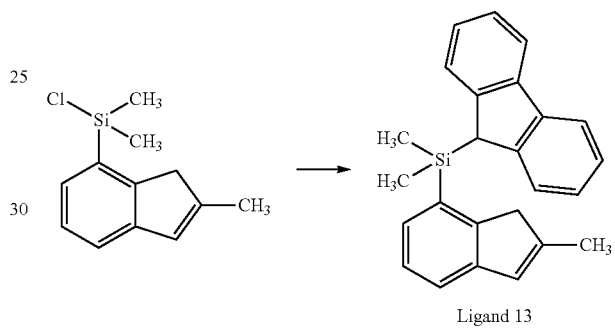

Ligand 13

To a solution of 1.66 g (10.0 mmol) of 9H-fluorene in 90 ml of ether 4.0 ml of 2.5M (10.0 mmol) n-BuLi in hexanes was added at 0° C. This mixture was stirred for 12 h at room temperature, cooled to −50° C., and 449 mg (5.0 mmol) of CuCN was added. The resulting mixture was stirred for 1 h at −30° C., cooled to −80° C., and a solution of 2.23 g (10.0 mmol) of chloro(dimethyl)(2-methyl-1H-inden-7-yl)silane in 15 ml of ether was added dropwise by vigorous stirring for 10 min. This mixture was stirred for 12 h at room temperature, and then 1 ml of water was added. The mixture was stirred for 5 min and passed through short column with Silica Gel 60 (40-63 um, d 50 mm, l 30 mm). The silica gel layer was additionally washed by 100 ml of ether. The combined elute was evaporated to dryness. The product was isolated from the residue by flash chromatography using a short column with Silica Gel 60 (40-63 um, d 60 mm, l 50 mm; eluent: hexanes). Yield 3.24 g (92%) of 9H-fluoren-9-yl(dimethyl)(2-methyl-1H-inden-7-yl)silane.

Anal. calc. for $C_{25}H_{24}Si$: C, 85.17; H, 6.86. Found: C, 85.31; H, 7.03.

$^1$H NMR (CDCl$_3$): δ 7.82-7.86 (m, 2H, 4,5-H in fluorenyl), 7.07-7.41 (m, 9H, 1,2,3,6,7,8-H in fluorenyl and 4,5,6-H in indenyl), 6.54 (m, 1H, 3-H in indenyl), 4.18 (m, 1H, 9-H in fluorenyl), 3.18 (m, 1,1'-H in indenyl), 2.15 (m, 3H, 2-Me in indenyl), 0.12 (s, 6H, SiMe$_2$).

$^{13}C\{^1H\}$ NMR (CDCl$_3$): δ 149.2, 145.9, 145.3, 145.1, 143.2, 140.5, 131.3, 129.9, 127.0, 126.70, 126.67, 125.9, 125.8, 125.3, 125.0, 124.2, 124.1, 121.2, 119.9, 119.8, 44.2, 41.6, 36.9, 16.7, −4.2.

Ligand 14

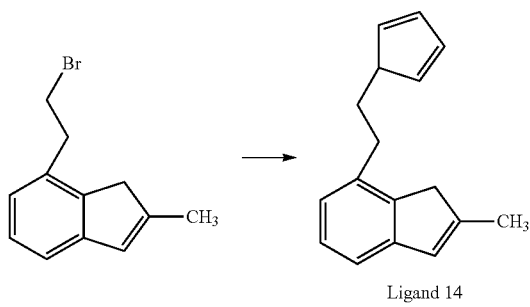

Ligand 14

To a solution of 2.61 g (36.2 mmol) of CpLi in 170 ml of ТГФ a solution of 8.58 g (36.2 mmol) of 4/7-(2-bromoethyl)-2-methyl-1H-indene in 10 ml of THF was added dropwise by vigorous stirring for 10 min at −80° C. This mixture was stirred for 12 h at room temperature, and then 1 ml of water was added. The resulting mixture was evaporated to dryness, and 100 ml of water was added to the residue. The crude product was extracted by 3×50 ml of dichloromethane. The combined organic extract was dried over $Na_2SO_4$ and evaporated to dryness. The product was isolated by flash chromatography using a short column with Silica Gel 60 (40-63 um, d 80 mm, l 60 mm; eluent: hexanes. Yield 5.96 g (74%) of a mixture of isomeric compounds.

Anal. calc. for $C_{17}H_{18}$: C, 91.84; H, 8.16. Found: C, 91.69; H, 8.02.

$^1$H NMR (CDCl$_3$): δ 6.98-7.33 (m), 6.68 (m), 6.54 (m), 6.32 (m), 6.14 (m), 3.67 (m), 3.26-3.40 (m), 2.92-3.07 (m), 2.79 (m), 2.37 (m), 2.23 (m), 1.51 (m), 1.35 (m), 0.96 (m).

Ligand 15

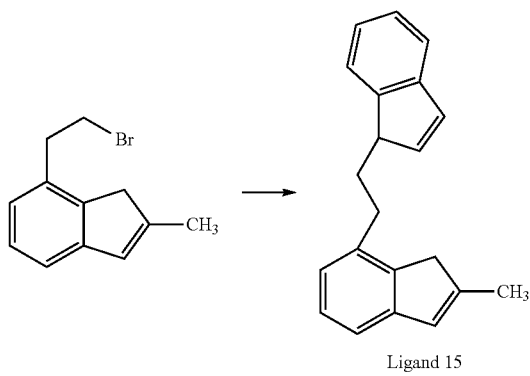

Ligand 15

To a solution of 4.54 g (35.2 mmol, 90% purity) of 1H-indene in 175 ml of ТГФ a solution 14.1 ml of 2.5 M (35.3 mmol) of n-BuLi in hexanes was added for 5 min at 0° C. This mixture was stirred for 1 h at this temperature, cooled to −30° C., and a solution of 8.35 g (35.2 mmol) of 4/7-(2-bromoethyl)-2-methyl-1H-indene in 10 ml of THF was added dropwise by vigorous stirring for 10 min at this temperature. This mixture was stirred for 12 h at room temperature, and then 1 ml of water was added. The resulting mixture was evaporated to dryness, and 100 ml of water was added to the residue. The crude product was extracted by 3×50 ml of dichloromethane. The combined organic extract was dried over $Na_2SO_4$ and evaporated to dryness. The product was isolated by flash chromatography on Silica Gel 60 (40-63 um, d 60 mm, l 300 mm; eluent: hexanes). Yield 6.13 g (64%) of 7-[2-(1H-inden-1-yl)ethyl]-2-methyl-1H-indene.

Anal. calc. for $C_{21}H_{20}$: C, 92.60; H, 7.40. Found: C, 92.45; H, 7.22.

$^1$H NMR (CDCl$_3$): δ 7.04-7.54 (m, 7H, 4,5,6,7-H in indenyl and 4,5,6-H in 2-methylindenyl), 6.65 (m, 1H, 3-H in indenyl), 6.55 (m, 1H, 3-H in 2-methylindenyl), 6.30 (m, 1H, 2-H in indenyl), 3.06-3.41 (m, 7H, 1-H in indenyl and 1,1'-H in 2-methylindenyl and CH$_2$CH$_2$), 2.20 (s, 3H, Me).

Ligand 16

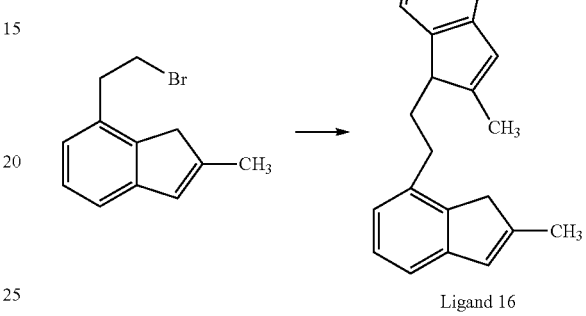

Ligand 16

To a solution of 4.58 g (35.2 mmol) of 2-methyl-1H-indene in 175 ml of ТГФ a solution 14.1 ml of 2.5 M (35.3 mmol) of n-BuLi in hexanes was added for 5 min at room temperature. This mixture was stirred for 1 h at this temperature, cooled to −70° C., and a solution of 8.35 g (35.2 mmol) of 4/7-(2-bromoethyl)-2-methyl-1H-indene in 10 ml of THF was added dropwise by vigorous stirring for 10 min at this temperature. This mixture was stirred for 12 h at room temperature, and then 1 ml of water was added. The resulting mixture was evaporated to dryness, and 100 ml of water was added to the residue. The crude product was extracted by 3×50 ml of dichloromethane. The combined organic extract was dried over $Na_2SO_4$ and evaporated to dryness. The product was isolated by flash chromatography on Silica Gel 60 (40-63 um, d 60 mm, l 300 mm; eluent: hexanes). Yield 5.54 g (55%) of 2-methyl-1-[2-(2-methyl-1H-inden-7-yl)ethyl]-1H-indene.

Anal. calc. for $C_{22}H_{22}$: C, 92.26; H, 7.74. Found: C, 92.01; H, 7.60.

$^1$H NMR (CDCl$_3$): δ 7.17-7.61 (m, 7H, 4,5,6,7-H in 2-methylinden-1-yl and 4,5,6-H in 2-methylinden-4-yl), 6.67-6.74 (m, 2H, 3-H in both 2-methylindenyls), 2.98-3.49 (m, 7H, 1-H in 2-methylinden-1-yl and 1,1'-H in 2-methylinden-4-yl and CH$_2$CH$_2$), 2.08 (s, 3H, Me in 2-methylinden-4-yl), 2.04 (s, 3H, Me in 2-methylinden-1-yl).

Ligand 17

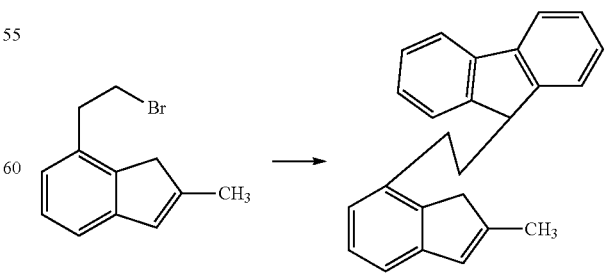

Ligand 17

To a solution of 5.85 g (35.2 mmol) of 9H-fluorene in 175 ml of ТГФ a solution 14.1 ml of 2.5 M (35.3 mmol) of n-BuLi in hexanes was added for 5 min at room temperature. This mixture was stirred for 5 h at this temperature, cooled to −80° C., and a solution of 8.35 g (35.2 mmol) of 4/7-(2-bromoethyl)-2-methyl-1H-indene in 10 ml of THF was added dropwise by vigorous stirring for 10 min at this temperature. This mixture was stirred for 24 h at room temperature, and then 1 ml of water was added. The resulting mixture was evaporated to dryness, and 100 ml of water was added to the residue. The crude product was extracted by 3×50 ml of dichloromethane. The combined organic extract was dried over $Na_2SO_4$ and evaporated to dryness. The product was isolated by flash chromatography on Silica Gel 60 (40-63 um, d 60 mm, l 300 mm; eluent: hexanes). Yield 7.82 g (69%) of a ca. 1 to 1 mixture of 9-[2-(2-methyl-1H-inden-7-yl)ethyl]-9H-fluorene (A) and 9-[2-(2-methyl-1H-inden-4-yl)ethyl]-9H-fluorene (B).

Anal. calc. for $C_{25}H_{22}$: C, 93.12; H, 6.88. Found: C, 93.00; H, 6.69.

$^1$H NMR (CDCl$_3$): δ 6.98-7.94 (m, 22H, 4,5,6-H in indenyl of A and 5,6,7-H in indenyl of B and 1,2,3,4,5,6,7,8-H in fluorenyl of both isomers), 6.58 (m, 1H, 3-H in indenyl of B), 6.52 (m, 1H, 3-H in indenyl of A), 4.22 (m, 2H, 9-H in fluorenyl of both isomers), 3.37 (m, 2H, 1,1'-H in indenyl of A), 3.16 (m, 2H, 1,1'-H in indenyl of B), 2.51 (m, 8H, $CH_2CH_2$ of both isomers), 2.26 (s, 3H, Me of A), 2.24 (s, 3H, Me of B).

Example 4

2-[(2-Methyl-1H-inden-4/7-yl)methyl]indan-1-one

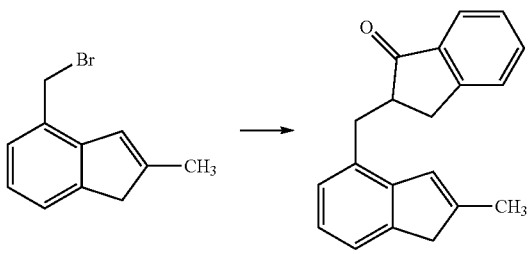 [SMILES: CC1=Cc2c(CBr)cccc2C1 ; CC1=Cc2c(cccc2CC2Cc3ccccc3C2=O)C1]

To a solution of 24.5 g (242 mmol) of diisopropylamine in 800 ml of THF 96.8 ml of 2.5 M (242 mmol) n-BuLi was added at vigorous stirring for 15 min at −80° C. This mixture was stirred for 1 h at −30° C. and then evaporated to dryness. To a solution of the residue in 800 ml of THF a solution of 32.0 g (242 mmol) of indanone-1 in 200 ml of THF was added dropwise at vigorous stirring for 20 min at −30° C. The resulting mixture was stirred for 1 h at this temperature, and a solution of 27.0 g (121 mmol) of 4/7-(bromomethyl)-2-methyl-1H-indene in 200 ml of THF was added for 15 min. This mixture was stirred for 24 h at room temperature, and 10 ml of water was added. The resulting mixture was evaporated to dryness. A solution of the residue in 500 ml of ether was washed by 1 liter of water. The organic layer was separated, and the aqueous layer was washed by 3×200 ml of ether. The product was isolated by flash chromatography on Silica Gel 60 (40-63 um, d 60 mm, l 400 mm; eluent: hexanes/ether=10/1). Yield 9.30 g (28%).

Anal. calc. for $C_{20}H_{18}O$: C, 87.56; H, 6.61. Found: C, 87.65; H, 6.73.

$^1$H NMR (CDCl$_3$): δ 7.80 (m, 1H), 7.67 (m, 1H), 7.34-7.42 (m, 2H), 7.18 (m, 1H), 7.15 (m, 1H), 6.98 (m, 1H), 6.50 (m, 1H), 3.45 (m, 1H), 3.47 (m, 1H), 3.28 (s, 2H), 3.19 (m, 1H), 3.08 (m, 1H), 2.85 (m, 1H), 2.64 (m, 1H), 2.15-2.17 (m, 6H).

Ligand 18

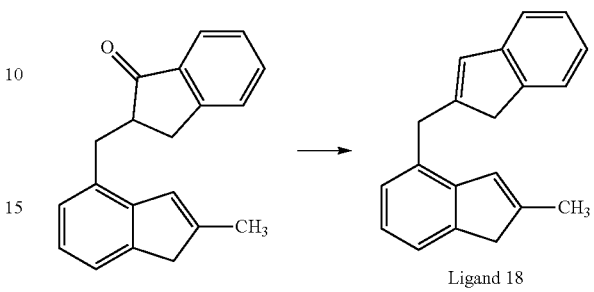

Ligand 18

To a solution of 9.30 g (33.9 mmol) of 2-[(2-methyl-1H-inden-4/7-yl)methyl]indan-1-one in 60 ml of THF-methanol (2:1, vol.) 2.78 g (74.1 mmol) of $NaBH_4$ was added in small portions for 2 hours at rt. The mixture was stirred for 12 h at ambient temperature and then poured on 100 cm$^3$ of ice. The organic layer was separated, the aqueous layer was extracted with 3×300 ml of methyl-tert-butyl ether. The combined extract was dried over $K_2CO_3$ and evaporated to dryness. To the yellowish oil obtained 1250 ml of toluene was added. This toluene solution was treated with a catalytic amount of TsOH (ca. 280 mg) for 45 min at reflux using a Dean-Stark trap. The resulting mixture was passed through a short column with Silica Gel 60 (40-63 μm, d 50 mm, l 30 mm). This column was additionally eluted with 200 ml of toluene. The product was isolated from the combined elute using flash chromatography on Silica Gel 60 (40-63 um, d 60 mm, l 150 mm; eluent: hexanes). Yield 8.23 g (94%) of a mixture of isomeric indenes.

Anal. calc. for $C_{20}H_{18}$: C, 92.98; H, 7.02. Found: C, 92.79; H, 7.11. 1H NMR (CDCl$_3$): δ 7.17-7.56 (m, 7H), 6.67-6.84 (m, 2H), 3.93-4.12 (m, 2H), 3.41-3.51 (m, 4H), 2.32-2.37 (m, 3H).

Complex 1-Zr

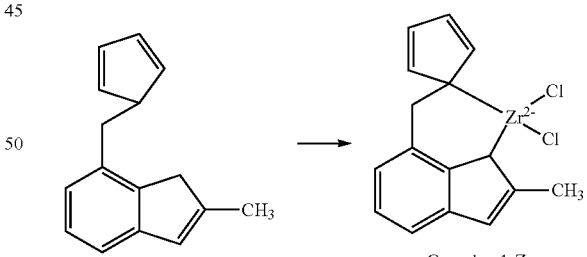

Complex 1-Zr

To a solution of 2.08 g (10.0 mmol) of ligand 1 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10.0 mmol) of $ZrCl_4(THF)_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 30 ml of toluene. Crystals precipitated at −30° C. were collected, washed by 3×3 ml of cold toluene, 2×10 ml of hexanes, and dried in vacuum. Yield 1.69 g (46%).

Anal. calc. for $C_{16}H_{14}Cl_2Zr$: C, 52.16; H, 3.83. Found: C, 52.30; H, 4.01.

$^1$H NMR (CD$_2$Cl$_2$): δ 7.44 (m, 1H, 4-H in indenyl), 7.23 (m, 1H, 5-H in indenyl), 6.82 (m, 1H, 6-H in indenyl), 6.62 (m, 1H, 3/4-H in Cp), 6.43 (m, 1H, 1/3-H in indenyl), 6.28 (m, 1H, 3/1-H in indenyl), 6.16 (m, 1H, 2/5-H in Cp), 6.13 (m, 1H, 4/3-H in Cp), 4.69 (m, 1H, 5/2-H in Cp), 4.15 (d, J=13.4 Hz, 1H, CHH'), 3.89 (d, J=13.4 Hz, CHH'), 2.35 (s, 3H, Me).

$^{13}$C{$^1$H} NMR (CD$_2$Cl$_2$): δ 145.2, 139.2, 129.4, 129.1, 122.9, 122.8, 120.9, 120.1, 118.1, 116.9 (2C), 111.4, 109.4, 99.5, 34.0, 18.0.

Complex 3-Zr

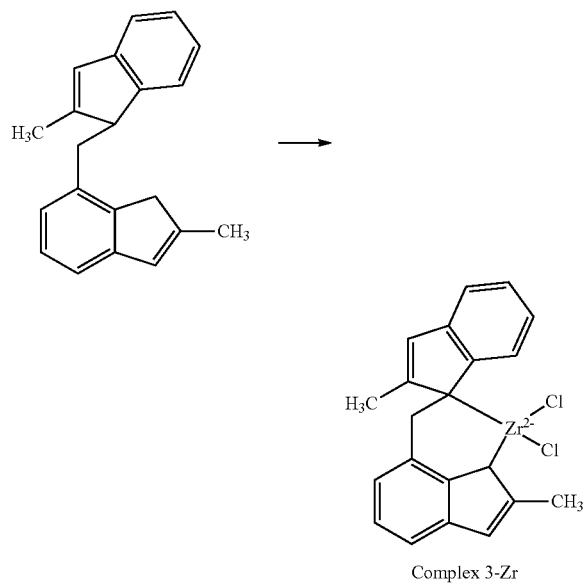

Complex 3-Zr

To a solution of 3.02 g (10.0 mmol) of ligand 3 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10.0 mmol) of ZrCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness. The product was extracted from the residue by 2×10 ml of toluene. The combined extract was evaporated to dryness, the residue was washed by 2×5 ml of hexanes and dried in vacuum. Yield 951 mg (22%) of pure meso-like complex.

Anal. calc. for $C_{21}H_{18}Cl_2Zr$: C, 58.32; H, 4.19. Found: C, 58.58; H, 4.25.

$^1$H NMR (CD$_2$Cl$_2$): δ 7.37 (m, 1H), 7.24-7.33 (m, 2H), 7.05-6.97 (m, 2H), 6.88-6.77 (m, 2H), 6.63 (s, 1H, 3-H in inden-4-yl), 6.38 (d, J=2.2 Hz, 1H, 1/3-H in inden-2-yl), 5.96 (d, J=2.2 Hz, 1H, 3/1-H in inden-2-yl), 4.50 (d, J=14.1 Hz, 1H), 4.23 (d, J=14.1 Hz, 1H), 2.58 (s, 3H, Me), 2.29 (s, 3H, Me).

Complex 3-Hf

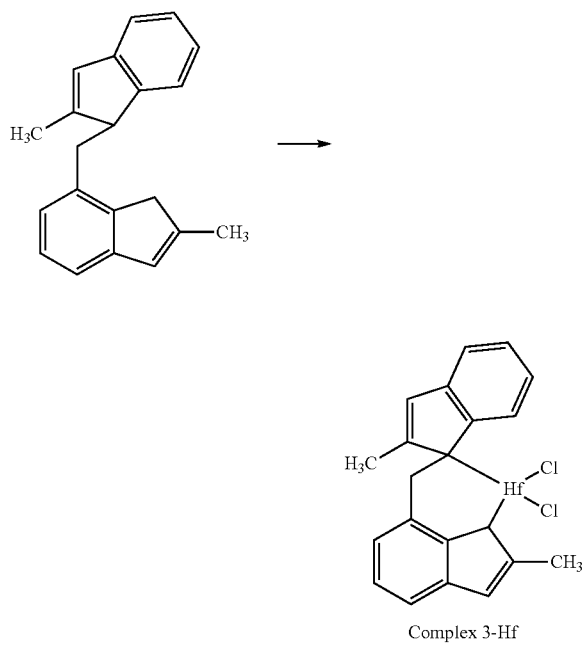

Complex 3-Hf

To a solution of 3.02 g (10.0 mmol) of ligand 3 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 4.64 g (10.0 mmol) of HfCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was washed by 5×4 ml of cold toluene, 2×10 ml of hexanes, and dried in vacuum. Yield 1.09 g (21%) of a ca. 9 to 1 mixture of rac- and meso-like isomeric complexes.

Anal. calc. for $C_{21}H_{18}Cl_2Hf$: C, 48.53; H, 3.49. Found: C, 48.60; H, 3.57.

$^1$H NMR (CD$_2$Cl$_2$): δ 7.83 (m, 1H), 7.54 (m, 1H), 7.37 (m, 1H), 7.20-7.28 (m, 2H), 7.15 (m, 1H), 6.94 (m, 1H), 6.10 (d, J=1.8 Hz, 1H, 1/3-H in inden-2-yl), 6.05 (s, 1H, 3-H in inden-4-yl), 5.89 (d, J=1.8 Hz, 1H, 3/1-H in inden-2-yl), 4.63 (d, J=14.4 Hz, 1H), 3.99 (d, J=14.4 Hz, 1H), 1.97 (s, 3H, Me), 1.66 (s, 3H, Me).

Complex 4-Zr

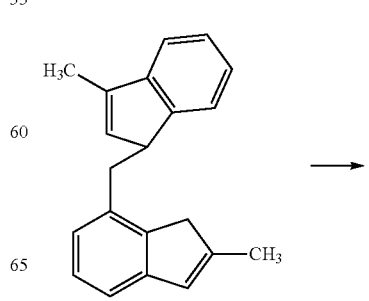

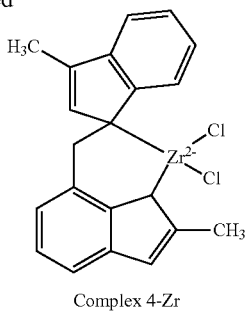

Complex 4-Zr

To a solution of 3.02 g (10.0 mmol) of ligand 4 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of $ZrCl_4(THF)_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 30 ml of toluene. Crystals precipitated at −30° C. were collected, washed by 2×3 ml of cold toluene, 3×10 ml of hexanes, and dried in vacuum. Yield 2.72 g (63%) of a ca. 4 to 3 mixture of rac- and meso-like complexes.

Anal. calc. for $C_{21}H_{18}Cl_2Zr$: C, 58.32; H, 4.19. Found: C, 58.44; H, 4.31.

$^1$H NMR ($CD_2Cl_2$): major isomer, δ 7.78-6.76 (m, 7H), 6.28 (m, 1H), 6.10 (m, 1H), 4.75 (s, 1H), 4.83 (d, J=13.8 Hz, 1H), 3.99 (d, J=13.8 Hz, 1H), 2.23 (s, 3H, Me), 1.97 (s, 3H, Me); minor isomer, δ 7.78-6.76 (m, 7H), 6.35 (m, 1H), 6.28 (m, 1H), 6.25 (s, 1H), 4.46 (d, J=14.0 Hz, 1H), 4.32 (d, J=14.0 Hz, 1H), 2.47 (s, 3H, Me), 2.28 (s, 3H, Me).
Complex 5-Zr

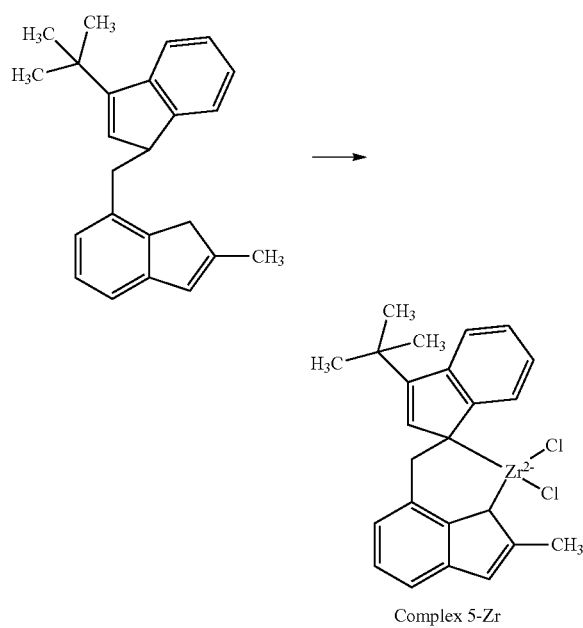

Complex 5-Zr

To a solution of 3.45 g (10.0 mmol) of ligand 5 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of $ZrCl_4(THF)_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was washed by 500 ml of hexanes. Crystals precipitated at −30° C. were collected, washed by 3×3 ml of cold hexanes, and dried in vacuum. Yield 2.66 g (56%) of a ca. 5 to 4 mixture of rac- and meso-like complexes.

Anal. calc. for $C_{24}H_{24}Cl_2Zr$: C, 60.74; H, 5.10. Found: C, 60.62; H, 5.35.

$^1$H NMR ($CD_2Cl_2$): major isomer, δ 7.45-6.73 (m, 7H), 6.25 (m, 1H), 6.11 (m, 1H), 5.05 (s, 1H), 4.61 (d, J=13.9 Hz, 1H), 4.00 (d, J=13.9 Hz, 1H), 1.94 (s, 3H, Me), 1.33 (s, 9H, tert-Bu); minor isomer, 7.45-6.73 (m, 7H), 6.55 (s, 1H), 6.41 (m, 1H), 6.34 (m, 1H), 4.48 (d, J=14.1 Hz, 1H), 4.29 (d, J=14.1 Hz, 1H), 2.27 (s, 3H, Me), 1.51 (s, 9H, tert-Bu).
Complex 6-Zr

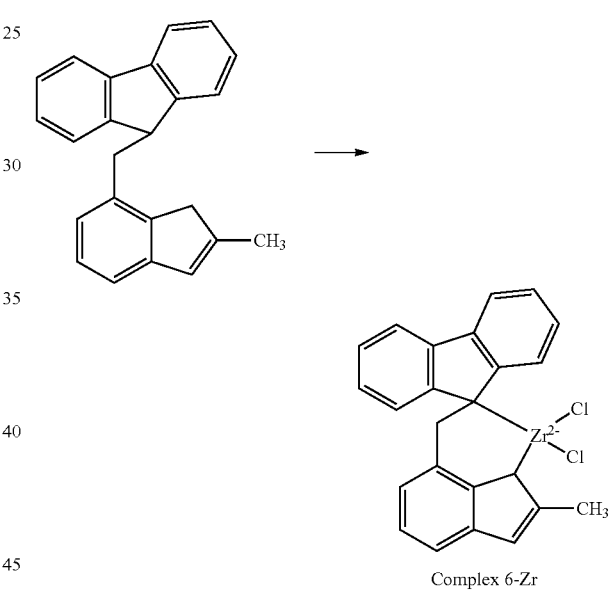

Complex 6-Zr

To a solution of 3.08 g (10.0 mmol) of ligand 6 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of $ZrCl_4(THF)_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 100 ml of toluene. Crystals precipitated at −30° C. were collected, washed by 2×5 ml of cold toluene, 2×10 ml of hexanes, and dried in vacuum. Yield 2.53 g (54%).

Anal. calc. for $C_{24}H_{18}Cl_2Zr$: C, 61.52; H, 3.87. Found: C, 61.79; H, 4.00.

$^1$H NMR ($CD_2Cl_2$): δ 8.03-6.97 (m, 11H), 6.22 (m, 1H), 6.16 (m, 1H), 4.98 (d, J=14.3 Hz, 1H), 4.42 (d, J=14.3 Hz, 1H), 1.88 (s, 3H, Me).

Complex 7-Zr

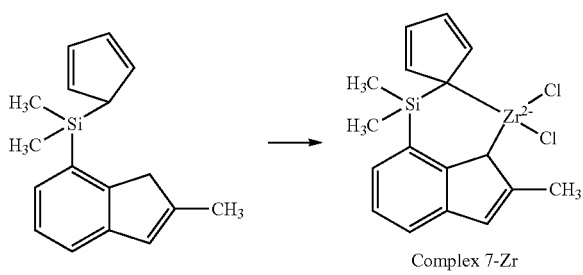

Complex 7-Zr

To a solution of 2.52 g (10.0 mmol) of ligand 7 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of ZrCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 100 ml of toluene. Crystals precipitated at −30° C. were collected, washed by 3×7 ml of cold toluene, 2×10 ml of hexanes, and dried in vacuum. Yield 949 mg (23%).

Anal. calc. for C$_{17}$H$_{18}$Cl$_2$SiZr: C, 49.49; H, 4.40. Found: C, 49.66; H, 4.52.

$^1$H NMR (CD$_2$Cl$_2$): δ 7.96 (m, 1H, 7-H in indenyl), 7.30 (dd, J=8.3 Hz, J=6.6 Hz, 6-H in indenyl), 7.14 (dd, J=6.6 Hz, J=1.0 Hz, 5-H in indenyl), 6.87 (m, 1H, C$_5$H$_4$), 6.61 (m, 1H, C$_5$H$_4$), 6.56 (m, 1H, 3-H in indenyl), 6.43 (m, 1H, 1-H in indenyl), 6.32 (m, 1H, C$_5$H$_4$), 5.40 (m, 1H, C$_5$H$_4$), 2.32 (s, 3H, 2-Me in indenyl), 0.94 (s, 3H, SiMeMe'), 0.65 (s, 3H, SiMeMe').

$^{13}$C{$^1$H} NMR (CD$_2$Cl$_2$): δ 142.5, 136.9, 135.7, 135.3, 128.7, 128.13, 128.10, 126.1, 126.0, 120.2, 119.7, 114.2, 110.3, 100.6, 18.4, −1.7, −2.9.

Complex 7-Hf

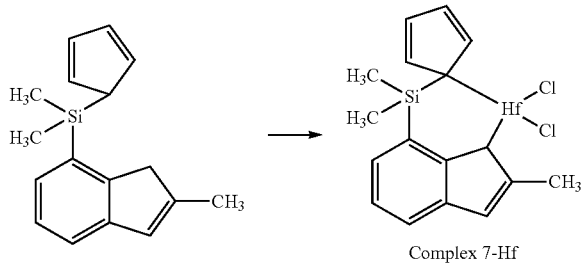

Complex 7-Hf

To a solution of 2.52 g (10.0 mmol) of ligand 7 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 4.64 g (10 mmol) of HfCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 30 ml of toluene. Crystals precipitated at −30° C. were collected, washed by 3×7 ml of cold toluene, 2×10 ml of hexanes, and dried in vacuum. Yield 2.15 g (43%).

Anal. calc. for C$_{17}$H$_{18}$Cl$_2$SiHf: C, 40.85; H, 3.63. Found: C, 41.09; H, 3.80.

$^1$H NMR (CD$_2$Cl$_2$): δ 7.55 (m, 1H, 7-H in indenyl), 7.26 (dd, J=7.3 Hz, J=6.4 Hz, 6-H in indenyl), 7.15 (dd, J=6.4 Hz, J=0.8 Hz, 5-H in indenyl), 6.77 (m, 1H, C$_5$H$_4$), 6.52 (m, 1H, C$_5$H$_4$), 6.37 (m, 1H, 3-H in indenyl), 6.31 (m, 1H, 1-H in indenyl), 6.23 (m, 1H, C$_5$H$_4$), 5.29 (m, 1H, C$_5$H$_4$), 2.39 (s, 3H, 2-Me in indenyl), 0.93 (s, 3H, SiMeMe'), 0.65 (s, 3H, SiMeMe').

$^{13}$C{$^1$H} NMR (CD$_2$Cl$_2$): δ 141.4, 136.2, 135.3, 128.7, 127.9, 126.4, 126.0, 123.9, 122.4, 119.2, 118.2, 113.3, 108.0, 98.4, 18.3, −1.7, −2.7.

Complex 8-Zr

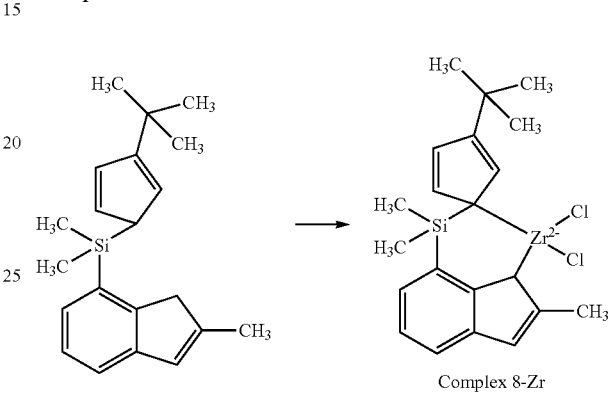

Complex 8-Zr

To a solution of 3.09 g (10.0 mmol) of ligand 8 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of ZrCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 30 ml of toluene. Crystals precipitated at −30° C. were collected, washed by 3×2 ml of cold toluene, 2×10 ml of hexanes, and dried in vacuum. Yield 1.69 g (36%) of a ca. 8 to 1 mixture of the isomeric complexes.

Anal. calc. for C$_{21}$H$_{26}$Cl$_2$SiZr: C, 53.82; H, 5.59. Found: C, 53.88; H, 5.74.

$^1$H NMR (C$_6$D$_6$): major isomer, δ 7.54 (d, J=8.3 Hz, 1H, 7-H in indenyl), 7.14 (m, 1H, 6-H in indenyl), 6.86 (d, J=6.6 Hz, 5-H in indenyl), 6.64 (m, 1H, C$_5$H$_4$), 6.21 (m, 1H, 3-H in indenyl), 6.13 (m, 1H, 1-H in indenyl), 5.99 (m, 1H, C$_5$H$_4$), 5.46 (m, 1H, C$_5$H$_4$), 2.21 (s, 3H, 2-Me in indenyl), 1.33 (s, 9H, $^t$Bu), 0.47 (s, 3H, SiMeMe'), 0.26 (s, 3H, SiMeMe').

Complex 9-Zr

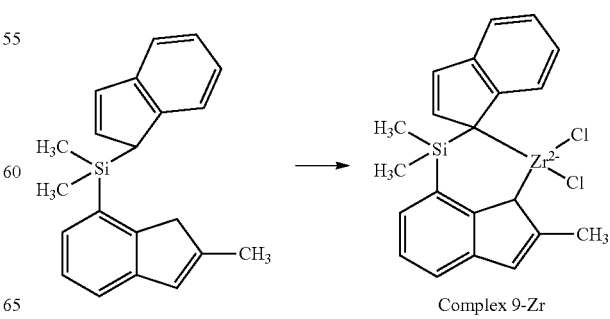

Complex 9-Zr

To a solution of 3.02 g (10.0 mmol) of ligand 9 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of ZrCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 20 ml of toluene. Crystals precipitated at −30° C. were collected, washed by 3×2 ml of cold toluene, 2×7 ml of hexanes, and dried in vacuum. Yield 2.04 g (44%) of a ca. 7 to 1 mixture of the isomeric complexes.

Anal. calc. for $C_{21}H_{20}Cl_2SiZr$: C, 54.52; H, 4.36. Found: C, 54.68; H, 4.15.

$^1$H NMR (CD$_2$Cl$_2$): major isomer, δ 7.57 (m, 1H), 7.50 (m, 1H), 7.29 (m, 3H), 7.11 (m, 1H), 6.99 (m, 3H), 6.87 (m, 1H), 6.61 (m, 1H), 6.34 (m, 1H), 2.28 (s, 3H, 2-Me in 2-methyl-indenyl), 1.04 (s, 3H, SiMeMe'), 0.92 (s, 3H, SiMeMe').

$^{13}$C{$^1$H} NMR (CD$_2$Cl$_2$): δ 141.4, 135.8, 133.5, 132.9, 129.4, 129.0, 128.6, 128.5, 127.9, 127.1, 126.9, 126.0, 123.8, 119.0, 118.3, 110.6, 101.2, 100.8, 18.4, −0.4, −2.6.

Complex 9-Hf

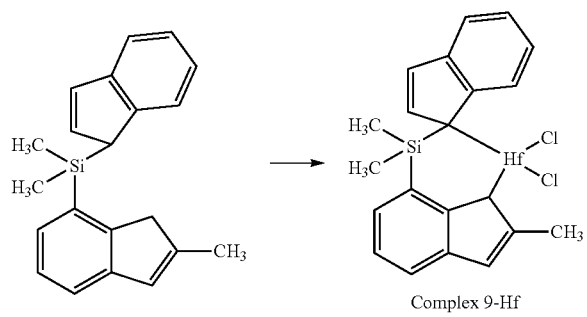

Complex 9-Hf

To a solution of 3.02 g (10.0 mmol) of ligand 9 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 4.64 g (10 mmol) of HfCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was washed by 3×4 ml of cold toluene, 2×10 ml of hexanes, and dried in vacuum. Yield 1.48 g (27%) of one pure isomer.

Anal. calc. for $C_{21}H_{20}Cl_2SiHf$: C, 45.87; H, 3.67. Found: C, 46.02; H, 3.77.

$^1$H NMR (CD$_2$Cl$_2$): δ 7.54 (m, 1H, 5-H in inden-4-yl), 7.45 (m, 1H, 7-H in inden-4-yl), 7.21-7.29 (m, 2H, 5,6-H in inden-1-yl), 7.07 (m, 1H, 6-H in inden-4-yl), 6.96 (m, 1H, 2-H in inden-1-yl), 6.93 (m, 1H, 4-H in inden-1-yl), 6.86 (m, 1H, 7-H in inden-1-yl), 6.85 (m, 1H, 3-H in inden-1-yl), 6.45 (m, 1H, 1-H in inden-4-yl), 6.21 (m, 1H, 3-H in inden-4-yl), 2.36 (s, 3H, 2-Me), 1.03 (s, 3H, SiMeMe'), 0.91 (s, 3H, SiMeMe').

Complex 10-Zr

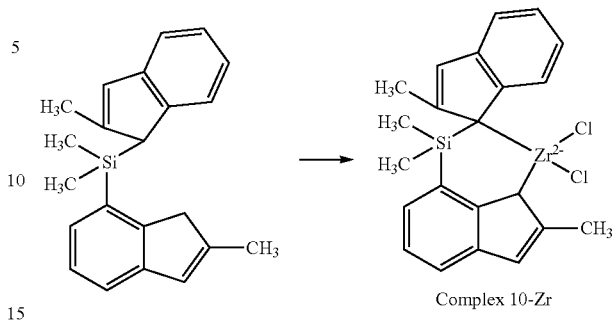

Complex 10-Zr

To a solution of 3.17 g (10.0 mmol) of ligand 1 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of ZrCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 30 ml of toluene. Crystals precipitated at −30° C. were collected, washed by 3×2 ml of cold toluene, 2×7 ml of hexanes, and dried in vacuum. Yield 2.72 g (57%) of one pure isomer.

Anal. calc. for $C_{22}H_{22}Cl_2SiZr$: C, 55.44; H, 4.65. Found: C, 55.67; H, 4.77.

$^1$H NMR (CD$_2$Cl$_2$): δ 7.38-7.47 (m, 3H), 7.26 (m, 1H), 7.08 (m, 1H), 6.86 (s, 1H), 6.79 (m, 1H), 6.74 (m, 1H), 6.32 (m, 2H), 2.61 (s, 3H), 2.30 (s, 3H), 1.13 (s, 3H), 0.89 (s, 3H).

$^{13}$C{$^1$H} NMR (CD$_2$Cl$_2$): δ 143.7, 135.1, 134.2, 133.4, 130.6, 130.2, 129.4, 127.7, 126.6, 126.3, 127.5, 126.7, 126.5, 125.9, 122.9, 111.1, 102.3, 101.9, 19.1, 18.5, 2.0, −1.6.

Complex 10-Hf

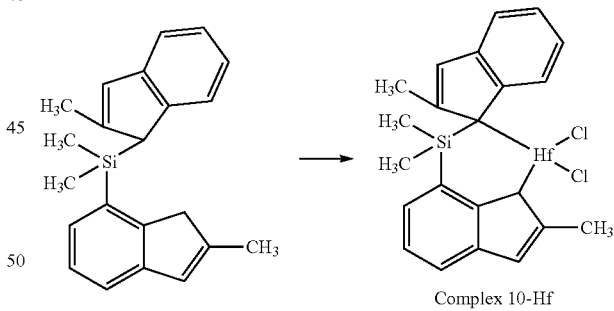

Complex 10-Hf

To a solution of 3.17 g (10.0 mmol) of ligand 10 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 4.64 g (10 mmol) of HfCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 40 ml of toluene. Crystals precipitated at −30° C. were collected, washed by 3×2 ml of cold toluene, 2×7 ml of hexanes, and dried in vacuum. Yield 2.09 g (37%) of a ca. 10 to 1 mixture of the isomeric complexes.

Anal. calc. for C$_{22}$H$_{22}$Cl$_2$SiHf: C, 46.86; H, 3.93. Found: C, 56.81; H, 4.15.

$^1$H NMR (C$_6$D$_6$): major isomer, δ 7.32 (m, 2H, 4,7-H in inden-1-yl), 7.06 (m, 1H, 5-H in inden-4-yl), 7.01 (m, 1H, 6-H in inden-4-yl), 6.92 (m, 1H, 7-H in inden-4-yl), 6.64 (m, 2H, 5,6-H in inden-1-yl), 6.59 (s, 1H, 3-H in inden-1-yl), 6.09 (m, 1H, 3-H in inden-4-yl), 5.85 (m, 1H, 1-H in inden-1-yl), 2.27 (s, 3H, 2-Me in inden-1/4-yl), 2.25 (s, 3H, 2-Me in inden-4/1-yl), 0.69 (s, 3H, SiMeMe'), 0.54 (s, 3H, SiMeMe').
Complex 11-Zr

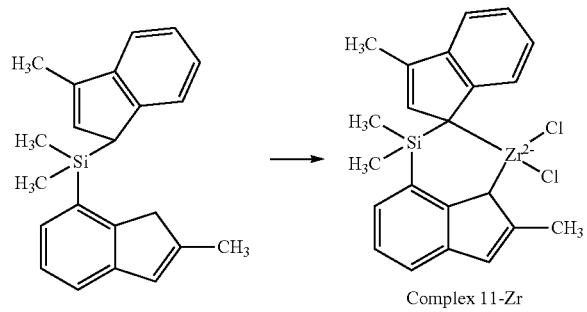

Complex 11-Zr

To a solution of 3.17 g (10.0 mmol) of ligand 11 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of ZrCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 40 ml of toluene. Crystals precipitated at −30° C. were collected, washed by 3×2 ml of cold toluene, 2×7 ml of hexanes, and dried in vacuum. Yield 2.62 g (55%) of one pure isomer.

Anal. calc. for C$_{22}$H$_{22}$Cl$_2$SiZr: C, 55.44; H, 4.65. Found: C, 55.61; H, 4.45.

$^1$H NMR (CD$_2$Cl$_2$): δ 7.47 (m, 2H), 7.38 (m, 1H), 7.22-7.31 (m, 2H), 7.10 (m, 1H), 6.93 (m, 1H), 6.80 (m, 1H), 6.53-6.56 (m, 2H), 6.32 (m, 1H), 2.51 (s, 3H), 2.25 (s, 3H), 1.03 (s, 3H), 0.88 (s, 3H).
Complex 11-Hf

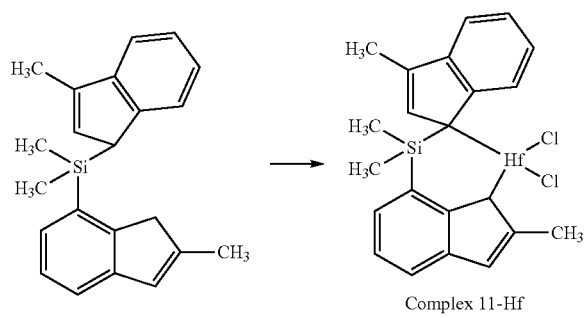

Complex 11-Hf

To a solution of 3.17 g (10.0 mmol) of ligand 11 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 4.64 g (10 mmol) of HfCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 40 ml of toluene. Crystals precipitated at −30° C. were collected, washed by 3×2 ml of cold toluene, 2×7 ml of hexanes, and dried in vacuum. Yield 2.65 g (47%) of one pure isomer.

Anal. calc. for C$_{22}$H$_{22}$Cl$_2$SiHf: C, 46.86; H, 3.93. Found: C, 46.08; H, 3.10.

$^1$H NMR (CD$_2$Cl$_2$): δ 7.43 (m, 1H, 7-H in inden-4-yl), 7.36 (m, 1H, 4/7-H in inden-1-yl), 7.21-7.33 (m, 2H, 5,6-H in inden-4-yl), 7.07 (m, 1H, 5/6-H in inden-1-yl), 6.88 (m, 1H, 6/5-H in inden-1-yl), 6.79 (m, 1H, 7/4-H in inden-1-yl), 6.52 (s, 1H, 2-H in inden-1-yl), 6.40 (m, 1H, 3-H in inden-4-yl), 6.21 (m, 1H, 1-H in inden-1-yl), 2.58 (s, 3H, 2-Me in inden-1/4-yl), 2.33 (s, 3H, 2-Me in inden-4/1-yl), 1.01 (s, 3H, SiMeMe'), 0.87 (s, 3H, SiMeMe').
Complex 12-Zr

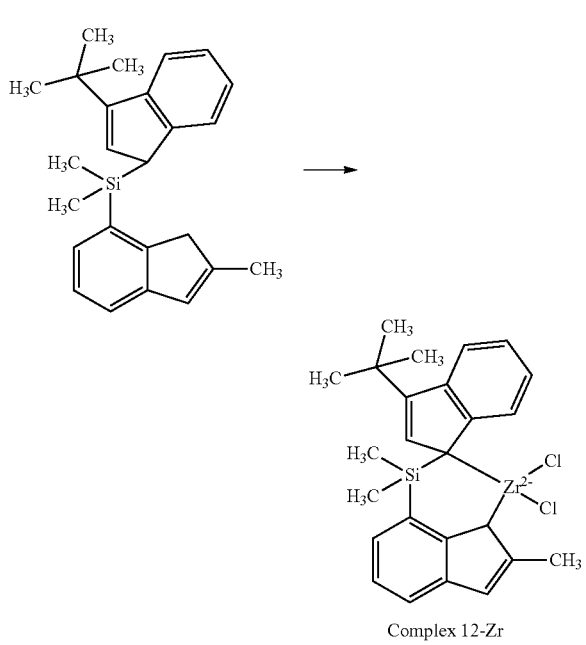

Complex 12-Zr

To a solution of 3.59 g (10.0 mmol) of ligand 12 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of ZrCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 40 ml of toluene. Crystals precipitated at −30° C. were collected, washed by 3×2 ml of cold toluene, 2×7 ml of hexanes, and dried in vacuum. Yield 1.38 g (29%) of a ca. 3.7 to 1 mixture of the isomeric complexes.

Anal. calc. for C$_{25}$H$_{28}$Cl$_2$SiZr: C, 57.89; H, 5.44. Found: C, 58.11; H, 5.60.

$^1$H NMR (CD$_2$Cl$_2$): major isomer, δ 7.90 (m, 2H), 7.55 (m, 1H), 7.27-7.34 (m, 3H), 7.19 (m, 1H), 6.61 (m, 1H), 6.18 (m, 1H), 5.56 (m, 1H), 1.82 (s, 3H), 1.37 (s, 9H), 1.18 (s, 3H), 0.68 (s, 3H).

Complex 12-Hf

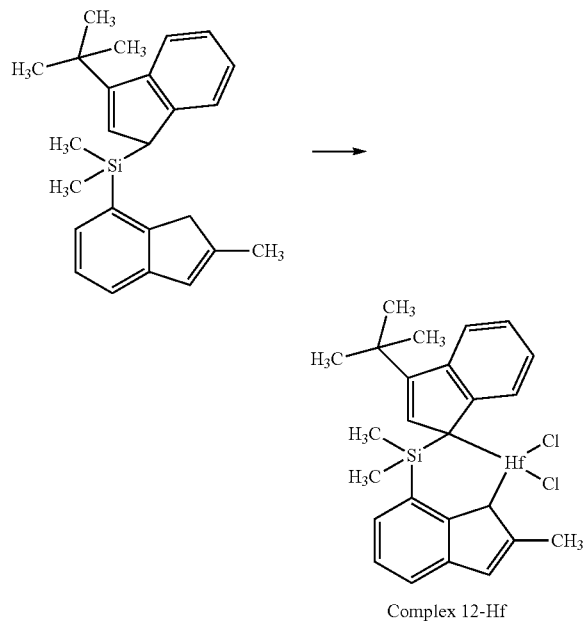

Complex 12-Hf

To a solution of 3.59 g (10.0 mmol) of ligand 12 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 4.64 g (10 mmol) of HfCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 40 ml of toluene. Crystals precipitated at −30° C. were collected, washed by 3×2 ml of cold toluene, 2×7 ml of hexanes, and dried in vacuum. Yield 1.58 g (26%) of a ca. 14 to 3 mixture of the isomeric complexes.

Anal. calc. for C$_{25}$H$_{28}$Cl$_2$SiHf: C, 49.55; H, 4.66. Found: C, 49.71; H, 4.79.

$^1$H NMR (CD$_2$Cl$_2$): major isomer, δ 7.81-7.95 (m, 2H, 4,7-H in inden-1-yl), 7.52 (m, 1H, 7-H in inden-4-yl), 7.17-7.30 (m, 4H, 5,6-H in inden-1-yl and 5,6-H in inden-4-yl), 6.43 (m, 1H, 3-H in inden-4-yl), 6.09 (m, 1H, 1-H in inden-4-yl), 5.50 (s, 1H, 2-H in inden-1-yl), 1.89 (s, 3H, 2-Me), 1.36 (s, 9H, $^t$Bu), 1.17 (s, 3H, SiMeMe'), 0.68 (s, 3H, SiMeMe').

Complex 13-Zr

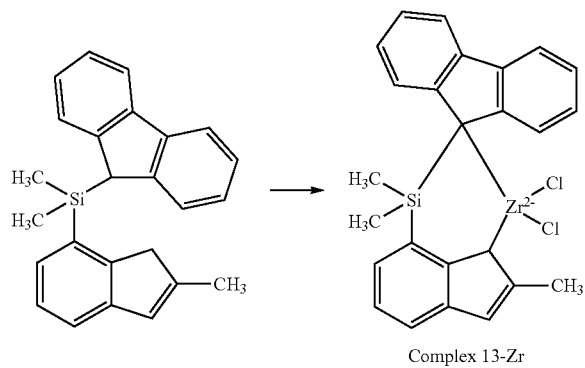

Complex 13-Zr

To a solution of 3.53 g (10.0 mmol) of ligand 13 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of ZrCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 80 ml of toluene. Crystals precipitated at −30° C. were collected, washed by 3×2 ml of cold toluene, 2×7 ml of hexanes, and dried in vacuum. Yield 3.08 g (60%).

Anal. calc. for C$_{25}$H$_{22}$Cl$_2$SiZr: C, 58.57; H, 4.33. Found: C, 58.79; H, 4.41.

$^1$H NMR (C$_6$D$_6$): δ 7.85 (m, 1H), 7.70 (m, 1H), 7.59 (m, 1H), 7.32-7.37 (m, 3H), 7.18 (dd, J=6.5 Hz, J=1.0 Hz, 1H, 5-H in indenyl), 7.13 (m, 1H), 6.99 (dd, J=8.5 Hz, J=6.5 Hz, 1H, 6-H in indenyl), 6.90 (ddd, J=8.7 Hz, J=6.7 Hz, J=1.0 Hz, 1H), 6.83 (m, 1H, 7-H in indenyl), 6.32 (m, 1H, 1-H in indenyl), 5.98 (m, 1H, 3-H in indenyl), 1.83 (s, 3H, 2-Me in indenyl), 0.90 (s, 3H, SiMeMe'), 0.57 (s, 3H, SiMeMe').

Complex 14-Zr

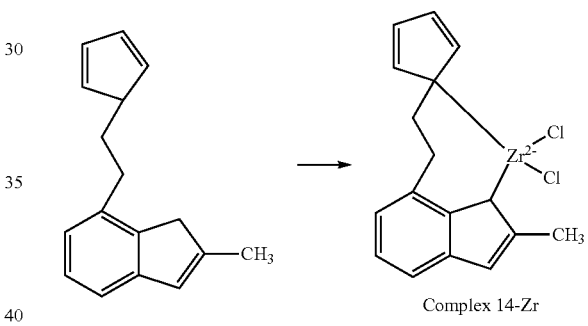

Complex 14-Zr

To a solution of 2.22 g (10.0 mmol) of ligand 14 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of ZrCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 20 ml of toluene. Crystals precipitated at −30° C. were collected, washed by 2×2 ml of cold toluene, 3×10 ml of hexanes, and dried in vacuum. Yield 1.22 g (32%).

Anal. calc. for C$_{17}$H$_{16}$Cl$_2$Zr: C, 53.39; H, 4.22. Found: C, 53.52; H, 4.06.

$^1$H NMR (CD$_2$Cl$_2$): δ 7.54 (m, 1H, 7-H in indenyl), 7.16 (dd, J=8.3 Hz, J=7.1 Hz, 6-H in indenyl), 7.05 (m, 1H, 5-H in indenyl), 6.54 (m, 1H, CH in Cp), 6.39 (m, 1H, 1/3-H in indenyl), 6.23 (m, 1H, CH in Cp), 6.17 (m, 1H, 3/1-H in indenyl), 6.12 (m, 1H, CH in Cp), 4.62 (m, 1H, CH in Cp), 3.63 (m, 1H, CHH'), 3.45 (m, 1H, CHH'), 3.21 (m, 1H, CHH'), 3.06 (m, 1H, CHH'), 2.31 (s, 3H, 2-Me in indenyl).

Complex 14-Hf

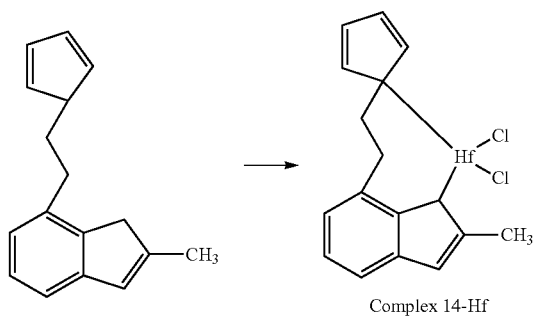

Complex 14-Hf

To a solution of 2.22 g (10.0 mmol) of ligand 14 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 4.64 g (10 mmol) of $HfCl_4(THF)_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness. The residue was washed by 50 ml of hexanes, and then the product was extracted by 3×5 ml of ether. Crystals precipitated at −30° C. were collected and dried in vacuum. Yield 1.60 g (34%).

Anal. calc. for $C_{17}H_{16}Cl_2Hf$: C, 43.47; H, 3.43. Found: C, 43.22; H, 3.49.

$^1$H NMR ($CD_2Cl_2$): δ 7.52 (m, 1H, 7-H in indenyl), 7.13 (dd, J=8.3 Hz, J=6.8 Hz, 6-H in indenyl), 7.03 (m, 1H, 5-H in indenyl), 6.42 (m, 1H, CH in Cp), 6.26 (m, 1H, 1/3-H in indenyl), 6.14 (m, 1H, CH in Cp), 6.00 (m, 1H, 3/1-H in indenyl), 5.95 (m, 1H, CH in Cp), 4.47 (m, 1H, CH in Cp), 3.68 (m, 1H, CHH'), 3.52 (m, 1H, CHH'), 3.24 (m, 2H, CHH'CHH'), 2.39 (s, 3H, 2-Me in indenyl).

Complex 15-Zr

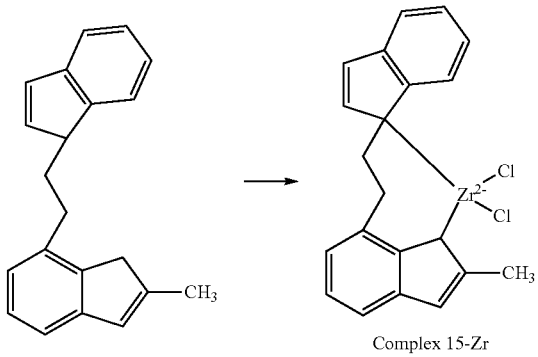

Complex 15-Zr

To a solution of 2.72 g (10.0 mmol) of ligand 15 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of $ZrCl_4(THF)_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 30 ml of toluene. Crystals precipitated at −30° C. were collected, washed by 2×3 ml of cold toluene, 3×10 ml of hexanes, and dried in vacuum. Yield 1.77 g (41%) of one pure isomer.

Anal. calc. for $C_{21}H_{18}Cl_2Zr$: C, 58.32; H, 4.19. Found: C, 58.47; H, 4.34.

$^1$H NMR ($CD_2Cl_2$): δ 7.71 (m, 1H), 7.09-7.44 (m, 5H), 6.87 (m, 1H), 6.54 (m, 1H), 6.22 (m, 1H), 5.70 (m, 1H), 4.49 (m, 1H), 3.46 (m, 1H, CHH'), 3.28 (m, 1H, CHH'), 2.82 (m, 1H, CHH'), 2.66 (m, 1H, CHH'), 2.04 (s, 3H, 2-Me in indenyl).

Complex 16-Zr

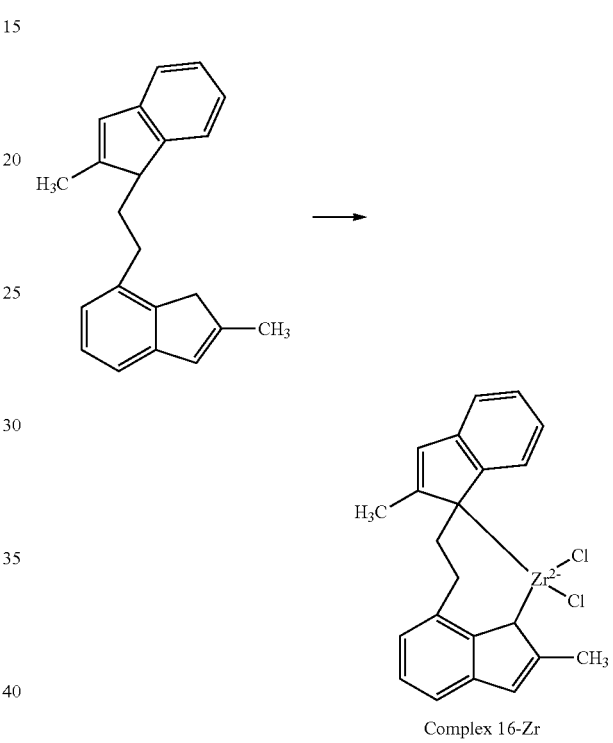

Complex 16-Zr

To a solution of 2.86 g (10.0 mmol) of ligand 16 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of $ZrCl_4(THF)_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 15 ml of toluene. Crystals precipitated at −30° C. were collected, washed by 2×5 ml of cold toluene, 2×20 ml of hexanes, and dried in vacuum. Yield 804 mg (18%) of a ca. 2 to 1 mixture of the isomeric complexes.

Anal. calc. for $C_{22}H_{20}Cl_2Zr$: C, 59.18; H, 4.51. Found: C, 59.40; H, 4.65.

$^1$H NMR ($C_6D_6$): major isomer, δ 7.62 (m, 1H), 7.49 (m, 1H), 7.33 (m, 1H), 7.01 (m, 1H), 6.95 (m, 1H), 6.90 (m, 1H), 6.66 (m, 1H), 6.02 (m, 1H), 5.98 (m, 1H), 5.72 (m, 1H), 3.21 (m, 1H, CHH'), 2.74 (m, 1H, CHH'), 2.68 (m, 1H, CHH'), 2.35 (m, 1H, CHH'), 1.74 (s, 3H, Me), 1.54 (s, 3H, Me).

Complex 17-Zr

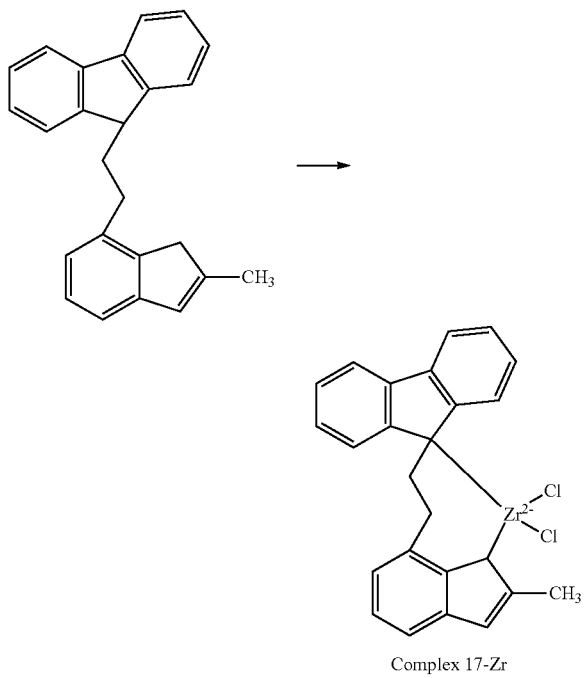

Complex 17-Zr

To a solution of 3.22 g (10.0 mmol) of ligand 17 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of ZrCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 20 ml of toluene. Crystals precipitated at −30° C. were collected, washed by 2×3 ml of cold toluene, 2×10 ml of hexanes, and dried in vacuum. Yield 3.33 g (69%).

Anal. calc. for C$_{25}$H$_{20}$Cl$_2$Zr: C, 62.22; H, 4.18. Found: C, 62.37; H, 4.07.

$^1$H NMR (CD$_2$Cl$_2$): δ 8.26 (m, 1H), 8.09 (m, 1H), 8.00 (m, 1H), 7.61 (m, 2H), 7.53 (m, 1H), 7.40 (m, 1H), 7.28 (m, 3H), 7.13 (m, 1H), 6.42 (m, 1H, 3-H in indenyl), 6.24 (m, 1H, 1-H in indenyl), 4.04 (m, 2H, CHH'CHH'), 3.57 (m, 2H, CHH'CHH'), 1.98 (s, 3H, 2-Me in indenyl).

Complex 18-Zr

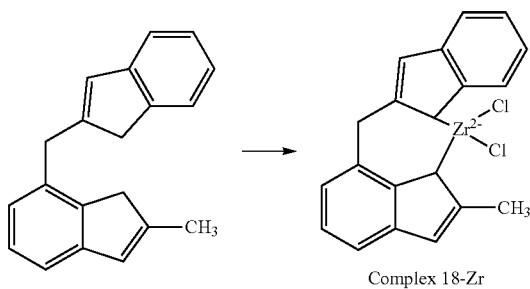

Complex 18-Zr

To a solution of 2.58 g (10.0 mmol) of ligand 18 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of ZrCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was washed by 3×5 ml of toluene, 3×2 ml of dichloromethane, 2×10 ml of hexanes, and dried in vacuum. Yield 1.05 g (25%).

Anal. calc. for C$_{20}$H$_{16}$Cl$_2$Zr: C, 57.40; H, 3.85. Found: C, 57.46; H, 4.04.

$^1$H NMR (CD$_2$Cl$_2$): δ 7.36-7.45 (m, 3H), 7.25 (m, 2H), 7.10 (m, 1H), 6.90 (m, 1H), 6.60 (m, 1H), 6.39 (m, 1H), 6.28 (m, 1H), 4.67 (m, 1H), 4.27 (d, J=13.4 Hz, 1H, CHH'), 3.94 (d, J=13.4 Hz, 1H, CHH'), 2.34 (s, 3H, Me).

$^{13}$C{$^1$H} NMR (CD$_2$Cl$_2$): δ 139.6, 135.0, 134.8, 129.4, 127.8, 126.6, 126.3, 125.9, 123.1, 122.0, 119.7, 110.5, 108.5, 102.5, 101.5, 35.1, 18.3.

Complex 18-Hf

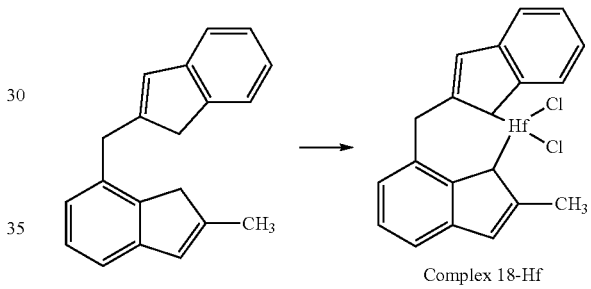

Complex 18-Hf

To a solution of 2.58 g (10.0 mmol) of ligand 18 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 4.64 g (10 mmol) of HfCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 40 ml of toluene. Crystals precipitated at −30° C. were collected, washed by 3×5 ml of cold toluene, 2×10 ml of hexanes, and dried in vacuum. Yield 1.57 g (31%).

Anal. calc. for C$_{20}$H$_{16}$Cl$_2$Hf: C, 47.50; H, 3.19. Found: C, 47.69; H, 3.30.

$^1$H NMR (CD$_2$Cl$_2$): δ 7.41 (m, 1H), 7.37 (m, 1H), 7.34 (m, 1H), 7.21 (m, 2H), 7.06 (m, 1H), 6.91 (m, 1H), 6.37 (m, 1H), 6.28 (m, 1H), 6.16 (m, 1H), 4.53 (m, 1H), 4.29 (d, J=13.5 Hz, 1H, CHH'), 4.07 (d, J=13.5 Hz, 1H, CHH'), 2.41 (s, 3H, 2-Me in indenyl).

Example 5

2-[2-(1-Methoxy-2-methyl-2,3-dihydro-1H-inden-4-yl)ethyl]indan-2-ol

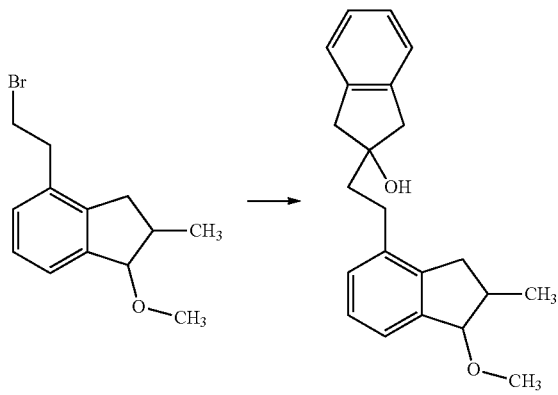 [SMILES: COC1c2cccc(CCBr)c2CC1C ; COC1c2cccc(CCC3(O)Cc4ccccc4C3)c2CC1C]

To 2.26 g (93.0 mmol) of magnesium turnings in 20 ml of THF a solution of 16.7 g (62.0 mmol) of 4-(2-bromoethyl)-1-methoxy-2-methylindane in 80 ml of THF was added dropwise at reflux. The resulting mixture was additionally refluxed for 1 h, and then this Grignard reagent was titrated. To a suspension of 10.9 g (44.1 mmol) of anhydrous $CeCl_3$ in 160 ml of THF 100 ml (44.1 mmol) of 0.441 M solution of the Grignard reagent was added at vigorous stirring for 15 min at 0° C., and then the reaction mixture was stirred at this temperature for 1.5 h. Further on, 5.83 g (44.1 mmol) of indanone-2 was added at 0° C. This mixture was stirred overnight at room temperature, and then 300 ml of 10% acetic acid was added. The product was extracted by 3×100 ml of ether. The combined extract was washed by brain and aqueous $Na_2CO_3$. The organic layer was separated, dried over $Na_2SO_4$, and evaporated to dryness. The title product was isolated by flash chromatography on Silica Gel 60 (40-63 um, d 50 mm, l 300 mm, eluent: hexanes/ether=3/1). Yield 10.7 g (75%) of a one diastereomer (as the starting material was one pure diastereomer).

Anal. calc. for $C_{22}H_{26}O_2$: C, 81.95; H, 8.13. Found: C, 82.29; H, 8.32.

$^1$H NMR ($CDCl_3$): δ 7.12-7.26 (m, 7H, 4,5,6,7-H in indan-2-ol and 5,6,7-H in methoxyindane), 4.42 (d, J=4.1 Hz, 1H, CHOMe), 3.46 (s, 3H, OMe), 3.23 (dd, J=15.7 Hz, J=7.6 Hz, 1H, CHH'CHMe), 3.12 (d, J=16.2 Hz, 2H, CHH' in indan-2-ol), 3.00 (d, J=16.2 Hz, 2H, CHH' in indan-2-ol), 2.80 (m, 2H, HOCCH$_2$CH$_2$), 2.52 (m, 1H, CHMe), 2.43 (dd, J=15.7 Hz, J=5.1 Hz, 1H, CHH'CHMe), 2.03 (m, 2H, HOCCH$_2$), 1.83 (br.s, 1H, OH), 1.18 (d, J=7.0 Hz, 3H, CHMe).

Ligand 19

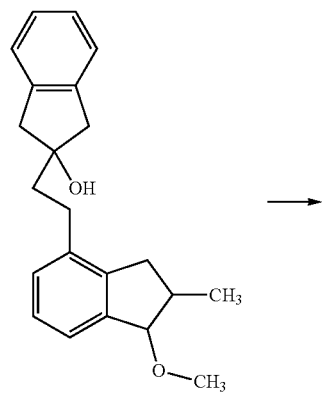

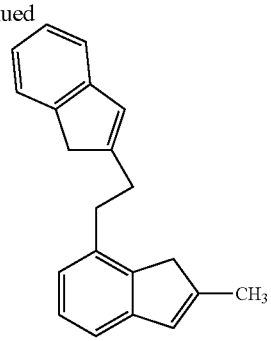

To a hot (110° C.) solution of 4.00 g (12.4 mmol) of 2-[2-(1-methoxy-2-methyl-2,3-dihydro-1H-inden-4-yl)ethyl]indan-2-ol in 730 ml of toluene 0.37 g of TsOH was added. This mixture was refluxed with Dean-Stark trap for 35 min, and then 0.75 g of TsOH was added. The resulting mixture was refluxed for 35 min and then passed through the layer of Silica Gel 60 (40-63 um, d 80 mm, l 50 mm). The Silica Gel layer was additionally washed by 500 ml of toluene. The combined organic extract was evaporated to dryness. The product was isolated by flash chromatography using a short column with Silica Gel 60 (40-63 um, d 80 mm, 150 mm; eluent: hexanes). Yield 2.87 g (85%) of 7-[2-(1H-inden-2-yl)ethyl]-2-methyl-1H-indene.

Anal. calc. for $C_{24}H_{20}$: C, 92.60; H, 7.40. Found: C, 92.89; H, 7.64.

$^1$H NMR ($CDCl_3$): δ 7.39 (m, 1H, 4-H in inden-7-yl), 7.28 (m, 2H, 5,6-H in inden-2-yl), 7.25 (m, 1H, 5-H in inden-7-yl), 7.13 (m, 2H, 4,7-H in inden-2-yl), 6.99 (m, 1H, 6-H in inden-7-yl), 6.51 (m, 1H, 3-H in inden-7-yl), 3.36 (m, 2H, 1,1'-H in inden-2-yl), 3.27 (m, 2H, 1,1'-H in inden-7-yl), 2.99 (m, 2H, inden-2-yl-CH$_2$CH$_2$-inden-7-yl), 2.85 (m, 2H, inden-2-yl-CH$_2$CH$_2$-inden-7-yl), 2.17 (m, 3H, Me).

Complex 19-Zr

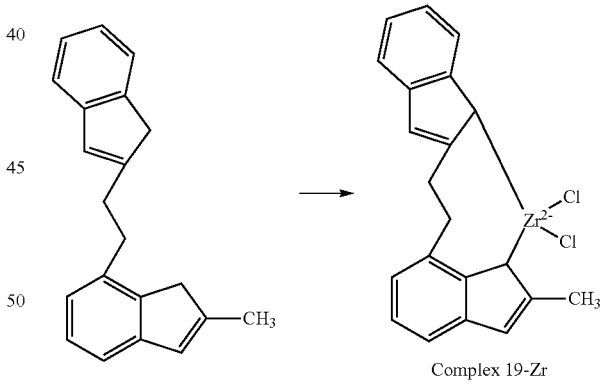

Complex 19-Zr

To a solution of 2.72 g (10.0 mmol) of ligand 19 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10.0 mmol) of $ZrCl_4(THF)_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 30 ml of toluene. Crystals precipitated at −30° C. were collected, washed by 3×3 ml of cold toluene, 2×10 ml of hexanes, and dried in vacuum. Yield 2.25 g (52%).

Anal. calc. for C₁₆H₁₄Cl₂Zr: C, 58.32; H, 4.19. Found: C, 58.30; H, 4.32.

¹H NMR (CD₂Cl₂): δ 7.61 (m, 1H), 7.47 (m, 1H), 7.22 (m, 1H), 7.12-7.17 (m, 4H), 6.33 (m, 1H), 6.18 (m, 1H), 6.14 (m, 1H), 4.46 (m, 1H), 3.76 (m, 1H), 3.60 (m, 1H), 3.36 (m, 1H), 3.26 (m, 1H), 2.30 (m, 3H).

¹³C{¹H} NMR (CD₂Cl₂): δ 143.3, 137.7, 136.9, 131.3, 131.0, 130.5, 129.7, 128.0, 126.91, 126.87, 126.63, 126.58, 126.2, 124.1, 111.6, 107.3, 103.3, 101.2, 30.6, 28.5, 18.7.

Complex 19-Hf

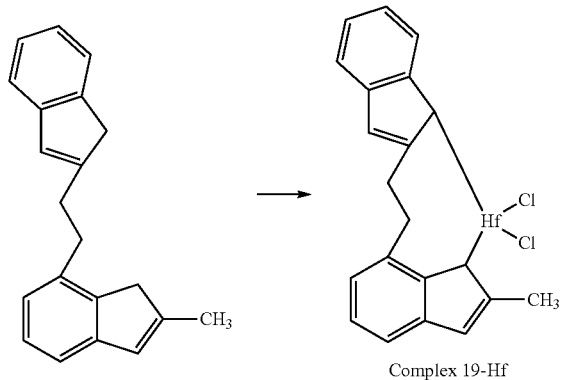

Complex 19-Hf

To a solution of 2.72 g (10.0 mmol) of ligand 19 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 4.64 g (10.0 mmol) of HfCl₄(THF)₂. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 30 ml of toluene. Crystals precipitated at −30° C. were collected, washed by 3×3 ml of cold toluene, 2×10 ml of hexanes, and dried in vacuum. Yield 4.05 g (78%).

Anal. calc. for C₁₆H₁₄Cl₂Hf: C, 48.53; H, 3.49. Found: C, 48.77; H, 3.60.

¹H NMR (CD₂Cl₂): δ 7.58 (m, 1H), 7.46 (m, 1H), 7.19 (m, 1H), 7.08-7.15 (m, 4H), 6.21 (m, 1H), 6.05 (m, 1H), 5.98 (m, 1H), 4.34 (m, 1H), 3.81 (m, 1H), 3.67 (m, 1H), 3.50 (m, 1H), 3.35 (m, 1H), 2.40 (m, 3H).

¹³C{¹H} NMR (CD₂Cl₂): δ 142.3, 137.8, 136.8, 131.1, 130.5, 129.7, 129.4, 127.8, 127.0, 126.7, 126.5, 126.3, 125.7, 124.0, 109.2, 103.6, 100.9, 98.4, 30.6, 28.2, 18.6.

Example 6

2-[(1-Methoxy-2-methyl-2,3-dihydro-1H-inden-4-yl)methylene]-5-methylindan-1-one

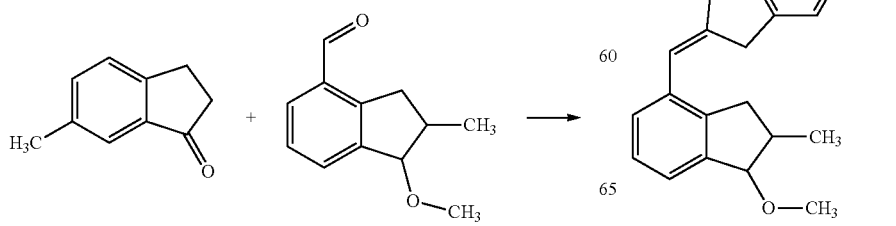

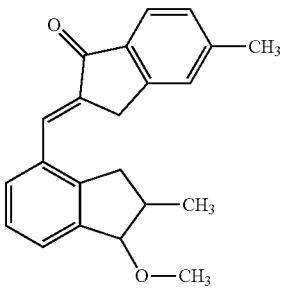

To sodium methylate obtained from 157 mg (6.83 mmol) of sodium and 60 ml of methanol 4.70 g (24.7 mmol) of 1-methoxy-2-methylindane-4-carbaldehyde was added at 0° C. The resulting mixture was stirred for 5 min at this temperature, and 3.32 g (22.7 mmol) of 6-methylindan-1-one was added. This mixture was stirred overnight at room temperature, and 5% HCl was added to pH 5. The precipitate formed was filtered off and washed by 3×10 ml of cold methanol. Yield 6.87 g (95%) of a ca. 1 to 1 mixture of two diastereomers.

Anal. calc. for C₂₂H₂₂O₂: C, 82.99; H, 6.96. Found: C, 83.31; H, 7.23.

¹H NMR (CDCl₃): δ 7.79 (d, J=7.8 Hz, 2H, 7-H in indan-2-diyl of both isomers), 7.73 (m, 1H, CH= of the isomer A), 7.71 (m, 1H, CH= of the isomer B), 7.63 (m, 2H, 7-H in indan-4-yl of both isomers), 7.40 (m, 2H, 6-H in indan-4-yl of both isomers), 7.32 (m, 2H, 5-H in indan-4-yl of both isomers), 7.31 (s, 2H, 4-H in indan-2-diyl of both isomers), 7.22 (d, J=7.8 Hz, 2H, 7-H in indan-2-diyl of both isomers), 4.57 (d, J=5.8 Hz, 1H, CHOMe of the isomer A), 4.42 (d, J=4.1 Hz, 1H, CHOMe of the isomer B), 3.96 (m, 4H, CH₂ in indan-2-diyl of both isomers), 3.47 (s, 3H, OMe of the isomer B), 3.43 (s, 3H, OMe of the isomer A), 3.41 (dd, J=16.2 Hz, J=7.6 Hz, 1H, CHH' in indan-4-yl of the isomer B), 3.12 (dd, J=16.0 Hz, J=7.3 Hz, 1H, CHH' in indan-4-yl of the isomer A), 2.86 (dd, J=16.0 Hz, J=6.3 Hz, 1H, CHH' in indan-4-yl of the isomer A), 2.67 (m, 1H, CHMe in indan-4-yl of the isomer A), 2.63 (dd, J=16.2 Hz, J=5.1 Hz, 1H, CHH' in indan-4-yl of the isomer B), 2.65 (m, 1H, CHMe in indan-4-yl of the isomer B), 2.46 (s, 6H, 6-Me in indan-2-diyl of both isomers), 1.18 (d, J=7.1 Hz, 3H, 2-Me in indan-4-yl of the isomer B), 1.10 (d, J=6.8 Hz, 3H, 2-Me in indan-4-yl of the isomer A).

2-[(1-Methoxy-2-methyl-2,3-dihydro-1H-inden-4-yl)methyl]-5-methylindan-1-ol

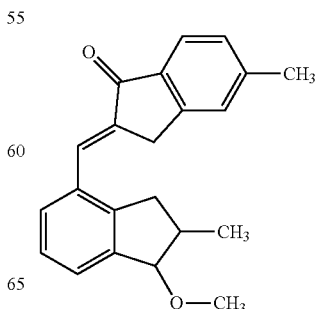

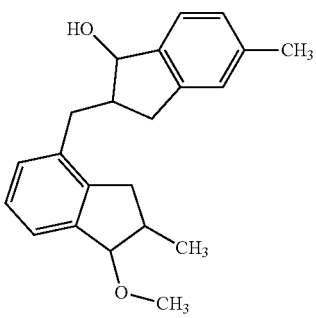

To a solution of 28.1 g (88.3 mmol) of 2-[(1-methoxy-2-methyl-2,3-dihydro-1H-inden-4-yl)methylene]-5-methylindan-1-one in 1800 ml of a mixture of THF and methanol (1 to 8, vol.) 4.50 g (119 mmol) of NaBH$_4$ was added by small portions at vigorous stirring at 0° C. This mixture was stirred for 1 h at room temperature, 65.6 g (0.276 mol) of CoCl$_2$ (H$_2$O) was added. The resulting mixture was stirred for 15 min at room temperature, and then 12.6 g (333 mmol) of NaBH$_4$ was added by small portions for ca. 15 min. This mixture was stirred for 2 h at room temperature and then evaporated to dryness. To the residue 1000 ml of warm water and 300 ml of dichloromethane were added. The organic layer was separated, the aqueous layer was extracted with 3×300 ml of dihloromethane. The combined extract was dried over Na$_2$SO$_4$ and evaporated to dryness. The product was isolated by flash chromatography on Silica Gel 60 (40-63 um, d 50 mm, 1300 mm, eluent: hexanes/ethyl acetate=3/1). Yield 22.8 g (80%).

Anal. calc. for C$_{22}$H$_{26}$O$_2$: C, 81.95; H, 8.13. Found: C, 82.29; H, 8.30.

$^1$H NMR (CDCl$_3$): δ 7.26 (m, 1H, 7-H in inden-4-yl), 7.24 (m, 1H, 6-H in inden-2-yl), 7.19 (m, 6-H in inden-4-yl), 7.15 (m, 1H, 5-H in inden-4-yl), 7.04 (m, 1H, 7-H in inden-2-yl), 6.98 (m, 1H, 4-H in inden-2-yl), 4.89 (m, 1H, CHOH), 4.39 (d, J=4.1 Hz, 1H, CHOMe), 3.46 (s, 3H, OMe), 3.20 (dd, J=15.6 Hz, J=7.4 Hz, 1H, CHH'CHMe in inden-4-yl), 2.93-3.02 (m, 2H, CHH'CHCH$_2$ in inden-2-yl and CHMe in inden-4-yl), 2.72 (dd, J=13.7 Hz, J=8.4 Hz, 1H, CHH'CHCH$_2$ in inden-2-yl), 2.46-2.56 (m, 3H, CH$_2$CH(CHOH)CH$_2$), 2.42 (dd, J=15.6 Hz, J=5.1 Hz, 1H, CHH'CHMe in inden-4-yl), 2.32 (m, 3H, 5-Me in inden-2-yl), 1.61 (br.d, J=5.4 Hz, 1H, OH), 1.15 (d, J=6.9 Hz, 3H, CHMe).

Ligand 20

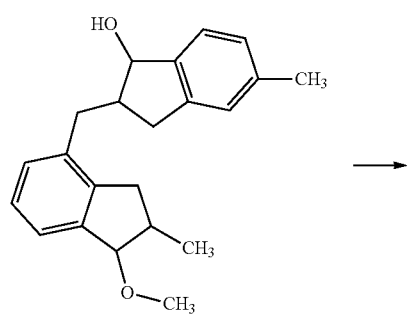

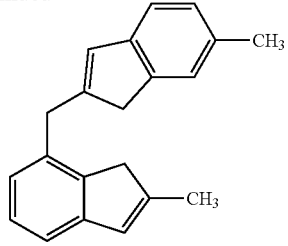

To a hot (110° C.) solution of 7.20 g (22.3 mmol) of 2-[(1-methoxy-2-methyl-2,3-dihydro-1H-inden-4-yl)methyl]-5-methylindan-1-ol in 1300 ml of toluene 0.67 g of TsOH was added. This mixture was refluxed with Dean-Stark trap for 10 min and then passed through the layer of Silica Gel 60 (40-63 um, d 80 mm, l 50 mm). The Silica Gel layer was additionally washed by 500 ml of toluene. The combined organic extract was evaporated to dryness. The product was isolated by flash chromatography using a short column with Silica Gel 60 (40-63 um, d 80 mm, 150 mm; eluent: hexanes). Yield 5.47 g (90%).

Anal. calc. for C$_{21}$H$_{20}$: C, 92.60; H, 7.40. Found: C, 92.49; H, 7.57.

$^1$H NMR (CDCl$_3$): δ 7.25 (m, 1H), 7.20-7.23 (m, 3H), 7.19 (s, 1H), 7.09 (m, 1H), 7.03 (m, 1H), 6.55 (m, 1H), 6.51 (m, 1H), 3.98 (s, 2H), 3.30 (m, 2H), 3.28 (m, 2H), 2.41 (s, 3H), 2.20 (m, 3H).

Complex 20-Zr

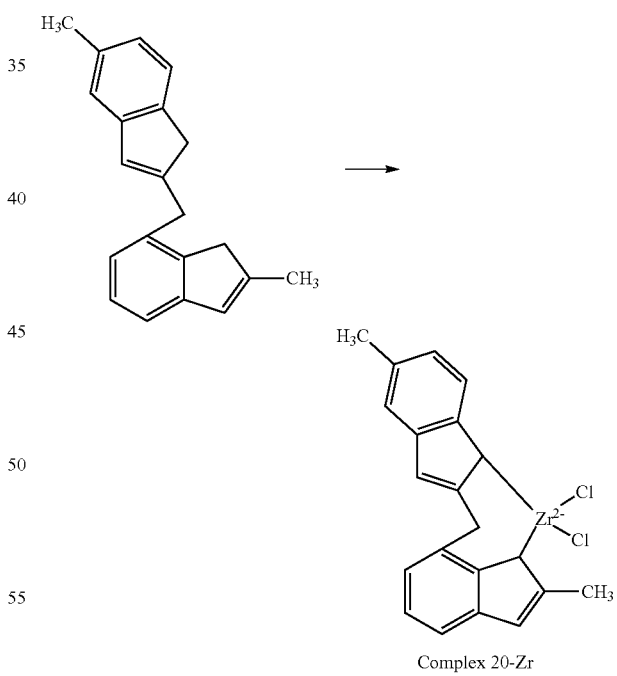

Complex 20-Zr

To a solution of 2.72 g (10.0 mmol) of ligand 20 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10.0 mmol) of ZrCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 30 ml of toluene. Crystals precipitated at −30° C. were collected, washed by 3×3 ml of cold toluene, 2×10 ml of hexanes, and dried in vacuum. Yield 2.12 g (49%) of a ca. 4 to 1 mixture of two isomeric complexes.

Anal. calc. for $C_{16}H_{14}Cl_2Zr$: C, 58.32; H, 4.19. Found: C, 58.37; H, 4.41.

$^1$H NMR ($CD_2Cl_2$): major isomer, δ 7.37 (d, J=8.7 Hz, 1H, 7-H in inden-2-yl), 7.29 (d, J=8.7 Hz, 1H, 6-H in inden-2-yl), 7.24 (dd, J=8.6 Hz, J=6.8 Hz, 1H, 6-H in inden-4-yl), 7.21 (s, 1H, d, J=8.6 Hz, 1H, 4-H in inden-2-yl), 6.96 (dd, J=8.6 Hz, J=1.3 Hz, 1H, 5-H in inden-4-yl), 6.86 (d, J=6.8 Hz, 1H, 7-H in inden-4-yl), 6.58 (d, J=2.0 Hz, 1H, 3-H in inden-4-yl), 6.29 (d, J=2.5 Hz, 1H, 1/3-H in inden-2-yl), 6.27 (d, J=2.0 Hz, 1H, 1-H in inden-4-yl), 4.60 (d, J=2.5 Hz, 1H, 3/1-H in inden-2-yl), 4.24 (d, J=13.4 Hz, 1H, CHH'), 3.91 (d, J=13.4 Hz, 1H, CHH'), 2.42 (s, 3H, 2-Me in inden-4-yl), 2.33 (s, 3H, 5-Me in inden-2-yl).

$^{13}C\{^1H\}$ NMR ($CD_2Cl_2$): δ 143.3, 139.4, 139.3, 138.5, 135.1, 134.1, 132.0, 130.6, 129.4, 129.3, 125.9, 124.0, 123.1, 119.6, 110.4, 108.3, 102.2, 101.4, 35.1, 23.2, 18.2.

Complex 20-Hf

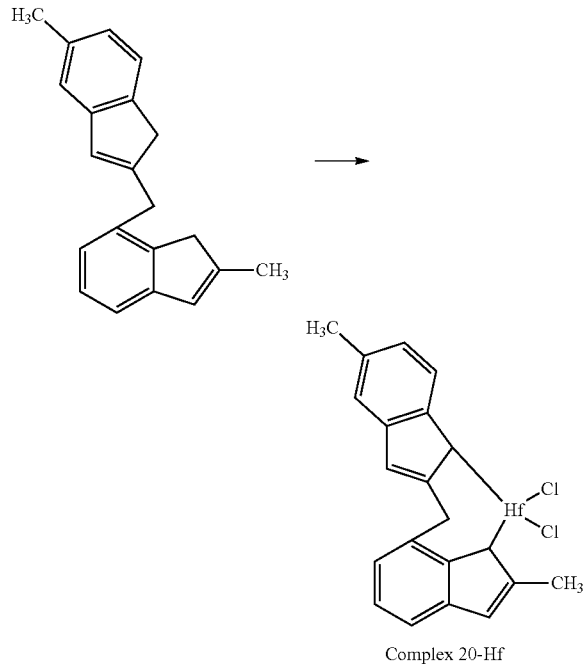

Complex 20-Hf

To a solution of 2.72 g (10.0 mmol) of ligand 20 in 200 ml of ether 8.0 ml of 2.5 M (20 mmol) of n-BuLi in hexanes was added by vigorous stirring for 5 min at room temperature. This mixture was stirred for 12 h, then cooled to −30° C., and 4.64 g (10.0 mmol) of $HfCl_4(THF)_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 30 ml of toluene. Crystals precipitated at −30° C. were collected, washed by 3×3 ml of cold toluene, 2×10 ml of hexanes, and dried in vacuum. Yield 2.12 g (49%) a ca. 2 to 1 mixture of two isomeric complexes.

Anal. calc. for $C_{16}H_{14}Cl_2Zr$: C, 48.53; H, 3.49. Found: C, 48.70; H, 3.61.

$^1$H NMR ($CD_2Cl_2$): major isomer, δ 7.36 (d, J=8.5 Hz, 1H, 7-H in inden-2-yl), 7.24 (d, J=8.5 Hz, 1H, 6-H in inden-2-yl), 7.17-7.23 (m, 2H, 6-H in inden-4-yl and 4-H in inden-2-yl), 6.93 (dd, J=8.8 Hz, J=1.3 Hz, 1H, 5-H in inden-4-yl), 6.87 (d, J=6.6 Hz, 1H, 7-H in inden-4-yl), 6.36 (d, J=2.0 Hz, 1H, 3-H in inden-4-yl), 6.18 (d, J=2.5 Hz, 1H, 1/3-H in inden-2-yl), 6.15 (d, J=2.0 Hz, 1H, 1-H in inden-4-yl), 4.41 (d, J=2.5 Hz, 1H, 3/1-H in inden-2-yl), 4.28 (d, J=13.4 Hz, 1H, CHH'), 4.24 (d, J=13.4 Hz, 1H, CHH'), 2.46 (s, 3H, 2-Me in inden-4-yl), 2.40 (s, 3H, 5-Me in inden-2-yl).

$^{13}C\{^1H\}$ NMR ($CD_2Cl_2$): δ 142.2, 140.3, 138.4, 136.4, 134.4, 133.8, 131.0, 130.6, 129.1, 129.0, 126.1, 123.7, 123.1, 119.4, 108.2, 104.8, 100.5, 98.6, 35.1, 23.1, 18.1.

Example 7

2-Methyl-4-bromo-6-tert-butylindanone-1 was obtained as described in the literature [Resconi, L.; Nifant'ev, I. E.; Ivchenko, P. V.; Bagrov, V.; Focante, F.; Moscardi, G. Int. Pat. Appl. WO2007/107448 A1].

4/7-Bromo-6/5-tert-butyl-2-methyl-1H-indene

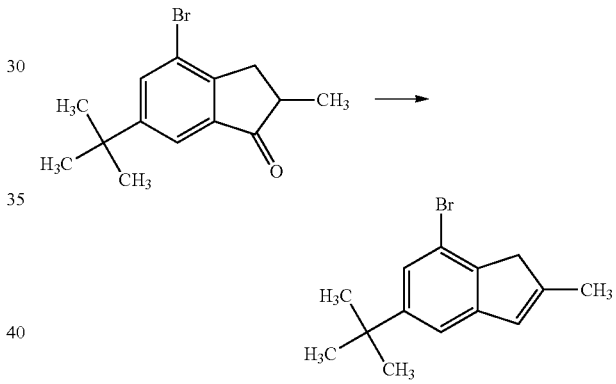

To a solution of 146 g (0.52 mol) of 4-bromo-2-methyl-1-indanone in 950 ml of THF-methanol (2:1, vol.) 38.3 g (1.02 mol) of $NaBH_4$ was added in small portions over 2 h at 0° C. The mixture was stirred overnight at ambient temperature. The resulting mixture was poured onto 1000 cm$^3$ of ice and acidified with 10% HCl to pH 4. The organic layer was separated; the aqueous layer was extracted with 3×300 ml of methyl-tert-butyl ether. This combined extract was dried over $K_2CO_3$ and evaporated to dryness, and 1500 ml of toluene were added to the residue. This toluene solution was treated with a catalytic amount of $^pTolSO_3H*H_2O$ (ca. 2 g) for 2 h at reflux. Then this mixture was cooled to room temperature and passed through a short column with Silica Gel 60 (40-63 um, d 60 mm, l 40 mm). This column was additionally eluted with 250 ml of toluene. The combined extract was evaporated to dryness. Fractional distillation gave a mixture of the title indene, b.p. 124-128° C./5 mm Hg. Yield 83 g (83%) of colorless solid.

Anal. calc. for $C_{14}H_{17}Br$: C, 63.41; H, 6.46. Found: C, 63.61; H, 6.61.

$^1$H NMR ($CDCl_3$) of 7-bromo-2-methyl-5-tert-buthyl-1H-indene: δ 7.31 (m, J=1H, 6-H), 7.28 (m, 1H, 4-H), 6.53 (m, 1H, 3-H), 3.30 (m, 2H, 1,1'-H), 2.21 (s, 3H, 2-Me), 1.39 (s, 9H, 5-C($CH_3$)$_3$).

$^{13}C\{^1H\}$ NMR (CDCl$_3$) of 7-bromo-2-methyl-5-tert-buthyl-1H-indene: δ 152.2, 147.2, 146.8, 140.4, 127.4, 123.9, 118.1, 116.1, 43.9, 34.8, 31.6, 16.8.

(6/5-tert-Butyl-2-methyl-1H-inden-4/7-yl)(chloro)dimethylsilane

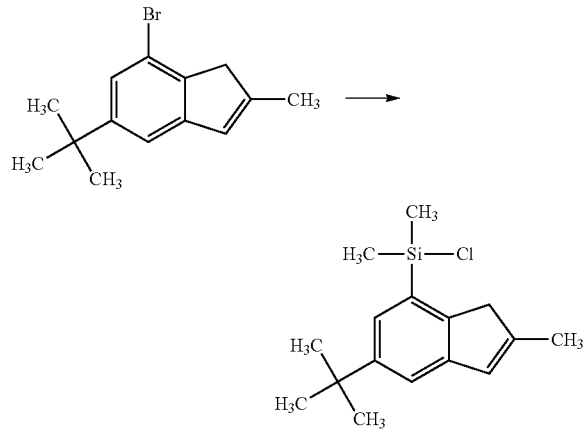

To 1.63 g (67 mmol) of magnesium turnings (activated by 0.2 ml of 1,2-dibromoethane for 10 min) in 50 ml of THF a solution of 14.6 g (55 mmol) of 2-methyl-5-tert-buthyl-7-bromoindene in 350 ml of THF was added dropwise at vigorous stirring for ca. 40 min. This mixture was additionally refluxed for 1 h, and then cooled to room temperature. The Grignard reagent obtained was added dropwise at vigorous stirring to a solution of 21.4 g (166 mmol) of dichlorodimethylsilane in 50 ml of THF for 1 h at room temperature. The resulting mixture was stirred for 12 h and then evaporated to dryness. The residue was dissolved in 100 ml of ether, and the solution obtained was filtered through glass frit (G3). The precipitate was additionally washed by 3×50 ml of ether. The combined ether solution was evaporated to dryness, and the residue was distilled in vacuum, by 130-132° C./1 mm Hg. Yield 11.0 Γ (72%).

Anal. calc. for C$_{16}$H$_{23}$ClSi: C, 68.91; H, 8.31. Found: C, 69.07; H, 8.46.

$^1$H NMR (CD$_2$Cl$_2$): δ 7.42 (m, 1H, 6-H), 7.38 (m, 1H, 4-H), 6.50 (m, 1H, 3-H), 3.43 (br.s, 2H, 1,1'-H), 2.19 (br.s, 3H, 2-Me), 1.36 (s, 9H, 5-C(CH$_3$)$_3$), 0.86 (s, 6H, Me$_2$SiCl).

(6/5-tert-Butyl-2-methyl-1H-inden-4/7-yl)(cyclopenta-2,4-dien-1-yl)dimethylsilane

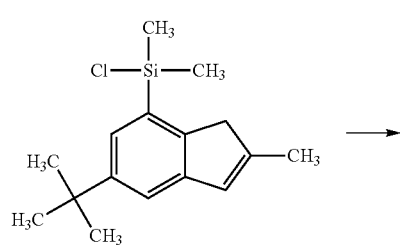

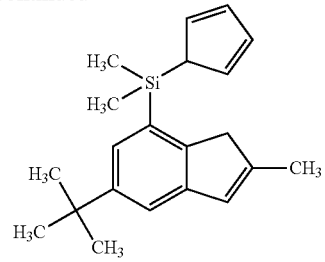

To a solution of 971 mg (13.5 mmol) of CpLi in 100 ml of THF a solution of 3.77 g (13.5 mmol) of chloro(dimethyl)(2-methyl-5-tert-buthyl-1H-inden-7-yl)silane in 10 ml of THF was added dropwise by vigorous stirring for 5 min at −80° C. This mixture was additionally stirred for 1 h at room temperature, and 1 ml of water was added. The mixture was evaporated to dryness, and 100 ml of water was added to the residue. The crude product was extracted with 3×50 ml of dichloromethane. The combined organic extract was dried over Na$_2$SO$_4$ and evaporated to dryness. The product was isolated from the residue by flash chromatography using a short column with Silica Gel 60 (40-63 um, d 60 mm, l 50 mm; eluent: hexanes). Yield 3.85 g (86%) of pure cyclopenta-2,4-dien-1-yl(dimethyl)(2-methyl-5-tert-buthyl-1H-inden-7-yl)silane.

Anal. calc. for C$_{21}$H$_{28}$Si: C, 81.75; H, 9.15. Found: C, 81.52; H, 9.09.

$^1$H NMR (CDCl$_3$): δ 7.35-7.39 (m, 2H, 4,6-H in indenyl), 6.65 (br.s, 2H, 3,4-H in Cp), 6.50-6.56 (m, 3H, 3-H in indenyl and 2,5-H in Cp), 3.78 (br.s, 1H, 1-H in Cp), 3.36 (s, 2H, 1,1'-H in indenyl), 2.19 (s, 3H, 2-Me in indenyl), 1.39 (s, 9H, C(CH$_3$)$_3$ in indenyl), 0.25 (s, 6H, SiMe$_2$).

$^{13}C\{^1H\}$ NMR (CDCl$_3$): δ 148.6, 145.9, 145.7, 145.4, 133.5 (br.), 131.7, 130.6 (br.), 127.3, 126.2, 118.3, 51.1, 43.7, 31.6, 29.7, 16.8, −3.5.

(6/5-tert-Butyl-2-methyl-1H-inden-4/7-yl)(dimethyl)(3-methyl-1H-inden-1-yl)silane

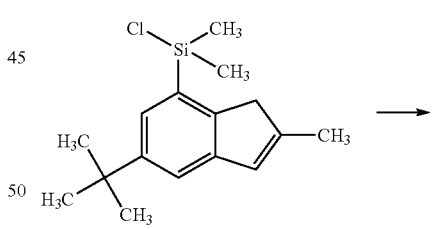

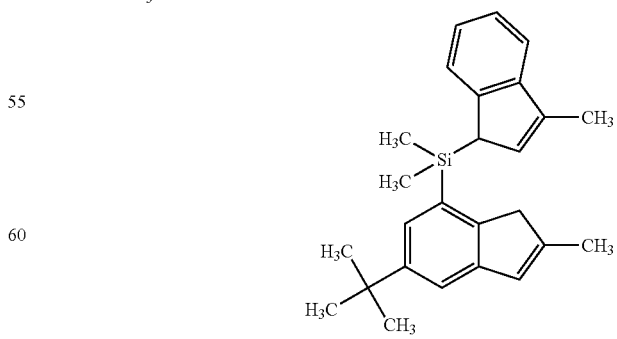

To a solution of 1.30 g (10.0 mmol) of 3-methyl-1H-indene in 90 ml of ether 4.0 ml of 2.5M (10.0 mmol) n-BuLi in hexanes was added at 0° C. This mixture was stirred for 12 h at room temperature, cooled to −50° C., and 449 mg (5.0 mmol) of CuCN was added. The resulting mixture was stirred for 1 h at −30° C., cooled to −80° C., and a solution of 2.79 g (10.0 mmol) of chloro(dimethyl)(2-methyl-5-tert-buthyl-1H-inden-7-yl)silane in 15 ml of ether was added dropwise by vigorous stirring for 10 min. This mixture was stirred for 12 h at room temperature, and then 1 ml of water was added. The mixture was stirred for 5 min and passed through short column with Silica Gel 60 (40-63 um, d 50 mm, 1 30 mm). The silica gel layer was additionally washed by 100 ml of ether. The combined elute was evaporated to dryness. The product was isolated from the residue by flash chromatography using a short column with Silica Gel 60 (40-63 um, d 60 mm, l 50 mm; eluent: hexanes). Yield 3.28 g (88%) of dimethyl(2-methyl-5-tert-buthyl-1H-inden-7-yl)(3-methyl-1H-inden-1-yl)silane.

Anal. calc. for $C_{26}H_{32}Si$: C, 83.81; H, 8.66. Found: C, 83.62; H, 8.75.

$^1$H NMR (CDCl$_3$): δ 7.39-7.44 (m, 2H, 4,7-H in 3-methylinden-1-yl), 7.24-7.33 (m, 2H, 4,5-H in 2-methyl-5-tert-buthylinden-7-yl), 7.12-7.15 (m, 2H, 5,6-H in 3-methylinden-1-yl), 6.55 (m, 1H, 3-H in 2-methyl-5-tert-buthylinden-7-yl), 6.32 (m, 1H, 2-H in 3-methylinden-1-yl), 3.76 (m, 1H, 1-H in 3-methylinden-1-yl), 3.32 (m, 2H, 1,1'-H in 2-methyl-5-tert-buthylinden-7-yl), 2.25 (s, 3H, Me in 3-methylinden-1-yl), 2.20 (s, 3H, Me in 2-methyl-5-tert-buthylinden-7-yl), 1.39 (s, 9H, 5-C(CH$_3$)$_3$), 0.27 (s, 3H, SiMeMe'), 0.22 (s, 3H, SiMeMe').

$^{13}$C{$^1$H} NMR (CDCl$_3$): δ 148.4, 146.0, 145.8, 145.5, 145.4, 145.3, 137.4, 131.1, 130.6, 127.3, 126.7, 124.7, 123.5, 123.1, 118.8, 118.2, 43.8, 43.5, 34.6, 31.6, 16.7, 12.9, −3.3, −4.1.

Complex 21-Zr

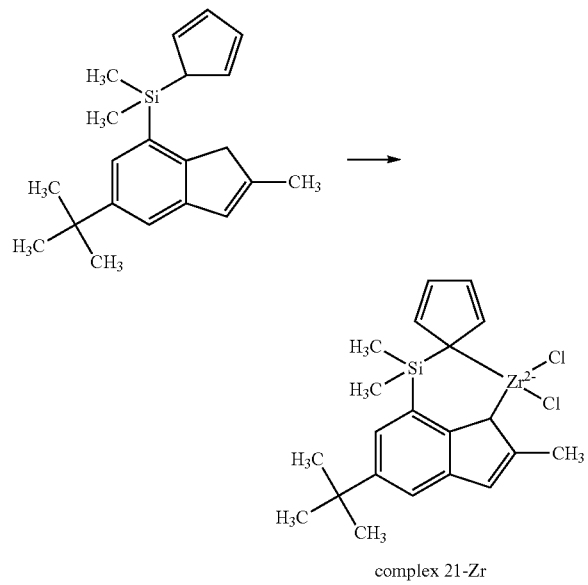

complex 21-Zr

To a solution of 3.09 g (10.0 mmol) of (6/5-tert-butyl-2-methyl-1H-inden-4/7-yl)(cyclopenta-2,4-dien-1-yl)dimethylsilane in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of ZrCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 15 ml of toluene. Crystals precipitated at −30° C. were collected, washed by 3×2 ml of cold toluene, 2×10 ml of hexanes, and dried in vacuum. Yield 2.25 g (48%).

Anal. calc. for $C_{21}H_{26}Cl_2SiZr$: C, 53.82; H, 5.59. Found: C, 54.03; H, 5.70.

$^1$H NMR (CD$_2$Cl$_2$): δ 7.52 (m, 1H, 7-H in indenyl), 7.21 (m, 1H, 5-H in indenyl), 6.82 (m, 1H, C$_5$H$_4$), 6.60 (m, 1H, C$_5$H$_4$), 6.49 (m, 1H, 3-H in indenyl), 6.36 (m, 1H, 1-H in indenyl), 6.29 (m, 1H, C$_5$H$_4$), 5.37 (m, 1H, C$_5$H$_4$), 2.29 (s, 3H, 2-Me in indenyl), 1.34 (s, 9H, 6-C(CH$_3$)$_3$ in indenyl), 0.92 (s, 3H, SiMeMe'), 0.64 (s, 3H, SiMeMe').

$^{13}$C{$^1$H} NMR (CD$_2$Cl$_2$): δ 150.2, 140.6, 134.6, 132.6, 126.7, 126.1, 124.7, 120.6, 119.5, 118.3, 117.8, 112.4, 108.8, 98.4, 34.9, 30.8, 16.8, −3.3, −4.5.

Complex 21-Hf

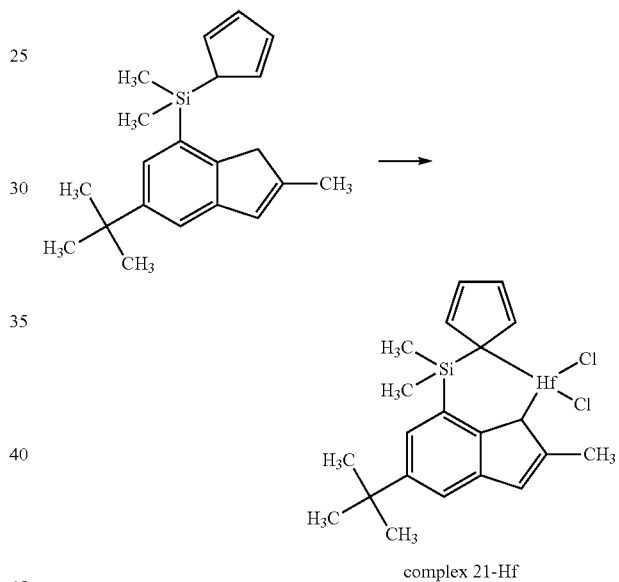

complex 21-Hf

To a solution of 3.09 g (10.0 mmol) of (6/5-tert-butyl-2-methyl-1H-inden-4/7-yl)(cyclopenta-2,4-dien-1-yl)dimethylsilane in 200 ml of ether 8.0 ml of 2.5 M (20 mmol) of n-BuLi in hexanes was added by vigorous stirring for 5 min at room temperature. This mixture was stirred for 12 h, then cooled to −30° C., and 4.64 g (10 mmol) of HfCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 15 ml of toluene. Crystals precipitated at −30° C. were collected, washed by 3×2 ml of cold toluene, 2×10 ml of hexanes, and dried in vacuum. Yield 2.56 g (46%).

Anal. calc. for $C_{21}H_{26}Cl_2SiHf$: C, 45.37; H, 4.71. Found: C, 45.55; H, 4.86.

$^1$H NMR (CD$_2$Cl$_2$): δ 7.49 (m, 1H, 7-H in indenyl), 7.23 (m, 1H, 5-H in indenyl), 6.73 (m, 1H, C$_5$H$_4$), 6.52 (m, 1H, C$_5$H$_4$), 6.31 (m, 1H, 3-H in indenyl), 6.24 (m, 1H, 1-H in indenyl), 6.22 (m, 1H, C$_5$H$_4$), 5.27 (m, 1H, C$_5$H$_4$), 2.38 (s, 3H, 2-Me in indenyl), 1.36 (s, 9H, 6-C(CH$_3$)$_3$ in indenyl), 0.92 (s, 3H, SiMeMe'), 0.66 (s, 3H, SiMeMe').

$^{13}$C{$^1$H} NMR (CD$_2$Cl$_2$): δ 149.8, 139.5, 134.0, 133.6, 126.6, 124.4, 122.6, 119.4, 119.0, 117.3, 116.4, 111.5, 106.5, 96.3, 34.8, 30.8, 16.7, −3.3, −4.4.

Complex 22-Zr

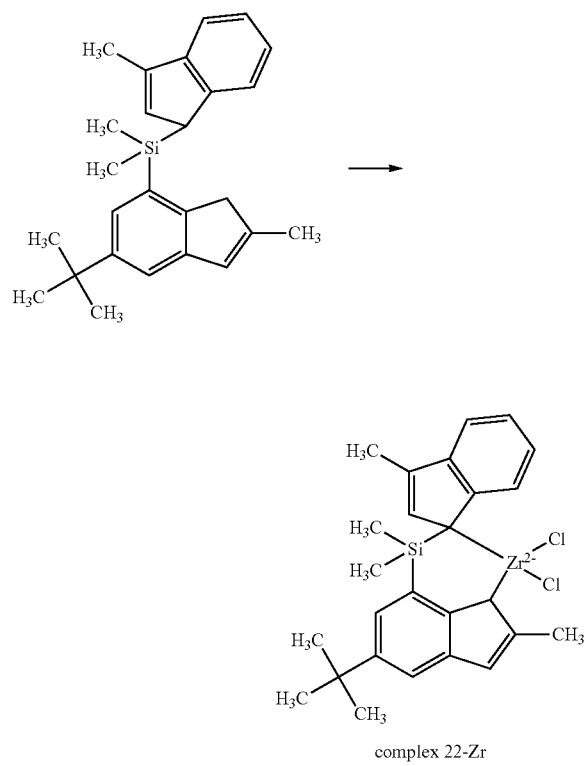

complex 22-Zr

To a solution of 3.73 g (10.0 mmol) of (6/5-tert-butyl-2-methyl-1H-inden-4/7-yl)(dimethyl)(3-methyl-1H-inden-1-yl)silane in 200 ml of ether 8.0 ml of 2.5 M (20 mmol) of n-BuLi in hexanes was added by vigorous stirring for 5 min at room temperature. This mixture was stirred for 12 h, then cooled to −30° C., and 3.77 g (10 mmol) of ZrCl$_4$(THF)$_2$. The resulting mixture was stirred for 24 h at room temperature and then evaporated to dryness. A mixture of the residue obtained and 200 ml of toluene was stirred for 6 h at 80° C. and then filtered through glass frit (G4). The precipitate was additionally washed by 3×50 ml of hot toluene. The combined extract was evaporated to dryness, and the residue was re-crystallized from 30 ml of toluene. Crystals precipitated at −30° C. were collected, washed by 3×4 ml of cold toluene, 2×7 ml of hexanes, and dried in vacuum. Yield 2.61 g (49%) of one pure isomer.

Anal. calc. for C$_{26}$H$_{30}$Cl$_2$SiZr: C, 58.62; H, 5.68. Found: C, 58.89; H, 5.79.

$^1$H NMR (CD$_2$Cl$_2$): δ 7.35-7.40 (m, 3H, 5,7-H in 2-methylindenyl and 4-H in 3-methylindenyl), 7.10 (m, 1H, 5-H in 3-methylinden-1-yl), 6.88 (m, 1H, 6-H in 3-methylinden-1-yl), 6.75 (d, J=7.6 Hz, 7-H in 3-methylindenyl) 6.48 (m, 1H, 3-H in 2-methylindenyl), 6.45 (m, 1H, 1-H in 2-methylindenyl), 6.27 (m, 1H, 2-H in 3-methylindenyl), 2.49 (s, 3H, Me in 3-methylinden-1-yl), 2.24 (s, 3H, Me in 2-methylinden), 1.34 (s, 9H, 5-C(CH$_3$)$_3$ in 2-methylindenyl), 1.02 (s, 3H, SiMeMe'), 0.89 (s, 3H, SiMeMe').

$^{13}$C{$^1$H} NMR (CD$_2$Cl$_2$): δ 149.9, 139.7, 133.8, 132.1, 131.3, 129.3, 127.0, 126.6, 126.4, 126.1, 125.8, 123.5, 121.0, 119.3, 117.4, 108.7, 99.2, 98.9, 34.8, 30.6, 16.8, 13.7, −1.9, −4.0.

Example 8

4-Bromo-6-tertbutyl-1-methoxy-2-methylindane

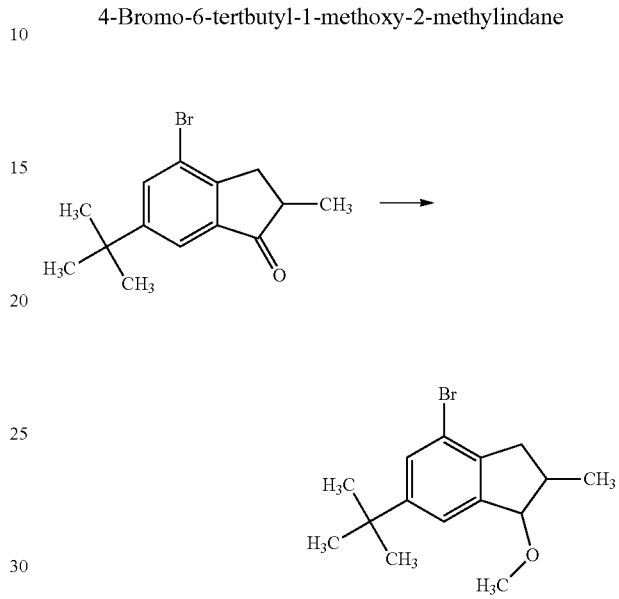

To a solution of 104 g (0.37 mol) of 4-bromo-6-tert-buthyl-1-indanone in 800 ml of THF-methanol (2:1, vol.) 22.5 g (0.592 mol) of NaBH$_4$ was added in small portions with vigorous stirring over 1.5 h at 5° C. This mixture was stirred at room temperature for 12 h and then added to 1500 cm$^3$ of cold water. The hydrogenation product was extracted with 3×300 ml of dichloromethane, and the combined extract was evaporated to dryness. To 62 g (1.11 mol) of KOH in 510 ml of DMSO, 131 g (0.92 mol) MeI and a solution of crude 4-bromo-6-tertbuthylindan-1-ol in 150 ml of DMSO were added. This mixture was stirred for 4 h at ambient temperature. The resulting mixture was added to 2 L of cold water. The crude product was extracted with 4×400 ml of dichloromethane. The combined extract was dried over Na$_2$SO$_4$ and then evaporated to dryness. Fractional distillation gave a mixture of two diastereomeric compounds, b.p. 121° C./3 mm Hg. Yield 87.2 g (79%) of colorless oil of pure 4-bromo-6-tertbutyl-1-methoxy-2-methylindane of a ca. 1 (trans-isomer) to 2 (cis-isomer) mixture of two diastereomers.

Anal. calc. for C$_{15}$H$_{21}$BrO: C, 60.61; H, 7.12. Found: C, 60.60; H, 7.13.

$^1$H NMR (CDCl$_3$): δ 7.43 (s, 1H, cis-product), 7.41 (s, 1H, trans-product), 7.31 (s, 1H, cis-product), 7.30 (s, 1H, trans-product), 4.57 (d, J=5.31 Hz, 1H, CHOMe of trans-product), 4.43 (d, J=4.30 Hz, 1H, CHOMe of cis-product), 3.45 (s, 3H, OMe of cis-product), 3.42 (m, 3H, OMe of trans-product), 3.18 (dd, J=16.17 Hz, J=7.08 Hz, 1H, CHMe cis-product), 2.94-2.87 (m, 1H, CHMe trans-product), 2.67-2.63 (m, 2H, CH$_2$ of trans-product), 2.54-2.48 (m, 1H, CHHCHMe of cis-product), 2.40 (dd, J=16.17 Hz, J=5.31 Hz, 1H, CHHCHMe of cis-product), 1.31 (s, 9H, tBu of both isomers), 1.18 (d, J=7.08 Hz, 3H, CHMe of cis-product), 1.08 (d, J=6.82 Hz, 3H, CHMe of trans-product).

2-(6-tert-Butyl-1-methoxy-2-methyl-2,3-dihydro-1H-inden-4-yl)ethanol

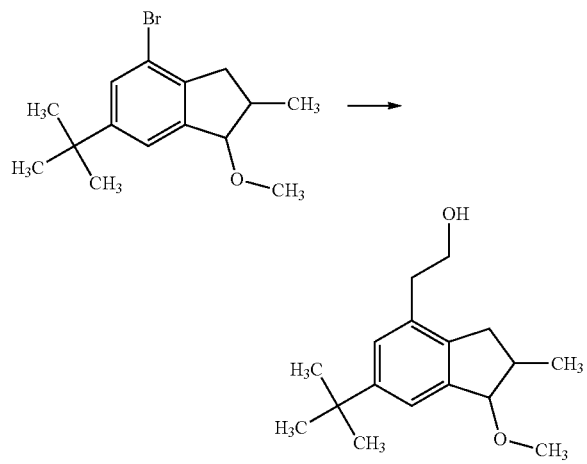

To a solution of 40.0 g (134.5 mmol) of 4-bromo-6-tert-butyl-1-methoxy-2-methylindane in 250 ml of THF 107.7 ml of 2.5 M (269 mmol) n-BuLi in hexanes was added for 20 min at −80° C. This mixture was stirred for 40 min at this temperature, cooled to −110° C., and 11.85 g (269.15 mmol) of ethylene oxide was added by one portion at vigorous stirring. The resulting mixture was stirred for 12 h at room temperature, and then 10 ml of water was added. The organic layer was separated and evaporated to dryness. To the residue 200 ml of water was added, and the crude product was extracted with 3×100 ml of dichloromethane. The combined organic extract was dried over $Na_2SO_4$ and evaporated to dryness. The product was isolated by flash chromatography using short column with Silica Gel 60 (40-63 um, d 110 mm, l 90 mm; eluent: hexanes/ether=20/1). Yield 27.58 g (78%) of a ca. 1 to 2 mixture of two diastereomers.

Anal. calc. for $C_{17}H_{26}O_2$: C, 77.82; H, 9.99. Found: C, 77.84; H, 9.95.

$^1$H NMR ($CDCl_3$): δ 7.28 (s, 1H, of both isomers), 7.14 (s, 1H, of both isomers), 4.50 (d, J=5.30 Hz, 1H, CHOMe of minor isomer), 4.39 (d, J=4.29 Hz, 1H, CHOMe of major isomer), 3.78 (m, CH2, Ch2CH2 both), 3.47 (s, 3H, OMe of major isomer), 3.42 (s, 3H, OMe of minor isomer), 3.19-3.15 (m, 1H, CHCH$_3$ of both isomers), 2.82 (m, 2H, CH$_2$CH$_2$ of both isomers), 2.65-2.60 (m, 1H, CH$_2$CHCH3 of both isomers), 2.37 (m, 1H, CH$_2$CHCH3 of both isomers), 1.32 (s, 9H, tBu of both isomers), 1.17 (d, J=7.07 Hz, 3H, Me in MeCH of major isomer), 1.10 (d, J=6.56 Hz, 3H, Me in MeCH of minor isomer).

$^{13}C\{^1H\}$ NMR ($CDCl_3$): δ 150.14, 149.76, 142.80, 142.28, 139.49, 139.12, 135.92, 133.92, 126.43, 126.18, 120.40, 120.32, 91.79, 85.48, 62.78, 62.71, 56.91, 56.50, 39.60, 38.55, 36.98, 36.88, 36.71, 36.39, 31.61, 19.7, 13.80.

4-(2-Bromoethyl)-6-tert-butyl-1-methoxy-2-methylindane

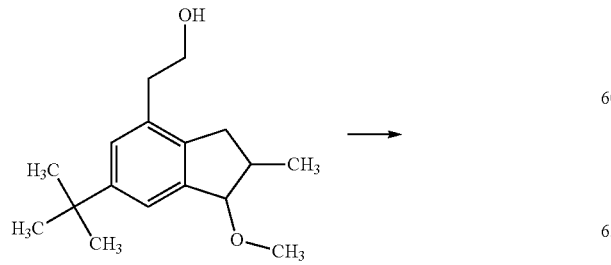

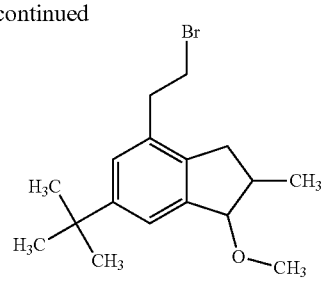

To a mixture of 27.58 g (105 mmol) of 2-(6-tert-butyl-1-methoxy-2-methyl-2,3-dihydro-1H-inden-4-yl)ethanol and 27.58 g (105 mmol) PPh$_3$ in 450 ml of THF 18.72 g (105 mmol) of NBS was added at vigorous stirring for 5 min at 0° C. This mixture was stirred for 2 h at room temperature and then evaporated to dryness. A solution of the residue in 500 ml of hexanes was filtered through glass frit (G3), and the precipitate was additionally washed by 3×300 ml hexanes. The combined organic extract was evaporated to dryness. The product was isolated from the residue using flash chromatography on Silica Gel 60 (40-63 um, d 80 mm, 1250 mm; eluent: hexanes/ether=20/1, vol.). Yield 25.48 g (74%) of ca. 1 to 2 mixture of diastereomers.

Anal. calc. for $C_{17}H_{25}BrO$: C, 62.77; H, 7.75; Br, 24.56. Found: C, 62.74; H, 7.78; Br, 24.53.

$^1$H NMR ($CDCl_3$): δ 7.35 (s, 1H, of both isomers), 7.18 (s, 1H, of both isomers), 4.55 (d, J=5.56 Hz, 1H, CHOMe of minor isomer), 4.44 (d, J=4.04 Hz, 1H, CHOMe of major isomer), 3.55 (t, J=8.08 Hz, 2H, CH$_2$CH$_2$ both), 3.51 (s, 3H, OMe of major isomer), 3.46 (s, 3H, OMe of minor isomer), 3.21 (m, 1H, CHCH$_3$ of both isomers), 3.16 (t, J=8.08 Hz, 2H, CH$_2$CH$_2$ of both isomers), 2.56 (m, 1H, CH$_2$CHCH$_3$ of both isomers), 2.40 (m, 1H, CH$_2$CHCH$_3$ of both isomers), 1.327 (s, 9H, t-Bu of both isomers), 1.22 (d, J=6.82 Hz, 3H, Me in MeCH of major isomer), 1.15 (d, J=6.57 Hz, 3H, Me in MeCH of minor isomer).

2-[2-(6-tert-Butyl-1-methoxy-2-methyl-2,3-dihydro-1H-inden-4-yl)ethyl]indan-2-ol

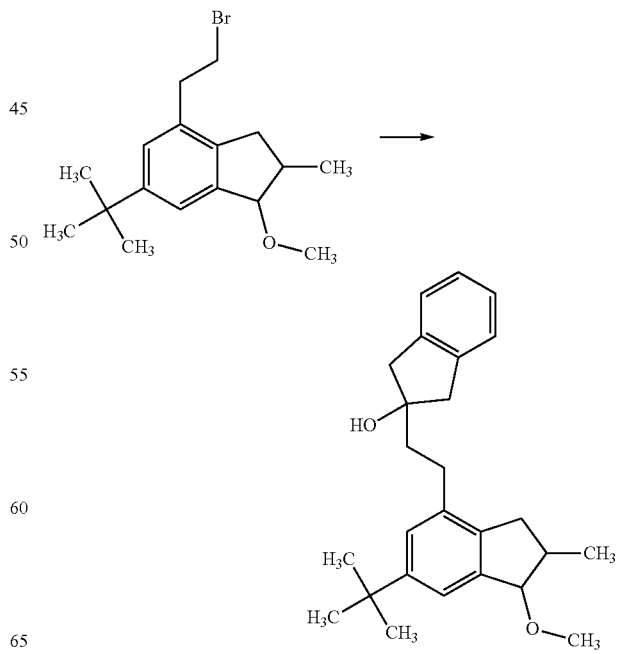

8.59 g (34.84 mmol) of anhydrous CeCl₃ was added to 127 ml of THF at 0° C. This mixture was stirred at room temperature overnight. In another flask, to 0.85 g (34.84 mmol) of magnesium turnings in 80 ml of THF 11.33 g (34.84 mmol) of 4-(2-bromoethyl-6-tert-butyl-1-methoxy-2-methylindane was added dropwise for 30 minutes at reflux. The resulting mixture was refluxed for 2 hours, cooled to 0° C., and then added to a suspension of CeCl₃ in THF. The resulting mixture was stirred for 2 h at room temperature, then cooled to 0° C., and 4.60 g (34.83 mmol) of indanone-2 was added. This mixture was stirred overnight at room temperature, evaporated to dryness. To the residue a mixture of AcOH (20 ml) and water (100 ml) was added. The crude product was extracted by 3×150 ml of CH₂Cl₂. The combined extract was evaporated to dryness. The product was isolated by flash chromatography using a short column with Silica Gel 60 (40-63 um, d 60 mm, 170 mm; eluent: hexanes/ether=3/1). Yield 5.78 g (44%) of pure 2-[2-(6-ten-butyl-1-methoxy-2-methyl-2,3-dihydro-1H-inden-4-yl)ethyl]indan-2-ol as single diastereomer.

Anal. calc. for C₂₆H₃₄O₂: C, 82.49; H, 9.05. Found: C, 82.44; H, 9.07.

¹H NMR (CDCl₃): δ 7.14-7.07 (m, 6H), 4.57 (s, 1H, OH), 4.30 (d, J=3.79 Hz, 1H, CHOMe), 3.35 (s, 3H, OMe), 3.03 (m, 1H, CHMe), 2.97-2.84 (m, 4H, 2CH₂ in indane), 2.63 (m, 2H, CH₂ in CH₂CH₂), 2.49 (m, 2H, CH₂CHMe), 1.81 (m, 2H, CH₂ in CH₂CH₂), 1.24 (s, 9H, tBu), 1.07 (d, J=6.82 Hz, 3H, Me).

6/5-tent-Butyl-4/7-[2-(1H-inden-2-yl)ethyl]-2-methyl-1H-indene

To a hot (110° C.) solution of 5.2 g (13.74 mmol) of 2-[2-(6-ten-butyl-1-methoxy-2-methyl-2,3-dihydro-1H-inden-4-yl)ethyl]indan-2-ol in 110 ml of toluene 0.581 g (3.05 mmol) of TsOH*H₂O was added. This mixture was refluxed with a Dean-Stark trap for 40 min, and then passed through short column with Silica Gel 60 (40-63 um, d 80 mm, 1 60 mm). The column was additionally washed with 300 ml of toluene. The combined elute was evaporated to dryness. The product was isolated by flash chromatography using a short column with Silica Gel 60 (40-63 um, d 60 mm, 1 70 mm; eluent: hexanes/ether=50/1). Yield 3.52 g (78%) of pure 6/5-tert-butyl-4/7-[2-(1H-inden-2-yl)ethyl]-2-methyl-1H-indene.

Anal. calc. for C₂₄H₂₀: C, 91.41; H, 8.59. Found: C, 91.46; H, 8.54.

¹H NMR (CDCl₃): δ 7.45 (m, 1H), 7.35 (m, 1H), 7.30 (d, J=7.07 Hz, 1H), 7.26 (s, 1H), 7.18 (d, J=6.32 Hz, 1H), 7.08 (s, 1H), 6.66 (s, 1H), 6.55 (s, 1H), 3.42 (s, 2H), 3.30 (s, 2H), 3.03 (m, 2H), 2.91 (m, 2H), 2.22 (s, 3H, Me), 1.40 (s, 9H, t-Bu).

¹³C NMR (CDCl₃): δ 150.24, 150.02, 145.91, 145.54, 143.03, 138.57, 135.67, 127.68, 126.44, 126.23, 123.63, 123.66, 123.38, 120.80, 119.87, 114.97, 41.24, 40.94, 34.62, 33.22, 31.76, 31.67, 16.81.

Complex 23-Hf

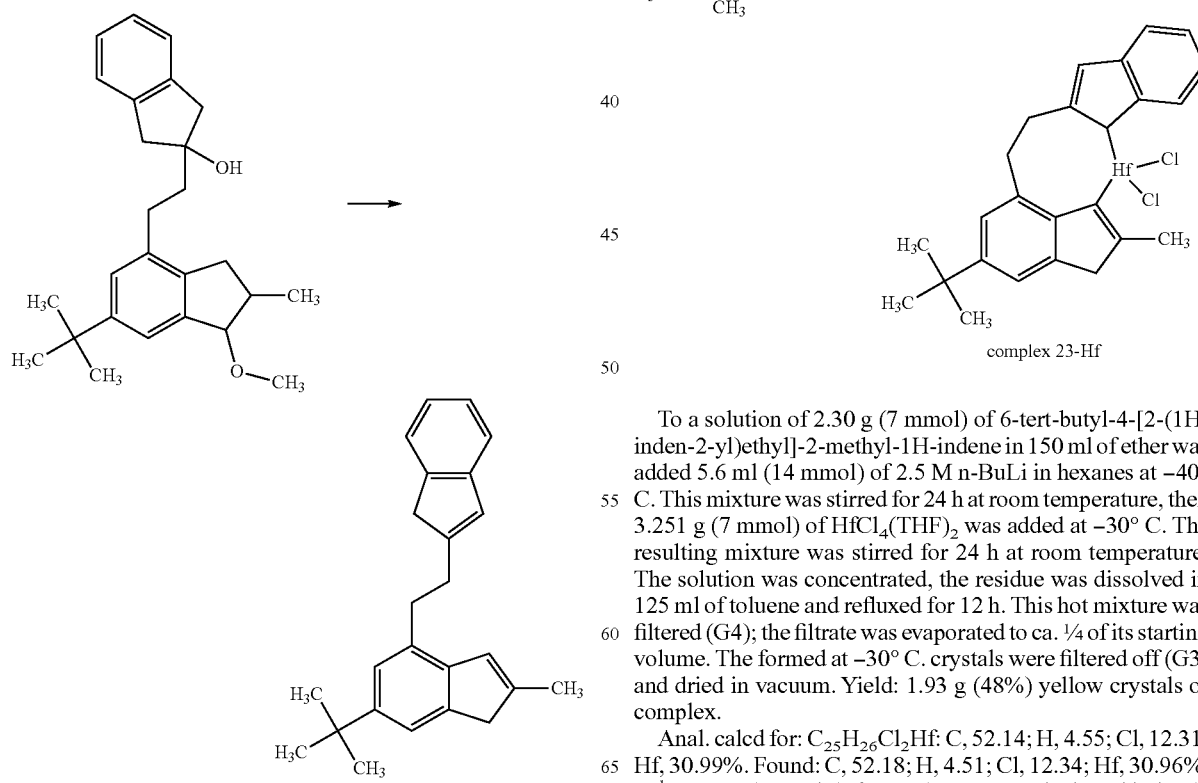

complex 23-Hf

To a solution of 2.30 g (7 mmol) of 6-tert-butyl-4-[2-(1H-inden-2-yl)ethyl]-2-methyl-1H-indene in 150 ml of ether was added 5.6 ml (14 mmol) of 2.5 M n-BuLi in hexanes at −40° C. This mixture was stirred for 24 h at room temperature, then 3.251 g (7 mmol) of HfCl₄(THF)₂ was added at −30° C. The resulting mixture was stirred for 24 h at room temperature. The solution was concentrated, the residue was dissolved in 125 ml of toluene and refluxed for 12 h. This hot mixture was filtered (G4); the filtrate was evaporated to ca. ¼ of its starting volume. The formed at −30° C. crystals were filtered off (G3) and dried in vacuum. Yield: 1.93 g (48%) yellow crystals of complex.

Anal. calcd for: C₂₅H₂₆Cl₂Hf: C, 52.14; H, 4.55; Cl, 12.31; Hf, 30.99%. Found: C, 52.18; H, 4.51; Cl, 12.34; Hf, 30.96%.

¹H NMR (CD₂Cl₂.): δ 7.57 (m, 1H, unsubstituted indene), 7.38 (s, 1H, t-Bu-indene), 7.24 (s, 1H, t-Bu-indene), 7.09 (m, 3H, unsubstituted indene), 6.15 (s, 1H, Cp), 5.96 (s, 1H, Cp), 5.94 (s, 1H, Cp), 4.24 (s, 1H, Cp), 3.78 (m, 1H, CH$_2$), 3.63 (m, 1H, CH$_2$), 3.47 (m, 1H, CH$_2$), 3.32 (m, 1H, CH$_2$), 2.4 (s, 3H, Me), 1.38 (s, 9H, tBu).

$^{13}$C NMR (CD$_2$Cl$_2$): δ 149.53, 140.35, 135.5, 135.12, 129.46, 127.92, 126.75, 117.99, 125.39, 125.07, 124.95, 124.63, 123.92, 117.5, 107.8, 102.34, 99.14, 96.29, 34.9, 30.74, 29.29, 26.61, 16.97.

Example 9

2,5,6-Trimethylindan-1-one

To a suspension of 557 g (4.2 mol) AlCl$_3$ in 500 ml of CH$_2$Cl$_2$ 362 g (1.58 mol) of 2-bromo-2-methylpropanoyl bromide was added dropwise with vigorous stirring over 15 min at 0° C. This mixture was stirred for 45 min at this temperature; then, a solution of 167 g (1.58 mol) of o-xylene in 200 ml of CH$_2$Cl$_2$ was added dropwise. The mixture was slowly warmed to ambient temperature, stirred additionally overnight, and then poured onto 2000 cm$^3$ of ice. The organic layer was separated, and the aqueous layer was extracted with 3×500 ml of CH$_2$Cl$_2$. The combined extract was dried over MgSO$_4$ and evaporated to dryness. Fractional distillation gave a yellowish mixture of the title indanones, b.p. 143-148° C./7 mm Hg. This mixture was recrystallized from 800 ml of n-hexane. Crystals of 2,5,6-trimethylindan-1-one precipitated at −30° C. were filtered off, washed with 2×40 ml of cold n-hexane, and dried in vacuum. Yield 57.8 g (21%) of 2,5,6-trimethylindan-1-one.

Anal. calc. for C$_{12}$H$_{14}$O: C, 82.72; H, 8.10. Found: C, 82.74; H, 8.12.

$^1$H NMR (CDCl$_3$): δ 7.49 (s, 1H, 4-H), 7.09 (s, 1H, 7-H), 3.29 (dd, J=16.9 Hz, J=7.6 Hz, 1H, CHMe), 2.67-2.59 (m, 2H, CH$_2$), 2.32 (s, 3H, Me), 2.28 (s, 3H, Me), 1.27 (d, J=7.6 Hz, MeCH).

4-Bromo-2,5,6-trimethylindan-1-one

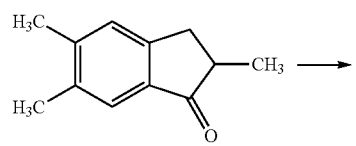

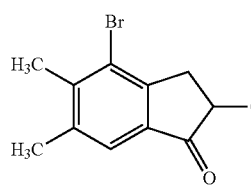

In a three-necked round-bottom 500-ml flask equipped with a reflux condenser, a dropping funnel with a pressure-equalizing bypass, and a mechanical stirrer, to a suspension of 53 g (0.398 mol) of AlCl$_3$ in 60 ml of CH$_2$Cl$_2$ a solution of 57.8 g (0.332 mol) of 2,5,6-trimethylindanone-1 in 50 ml of CH$_2$Cl$_2$ was added dropwise with vigorous stirring over 1 h at −10° C. This mixture was stirred for an additional 1 h at this temperature; then, 17.0 ml (53.0 g, 0.332 mol) of bromine was added dropwise with vigorous stirring over 1 h. The resulting mixture was stirred for 2 h at −10° C. and overnight at ambient temperature and then poured into 1000 cm$^3$ of cold water. The organic layer was separated, and the aqueous layer was extracted with 3×200 ml of methyl-tert-butyl ether. The combined extract was washed with saturated aqueous Na$_2$SO$_3$ to eliminate bromine and then with aqueous Na$_2$CO$_3$, dried over K$_2$CO$_3$, and evaporated to dryness. Fractional distillation gave a yellowish liquid, b.p. 155-158° C./4 mm Hg. Yield 61.6 g (73%).

Anal. calc. for C$_{12}$H$_{13}$BrO: C, 56.94; H, 5.18. Found: C, 56.91; H, 5.16.

$^1$H NMR (CDCl$_3$): δ 7.03 (s, 1H, 7-H), 2.91 (dd, J$_1$=17.43 Hz, J$_2$=7.58 Hz, 1H, CHMe), 2.24 (d, J=17.43 Hz, 1H, CHH), 2.14 (d, J=17.43 Hz, 1H, CHH), 2.09 (s, 3H, Me), 2.06 (s, 3H, Me), 1.04 (d, J=7.58 Hz, 3H, CHMe).

$^{13}$C{$^1$H} NMR (CDCl$_3$): δ 207.0, 150.74, 142.81, 137.32, 134.8, 123.8, 122.4, 41.44, 36.1, 20.73, 19.3, 15.6.

4-Bromo-1-methoxy-2,5,6-trimethylindane

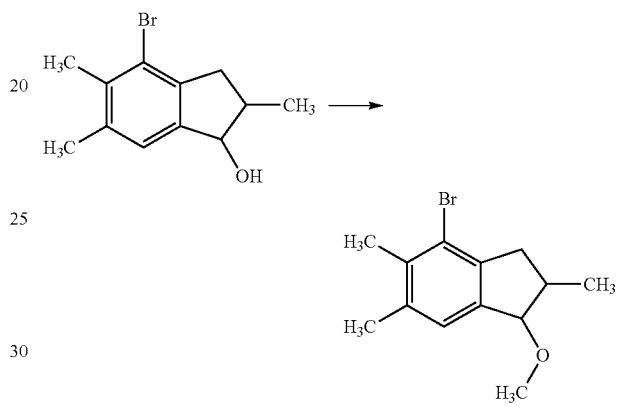

To a solution of 61.6 g (0.243 mol) of 4-bromo-2,5,6-trimethyl-1-indanone in 600 ml of THF-methanol (2:1, vol.) 14.71 g (0.389 mol) of NaBH$_4$ was added in small portions with vigorous stirring over 1.5 h at 5° C. This mixture was stirred at room temperature for 12 h and then added to 1500 cm$^3$ of cold water. The hydrogenation product was extracted with 3×200 ml of dichloromethane, and the combined extract was evaporated to dryness. To 54.43 g (0.972 mol) of KOH in 420 ml of DMSO, 68.7 g (30.15 ml, 0.486 mol) MeI and a solution of crude 4-bromo-2,5,6-trimethylindan-1-ol in 100 ml of DMSO were added. This mixture was stirred for 2 h at ambient temperature; then, 92.0 g (15.07 ml, 0.243 mol) of MeI was added, and the mixture was additionally stirred for 2 h. The resulting mixture was added to 1.5 L of cold water. The crude product was extracted with 4×200 ml of dichloromethane. The combined extract was dried over Na$_2$SO$_4$ and then evaporated to dryness. Fractional distillation gave a mixture of two diastereomeric compounds, b.p. 115° C./3 mm Hg. Yield 59.5 g (91%) of colorless oil of pure 4-Bromo-1-methoxy-2,5,6-trimethylindane of a ca. 2 (trans-isomer) to 3 (cis-isomer) mixture of two diastereomers.

Anal. calc. for C$_{13}$H$_{17}$BrO: C, 58.01; H, 6.37. Found: C, 58.00; H, 6.38.

$^1$H NMR (CDCl$_3$): δ 7.13 (s, 1H, 7-H of cis-product), 7.11 (s, 1H, 7-H of trans-product), 4.56 (d, J=5.81 Hz, 1H, CHOMe of trans-product), 4.43 (d, J=3.79 Hz, 1H, CHOMe of cis-product), 3.45 (m, 3H, OMe of cis-product), 3.41 (m, 3H, OMe of trans-product), 3.27-3.42 (m, 1H, CHMe of cis-product), 2.99-2.93 (m, 1H, CHMe of trans-product), 2.73-2.58 (m, 1H, CHHCHMe of both isomers), 2.54-2.42 (m, 1H, CHHCHMe of both isomers), 2.37 (s, 3H, Me in both isomers), 2.34 (s, 3H, Me in both isomers), 1.18 (d, J=7.07 Hz, 3H, CHMe of cis-product), 1.12 (d, J=6.83 Hz, 3H, CHMe of trans-product).

$^{13}$C{$^1$H} NMR (CDCl$_3$), major isomer: δ 141.6, 140.5, 136.6, 136.05, 125.48, 123.5, 92.25, 56.4, 40.85, 39.0, 21.45, 19.58, 13.65.

2-(1-Methoxy-2,5,6-trimethyl-2,3-dihydro-1H-inden-4-yl)ethanol

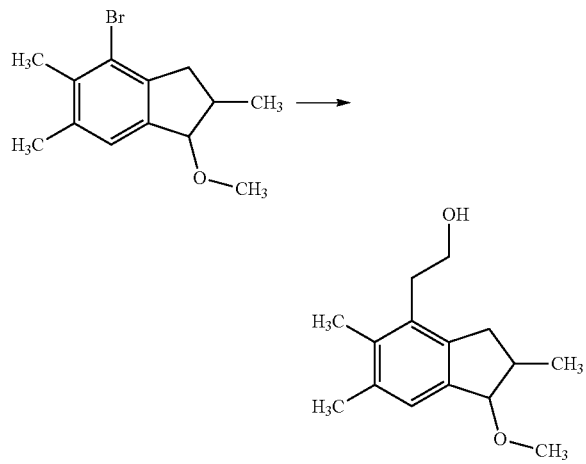

To a solution of 52.77 g (196.0 mmol) of 4-bromo-1-methoxy-2,5,6-trimethylindane in 300 ml of THF 156.8 ml of 2.5 M (392.1 mmol) n-BuLi in hexanes was added for 20 min at −80° C. This mixture was stirred for 40 min at this temperature, cooled to −110° C., and 17.27 g (392.1 mmol) of ethylene oxide was added by one portion at vigorous stirring. The resulting mixture was stirred for 12 h at room temperature, and then 10 ml of water was added. The organic layer was separated and evaporated to dryness. To the residue 200 ml of water was added, and the crude product was extracted with 3×100 ml of dichloromethane. The combined organic extract was dried over $Na_2SO_4$ and evaporated to dryness. The product was isolated by flash chromatography using short column with Silica Gel 60 (40-63 um, d 110 mm, l 90 mm; eluent: hexanes/ether=20/1). Yield 36.66 g (80%) of a ca. 1 to 1.7 mixture of two diastereomers.

Anal. calc. for $C_{15}H_{22}O_2$: C, 76.88; H, 9.46. Found: C, 76.86; H, 9.45.

$^1$H NMR (CDCl$_3$): δ 7.09 (s, 1H, of minor isomer), 7.07 (s, 1H, of major isomer), 4.46 (d, J=5.581 Hz, 1H, CHOMe of minor isomer), 4.34 (d, J=3.53 Hz, 1H, CHOMe of major isomer), 3.71 (dt, J$_1$=7.32 Hz, J$_2$=2.53 Hz, 2H, CH$_2$OH of both isomers), 3.43 (s, 3H, OMe of major isomer), 3.39 (s, 3H, OMe of minor isomer), 3.21 (m, 1H, CHCH$_3$ of both isomers), 2.91 (dt, J$_1$=7.33 Hz, J$_2$=2.53 Hz, 2H, CH$_2$CH$_2$OH of both isomers), 2.67-2.37 (m, 2H, CH$_2$CHCH$_3$ of both isomers), 2.27 (s, 3H, Me of both isomers), 2.22 (s, 3H, Me of both isomers), 1.13 (d, J=7.07 Hz, 3H, Me in MeCH of major isomer), 1.10 (d, J=6.83 Hz, 3H, Me in MeCH of minor isomer).

$^{13}$C{$^1$H} NMR (CDCl$_3$), major isomer: δ 140.53, 139.17, 135.54, 135.06, 132.44, 125.17, 91.75, 62.02, 56.39, 39.24, 37.70, 33.86, 21.06, 19.7, 13.80.

4-(2-Bromoethyl)-1-methoxy-2,5,6-trimethylindane

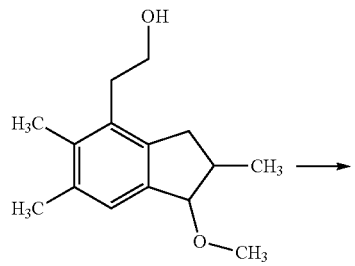

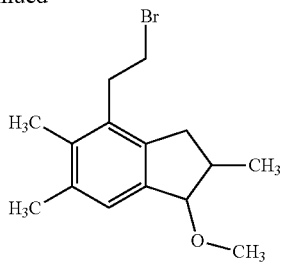

To a mixture of 36.66 g (156.44 mmol) of 2-(1-methoxy-2,5,6-trimethyl-2,3-dihydro-1H-inden-4-yl)ethanol and 41 g (156.44 mmol) PPh$_3$ in 650 ml of THF 27.85 g (156.44 mmol) of NBS was added at vigorous stirring for 5 min at 0° C. This mixture was stirred for 2 h at room temperature and then evaporated to dryness. A solution of the residue in 500 ml of hexanes was filtered through glass frit (G3), and the precipitate was additionally washed by 3×300 ml hexanes. The combined organic extract was evaporated to dryness. The product was isolated from the residue using flash chromatography on Silica Gel 60 (40-63 um, d 80 mm, 1250 mm; eluent: hexanes/ether=20/1, vol.). Yield 31.38 g (67%) of ca. 1 to 2 mixture of diastereomers.

Anal. calc. for $C_{15}H_{21}BrO$: C, 60.61; H, 7.12. Found: C, 60.64; H, 7.16.

$^1$H NMR (CDCl$_3$): δ 7.14 (s, 1H, of major isomer), 7.13 (s, 1H, of minor isomer), 4.49 (d, J=5.55 Hz, 1H, CHOMe of minor isomer), 4.37 (d, J=3.53 Hz, 1H, CHOMe of major isomer), 3.46 (s, 3H, OMe of major isomer), 3.42 (s, 3H, OMe of minor isomer), 3.43-3.38 (m, 2H, CH$_2$Br of both isomers), 3.25-3.17 (m, 2H, CH$_2$CH$_2$Br of both isomers), 2.95 (m, 1H, CH$_2$CHCH$_3$ of both isomers), 2.70-2.50 (m, 2H, CHH-CHCH$_3$ of both isomers), 2.30 (s, 3H, Me of both isomers), 2.24 (s, 3H, Me of both isomers), 1.17 (d, J=7.05 Hz, 3H, MeCH of major isomer), 1.14 (d, J=6.82 Hz, 3H, MeCH of minor isomer).

2-[2-(1-Methoxy-2,5,6-trimethyl-2,3-dihydro-1H-inden-4-yl)ethyl]indan-2-ol

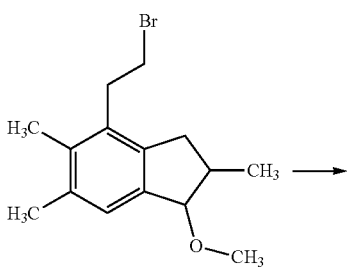

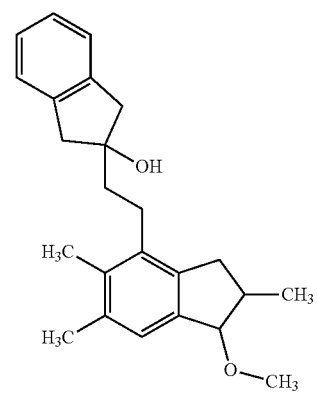

13.6 g (54.9 mmol) of anhydrous CeCl₃ was added to 200 ml of THF at 0° C. This mixture was stirred at room temperature overnight. In another flask, to 1.34 g (54.9 mmol) of magnesium turnings in 125 ml of THF 16.33 g (54.94 mmol) of 4-(2-bromoethyl-1-methoxy-2,5,6-trimethylindane was added dropwise for 30 minutes at reflux. The resulting mixture was refluxed for 2 hours, cooled to 0° C., and then added to a suspension of CeCl₃ in THF. The resulting mixture was stirred for 2 h at room temperature, then cooled to 0° C., and 7.26 g (54.94 mmol) of indanone-2 was added. This mixture was stirred overnight at room temperature, evaporated to dryness. To the residue a mixture of AcOH (30 ml) and water (170 ml) was added. The crude product was extracted by 3×200 ml of CH₂Cl₂. The combined extract was evaporated to dryness. The product was isolated by flash chromatography using a short column with Silica Gel 60 (40-63 um, d 60 mm, l 70 mm; eluent: hexanes/ether=3/1). Yield 6.60 g (40%) of pure 2-[2-(1-methoxy-2,5,6-trimethyl-2,3-dihydro-1H-inden-4-yl)ethyl]indan-2-ol of a ca. 1 to 3.5 mixture of two diastereomers.

Anal. calc. for $C_{24}H_{30}O_2$: C, 82.24; H, 8.63. Found: C, 82.26; H, 8.61.

¹H NMR (CDCl₃): δ 7.19 (m, 2H, aromatics in both isomers), 7.12 (m, 2H, aromatics in both isomers), 6.98 (s, 1H, H in 2,5,6-trimethylindane in both isomers), 4.64 (s, 1H, OH of both isomers), 4.39 (d, J=4.80 Hz, 1H, CHOMe of minor isomer), 4.27 (d, J=2.78 Hz, 1H, CHOMe of major isomer), 3.31 (s, 3H, OMe of major isomer), 3.26 (s, 3H, OMe of minor isomer), 3.09 (m, 4H, 2CH₂ in indanole fragment of minor isomer), 2.99 (d, J=16.17 Hz, 2H, CH₂ in indanole fragment of major isomer), 2.92 (d, J=16.17 Hz, 2H, CH₂ in indanole fragment of major isomer), 2.70 (m, 2H, CH₂CH₂CHOH in both isomers), 2.50 (m, 1H, CH₂CHMe in both isomers), 2.35 (m, 2H, CH₂CHMe in both isomers), 2.21 (s, 3H, CH₃ in both isomers), 2.16 (s, 3H, CH₃ in both isomers), 1.70 (m, 2H, CH₂CH₂CHOH in both isomers), 1.06 (d, J=6.57 Hz, 3H, MeCH major isomer), 1.01 (d, J=6.57 Hz, 3H, MeCH minor isomer).

4/7-[2-(1H-Inden-2-yl)ethyl]-2,5,6-trimethyl-1H-indene

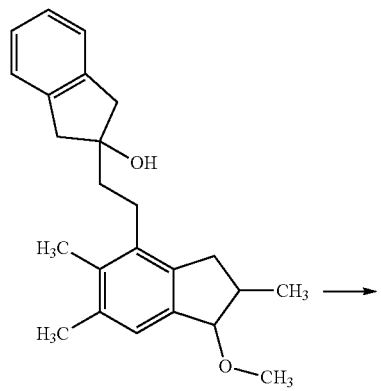

To a hot (110° C.) solution of 6.0 g (18.61 mmol) of 2-[2-(1-methoxy-2,5,6-trimethyl-2,3-dihydro-1H-inden-4-yl)ethyl]indan-2-ol in 130 ml of toluene 0.708 g (3.72 mmol) of TsOH*H₂O was added. This mixture was refluxed with a Dean-Stark trap for 30 min, and then passed through short column with Silica Gel 60 (40-63 um, d 80 mm, l 60 mm). The column was additionally washed with 300 ml of toluene. The combined elute was evaporated to dryness. The product was isolated by flash chromatography using a short column with Silica Gel 60 (40-63 um, d 60 mm, l 70 mm; eluent: hexanes/ether=50/1). Yield 4.58 g (82%).

Anal. calc. for $C_{23}H_{24}$: C, 91.95; H, 8.05. Found: C, 91.93; H, 8.07.

¹H NMR (CDCl₃): δ 7.44 (d, J=7.07 Hz, 1H, 4-H in unsubst. indene), 7.35 (d, J=7.33 Hz, 1H, 7-H in unsubst. indene), 7.28 (t, J=7.33 Hz, 1H, 6-H in unsubst. indene), 7.17 (t, J=7.07 Hz, 1H, 5-H in unsubst. indene), 7.02 (s, 1H, H in 2,5,6-trimethylindene), 6.67 (s, 1H, vinyl), 6.46 (s, 1H, vinyl), 3.43 (s, 2H, CH₂ in indene), 3.27 (s, 2H, CH₂ in indene), 3.03 (m, 2H, CH₂ in CH₂CH₂), 2.71 (m, 2H, CH₂ in CH₂CH₂), 2.35 (s, 3H, Me), 2.30 (s, 3H, Me), 2.17 (s, 3H, Me).

¹³C{¹H} NMR (CDCl₃): δ 150.39, 145.52, 144.62, 143.18, 143.01, 139.69, 135.10, 134.84, 129.38, 127.26, 126.29, 126.22, 123.73, 123.42, 120.00, 119.58, 41.62, 41.16; CH₂ 31.12, 30.69, 21.08, 16.75, 14.81.

Complex 24-Hf

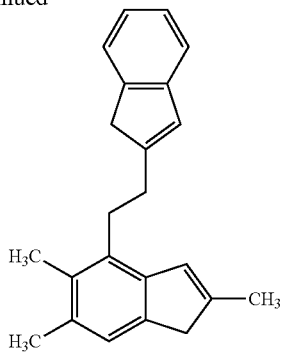

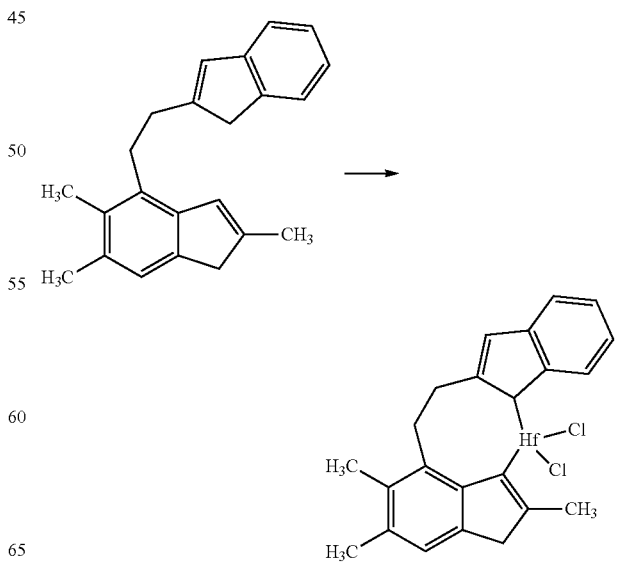

To a solution of 2.14 g (7.12 mmol) of 4/7-[2-(1H-inden-2-yl)ethyl]-2,5,6-trimethyl-1H-indene in 150 ml of ether was added 5.7 ml (14.24 mmol) of 2.5 M n-BuLi in hexanes at −40° C. This mixture was stirred for 24 h at room temperature, then 3.307 g (7.12 mmol) of $HfCl_4(THF)_2$ was added at −30° C. The resulting mixture was stirred for 24 h at room temperature. The solution was concentrated, the residue was dissolved in 125 ml of toluene and refluxed for 12 h. This hot mixture was filtered (G4); the filtrate was evaporated to ca. 1/4 of its starting volume. The formed at −30° C. crystals were filtered off (G3) and dried in vacuum. Yield: 1.68 g (43%) yellow crystals of complex.

Anal. Calcd for: $C_{23}H_{22}Cl_2Hf$: C, 50.43; H, 4.05; Cl, 12.94; Hf, 32.58%. Found: C, 50.45; H, 4.07; Cl, 12.91; Hf, 32.56%.

$^1$H NMR ($CD_2Cl_2$.): δ 7.54-7.52 (m, 1H, unsubstituted indene), 7.25 (s, 1H, trimethylindene), 7.15 (m, 1H, unsubstituted indene), 7.10-7.08 (m, 2H, unsubstituted indene), 6.06 (d, J=2.52 Hz, 1H, vinyl in trimethylindene), 6.03 (d, J=3.28 Hz, 2H, vinyl in unsubstituted indene), 4.41 (d, J=2.52 Hz, 1H, vinyl in trimethylindene), 3.64-3.55 (m, 2H, $CH_2$), 3.52-3.41 (m, 1H, CHH), 3.34-3.27 (m, 1H, CHH), 2.41 (s, 6H, 5-Me and 6-Me), 2.34 (s, 3H, 2-Me).

$^{13}C\{^1H\}$ NMR ($CD_2Cl_2$): δ 139.15, 136.95, 135.16, 132.27, 131.19, 128.96, 128.65, 128.15, 127.64, 125.28, 124.97, 124.90, 124.83, 121.58, 106.63, 101.73, 99.13, 96.83, 27.45, 25.05, 21.56, 16.96, 14.94.

Example 10

4/7-(2-bromoethyl)-2,5,6-trimethyl-1H-indene

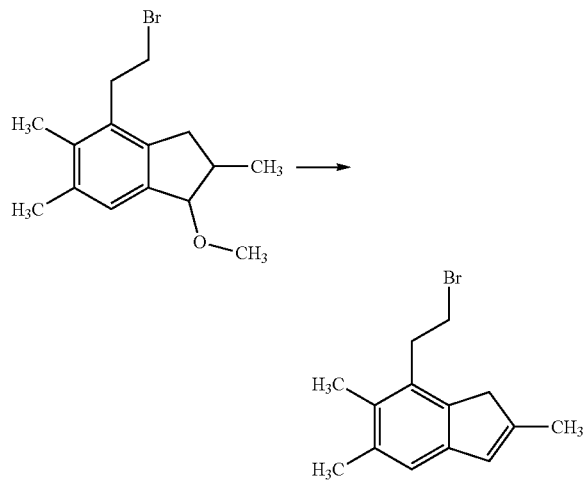

To a hot (110° C.) solution of 6.28 g (21.13 mmol) of 4-(2-bromoethyl)-1-methoxy-2,5,6-trimethylindane in 75 ml of toluene 0.4 g of $TsOH*H_2O$ was added. This mixture was refluxed with Dean-Stark trap for 10 min and then passed through the layer of Silica Gel 60 (40-63 um, d 80 mm, l 50 mm). The Silica Gel layer was additionally washed by 300 ml of toluene. The combined organic extract was evaporated to dryness. The product was isolated by flash chromatography using a short column with Silica Gel 60 (40-63 um, d 80 mm, l 50 mm; eluent: hexanes). Yield 5.38 g (96%) of 4-(2-bromoethyl)-2,5,6-trimethyl-1H-indene.

Anal. calc. for $C_{14}H_{17}Br$: C, 63.41; H, 6.46. Found: C, 63.44; H, 6.48.

$^1$H NMR ($CDCl_3$): δ 7.01 (s, 1H, 7-H in indenyl), 6.42 (s, 1H, vinyl), 3.47 (t, J=8.84 Hz, 2H, $CH_2Br$), 3.28 (t, J=8.84 Hz, 2H, $CH_2CH_2Br$), 3.26 (s, 2H, $CH_2$ in indenyl), 2.31 (s, 3H, Me), 2.24 (s, 3H, Me)), 2.16 (s, 3H, Me)

$^{13}C\{^1H\}$ NMR ($CDCl_3$): δ 144.87, 143.45, 140.33, 135.42, 131.86, 129.63; CH 127.15, 120.45, 41.76, 35.08, 30.48, 21.03, 16.73, 14.94.

4/7-(2-Cyclopenta-2,4-dien-1-ylethyl)-2,5,6-trimethyl-1H-indene

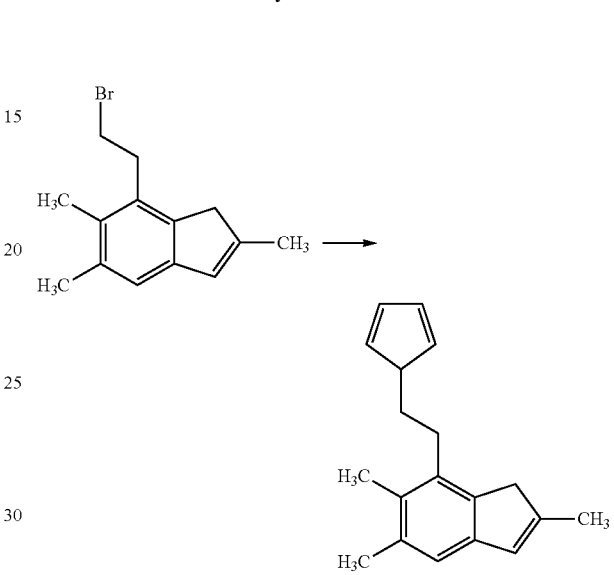

To a solution of 2.68 g (37.11 mmol) of CpLi in 170 ml of ТГФ a solution of 9.84 g (37.11 mmol) of 4/7-(2-bromoethyl)-2,5,6-trimethyl-1H-indene in 10 ml of THF was added dropwise by vigorous stirring for 10 min at −80° C. This mixture was stirred for 60 h at room temperature, and then 1 ml of water was added. The resulting mixture was evaporated to dryness, and 100 ml of water was added to the residue. The crude product was extracted by 3×50 ml of dichloromethane. The combined organic extract was dried over $Na_2SO_4$ and evaporated to dryness. The product was isolated by flash chromatography using a short column with Silica Gel 60 (40-63 um, d 80 mm, l 60 mm; eluent: hexanes. Yield 6.87 g (74%) of a mixture of isomeric compounds.

Anal. calc. for $C_{19}H_{22}$: C, 91.14; H, 8.86. Found: C, 91.17; H, 8.83.

$^1$H NMR ($CDCl_3$): δ 7.04 (m, 1H), 6.59 (m, 1H), 6.53 (m, 1H), 6.45 (m, 1H), 6.33 (m, 1H), 6.15 (m, 1H), 3.50 (m, 2H), 3.29 (s, 2H, $CH_2$), 3.24 (m, 1H), 3.04-2.95 (m, 2H), 3.12 (s, 3H, Me), 2.27 (s, 3H, Me), 2.19 (s, 3H, Me).

Complex 25-Zr

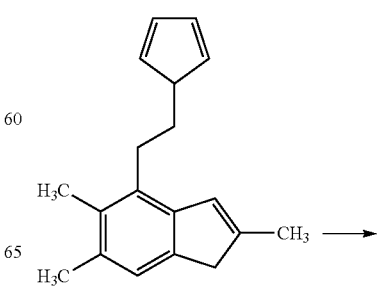

-continued

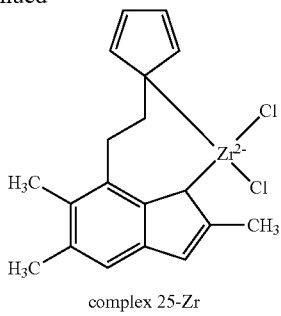

complex 25-Zr

To a solution of 2.50 g (10 mmol) of 4/7-(2-cyclopenta-1,4-dien-1-ylethyl)-2,5,6-trimethyl-1H-indene in 150 ml of ether was added 8 ml (20 mmol) of 2.5 M n-BuLi in hexanes at −40° C. This mixture was stirred for 24 h at room temperature, then 3.77 g (10 mmol) of $ZrCl_4(THF)_2$ was added at −30° C. The resulting mixture was stirred for 24 h at room temperature. The solution was concentrated, the residue was dissolved in 125 ml of toluene and refluxed for 12 h and then filtered through glass frit (G4). The precipitate was additionally washed by 3×50 ml of hot toluene. The combined extract was evaporated to dryness, and the residue was re-crystallized from 30 ml of toluene. Crystals precipitated at −30° C. were collected, washed by 3×3 ml of cold toluene, 2×10 ml of hexanes, and dried in vacuum. Yield 1.03 g (25%).

Anal. calc. for $C_{19}H_{20}Cl_2Zr$: C, 55.59; H, 4.91. Found: C, 55.55; H, 4.94.

$^1$H NMR ($CD_2Cl_2$): δ 7.33 (s, 1H, 7-H in indenyl), 6.50 (m, 1H, 1-H in indenyl), 6.36 (m, 1H, 3-H in indenyl), 6.26 (m, 1H, CH in Cp), 6.21 (m, 1H, CH in Cp), 6.12 (m, 1H, CH in Cp), 4.90 (m, 1H, CH in Cp), 3.43 (m, 1H, $CH_2CHH$), 3.35 (m, 2H, $CH_2CH_2$), 2.79 (m, 1H, $CH_2CHH$), 2.35 (s, 3H, Me), 2.30 (s, 3H, Me), 2.25 (s, 3H, Me).

Polymerisation Reactions:

1. Homogeneous Homopolymerisation to Produce HDPE

Complexes were tested in the solution phase ethylene homopolymerisation.

Polymerisations were carried out in a 0.1 L stainless steel autoclave reactor equipped with a paddle stirrer and a continuous supply of ethylene. Ethylene (>99.95%), nitrogen (>99.999%) and pentane, are further treated with sets of purifiers removing selectively $O_2$, $H_2O$, CO, $CO_2$ and acetylene.

The complex was pre-contacted with MAO for 1 hour with the aluminium to metal ratio 3000 mol/mol. Toluene was used as solvent.

The reactors were made inert with evacuation and nitrogen flushing. The activated complex solution was added to the reactor in an inert nitrogen atmosphere. The polymerisation medium (70 mL Pentane) was added at room temperature. The reactor was heated up to 80° C. and the polymerisation started by introducing the ethylene. Polymerization was continued for 30 minutes at 80° C. and 10 bar ethylene partial pressure. During polymerization, the temperature of the reactor, stirring rate, and reactor pressure were maintained constant. The polymerization was stopped by cutting off the ethylene flow, flushing the reactor with nitrogen and cooling down the reactor to room temperature. The resultant polymer product was separated from the polymerization medium and dried in fume hood over night.

Polymerization results are presented in Table 1.

2. Catalyst Synthesis Method A:

Complexes were supported on Grace XPO-2485A 20 um silica, PV=1.4 mL/g SiO2 with the following procedure.

2.6 mL of MAO (30 w-%) was mixed with 0.06 mmol of complex (Al/M ratio 200) and 0.18 mL of extra toluene was added on top and stirred 30 min at +25° C. The solution was added to 2.0 g of XPO-2485A during 10-15 min and kept 1 h at +25° C. with occasional stirring. The solvent was evaporated off under Ar or N2 flow at +25° C. to give powder.

3. Heterogeneous Homopolymerisation to Produce HDPE

Complexes were supported on Grace XPO-2485A 20 um silica, PV=1.4 mL/g SiO2 with the following procedure.

2.6 mL of MAO (30 w-%) was mixed with 0.06 mmol of complex (Al/M ratio 200) and 0.18 mL of extra toluene was added on top and stirred 30 min at +25° C. The solution was added to 2.0 g of XPO-2485A during 10-15 min and kept 1 h at +25° C. with occasional stirring. The solvent was evaporated off under Ar or N2 flow at +25° C. to give powder.

Polymerisations were carried out in a 0.1 L stainless steel autoclave reactor equipped with a paddle stirrer and a continuous supply of ethylene. Ethylene (>99.95%), nitrogen (>99.999%) and isobutane (>97%), are further treated with sets of purifiers removing selectively $O_2$, $H_2O$, CO, $CO_2$ and acetylene.

Prior to the polymerisation the catalyst was weighted to a catalyst feeding vessel in an inert nitrogen atmosphere.

The reactors were made inert with evacuation and nitrogen flushing. A scavenger was dissolved in a part of the polymerisation medium and precontacted for 5 minutes with the reactor vessel prior to polymerisation. 0.5 mmol of TiBA per 1 mL of polymerisation medium was used. The rest of the polymerisation medium was used to feed the catalyst. In total 70 ml of isobutene or propane was used as the polymerisation medium. The reactor was heated up to 80° C. and the polymerisation started by introducing the ethylene. The reactor pressure was adjusted to the targeted value using the ethylene partial pressure of 5-10 bars. Polymerization was continued for one hour at 80° C. During polymerization, the temperature of the reactor, stirring rate, and reactor pressure were maintained constant.

The polymerization was stopped by cutting off the ethylene flow and degassing the reactor. After the pressure was completely released and medium evaporated the reactor was opened. Resultant polymer product was dried in fume hood over night.

Polymerization results are presented in Table 2.

4. Heterogeneous Copolymerisation to Produce LLDPE

Further heterogeneous polymerisations were carried out in the presence of the comonomer hexene (1.6 ml) to form an LLDPE. The activity of catalysts during polymerisation was measured and are reported in Table 3.

For comparative purposes, the metallocenes $nBuCp_2ZrCl_2$ or $nBuCp_2HBz_2$ were tested under the same conditions for each polymerisation protocol.

As can be seen, the Mw of the polymer formed by the catalysts of the invention is much higher than those formed under identical conditions by the prior art metallocenes. The 1-hexene content measured by FT-IR is higher for many complexes of the invention. Also activity for many of the complexes of the invention is comparable to that of the prior art catalysts.

TABLE 1

RESULTS: HOMOGENEOUS HOMO-POLYMERISATION

| complex | isomeric ratio [meso-like/rac-like] | activity [kgpol/gMe * h] | Mw [g/mol] | Mw/Mn |
|---|---|---|---|---|
| (n-BuCp)ZrCl$_2$ |  | 4829 | 282000 | 2.2 |
| 16-Zr | 2:1 | 1863 | 836000 | 2.0 |
| 8-Zr | 8:1 | 1076 | 750000 | 2.1 |
| 1-Zr | single | 86 | 260000 | 2.3 |
| 17-Zr | single | 763 | 835000 | 4.1 |
| 15-Zr | 3:2 | 1048 | 831000 | 2.4 |
| 13-Zr | single | 316 | 804000 | 2.3 |
| 9-Zr | 7:1 | 657 | 992000 | 2.0 |
| 7-Zr | single | 305 | 477000 | 2.2 |
| 10-Zr | 6:1 | 805 | 965000 | 1.9 |
| 11-Zr | single | 475 | 618000 | 2.3 |
| 4-Zr | 1:1 | 424 | 535000 | 2.3 |
| 5-Zr | 4:1 | 356 | 485000 | 2.0 |

TABLE 2

RESULTS: HETEROGENEOUS HOMO-POLYMERISATION

| complex | isomeric ratio [meso-like/rac-like] | medium | activity [kgpol/(gcat * h)] | Mw [g/mol] | Mw/Mn |
|---|---|---|---|---|---|
| (n-BuCp)ZrCl$_2$ |  | propane | 1.16 | 166000 | 2.4 |
| (n-BuCp)HfBz$_2$ |  | propane | 1.74 | 108000 | 2.2 |
| 16-Zr | 2:1 | iso-butane | 0.22 | 743000 | 2.8 |
| 8-Zr | 8:1 | iso-butane | 0.21 | 568000 | 2.7 |
| 1-Zr | single | iso-butane | 0.17 | 223000 | 3.4 |
| 17-Zr | single | iso-butane | 0.07 | 647000 | 3.4 |
| 15-Zr | 3:2 | iso-butane | 0.26 | 985000 | 4.0 |
| 13-Zr | single | iso-butane | 0.18 | 1054000 | 3.4 |
| 9-Zr | 7:1 | iso-butane | 0.35 | 862000 | 3.8 |
| 7-Zr | single | iso-butane | 0.24 | 545000 | 3.3 |
| 10-Zr | 6:1 | iso-butane | 0.31 | 991000 | 4.8 |
| 11-Zr | single | iso-butane | 0.18 | 730000 | 3.2 |
| 4-Zr | 1:1 | iso-butane | 0.24 | 434000 | 3.2 |
| 5-Zr | 4:1 | iso-butane | 0.26 | 528000 | 2.7 |
| 18-Zr | single | Propane | 0.76 | 166000 | 3.7 |
| 14-Zr | single | Propane | 0.38 | 598000 | 2.6 |
| 14-Hf | single | Propane | 0.08 | 961000 | 2.8 |
| 3-Zr | single | Propane | 0.10 | 844000 | 3.2 |
| 3-Hf | single | Propane | 0.02 | 748000 | 4.1 |
| 7-Hf | single | Propane | 0.03 | 765000 | 3.2 |
| 9-Hf | single | Propane | 0.02 | 498000 | 3.3 |
| 19-Zr | single | Propane | 0.40 | 251000 | 2.9 |
| 19-Hf | single | Propane | 0.48 | 609000 | 2.6 |
| 20-Zr | 4:1 | Propane | 0.82 | 126000 | 2.9 |
| 20-Hf | 2:1 | Propane | 0.06 | 272000 | 2.8 |
| 12-Zr | 3:1 | Propane | 0.30 | 1193000 | 2.4 |
| 12-Hf | single | Propane | 0.02 | 1189000 | 2.7 |
| 11-Hf | single | Propane | 0.03 | 533000 | 4.9 |
| 10-Hf | single | Propane | 0.04 | 586000 | 2.7 |
| 18-Hf | single | Propane | 0.05 | 417000 | 3.8 |

TABLE 3

RESULTS: HETEROGENEOUS CO-POLYMERISATION

| complex | isomeric ratio [meso-like/rac-like] | medium | ethylene partial pressure [bar] | TiBA [mmol/L] | activity [kgpol/(gcat * h)] | Mw [g/mol] | Mw/Mn | hexene content [%] |
|---|---|---|---|---|---|---|---|---|
| (n-BuCp)ZrCl$_2$ |  | propane | 10 | 0.5 | 0.7 | 518000 | 2.6 | 3.5 |
| (n-BuCp)HfBz$_2$ |  | propane | 10 | 0.5 | 0.8 | 290000 | 2.5 | 2.8 |
| 16-Zr | 2:1 | iso-butane | 5 | no | 0.30 | 484000 | 2.6 | 5.3 |
| 8-Zr | 8:1 | iso-butane | 5 | no | 0.15 | 461000 | 4.4 | 1.1 |
| 1-Zr | single | iso-butane | 5 | no | 0.13 | 254000 | 4.3 | 4.8 |
| 15-Zr * | 3:2 | iso-butane | 5 | 0.5 | 0.33 | 405000 | 5.1 | 4.5 |
| 13-Zr | single | iso-butane | 5 | no | 0.10 | 746000 | 2.2 | 6.4 |
| 9-Zr | 7:1 | iso-butane | 5 | no | 0.16 | 483000 | 2.9 | 7.6 |
| 10-Zr * | 6:1 | iso-butane | 5 | 0.5 | 0.32 | 544000 | 2.1 | 8.0 |
| 18-Zr | single | propane | 10 | 0.5 | 1.05 | 140000 | 3.1 | 3.9 |
| 14-Zr | single | propane | 10 | 0.5 | 0.92 | 415000 | 2.4 | 3.9 |
| 14-Hf | single | propane | 10 | 0.5 | 0.05 | 676000 | 3.1 | 6.6 |
| 3-Zr | single | propane | 10 | 0.5 | 0.23 | 655000 | 2.4 | 7.3 |
| 3-Hf | single | propane | 10 | 0.5 | 0.01 | 373000 | 4.4 | 10.6 |
| 7-Hf | single | propane | 10 | 0.5 | 0.04 | 395000 | 4.2 | 10.6 |
| 9-Hf | single | propane | 10 | 0.5 | 0.02 | 254000 | 3.8 | 15.9 |
| 19-Zr | single | propane | 10 | 0.5 | 0.62 | 271000 | 2.4 | 2.2 |
| 19-Hf | single | propane | 10 | 0.5 | 0.50 | 521000 | 2.4 | 3.2 |
| 20-Zr | 4:1 | propane | 10 | 0.5 | 0.90 | 146000 | 2.7 | 4.8 |
| 20-Hf | 2:1 | propane | 10 | 0.5 | 0.07 | 279000 | 2.5 | 6.5 |
| 12-Zr | 3:1 | propane | 10 | 0.5 | 0.27 | 928000 | 2.4 | 1.1 |
| 12-Hf | single | propane | 10 | 0.5 | 0.03 | 797000 | 3.2 | 2.1 |
| 11-Hf | single | propane | 10 | 0.5 | 0.02 | 294000 | 6.7 | 9.0 |
| 10-Hf | single | propane | 10 | 0.5 | 0.04 | 298000 | 2.7 | 19.3 |
| 18-Hf | single | propane | 10 | 0.5 | 0.06 | 283000 | 2.9 | 6.6 |

5. Catalyst Synthesis Method B:

Complex dimethylsilyl-(2-methyl-6-tert-butyl-inden-4-yl)-cyclopentadienyl zirconium dichloride was supported on Grace XPO-2485A 20 μm silica, PV=1.4 mL/g $SiO^2$ by the following procedure:

1. First, 0.061 mmol of complex was dissolved in a solution containing 1.3 mL of MAO (30 w-%) and 2.9 mL of toluene to form a mixture with Al/M ratio 100. The resulting mixture was stirred for 30 min at +25° C. with vortex mixing of 500 rpm.
2. This solution was added during 10-15 min into 1.0 g of silica (XPO-2485A). During addition, vortex mixing was 800 rpm. Then, the system was kept at 3 h at +25° C. with vortex mixing of 500 rpm.
3. Finally, the solvent was evaporated off under N2 flow at +50° C. to give catalyst powder. Drying phase lasted 3 h at 300 rpm vortex mixing.

6. Catalyst Synthesis Method C:

Complex dimethylsilyl-(2-methyl-6-tert-butyl-inden-4-yl)-cyclopentadienyl zirconium dichloride was supported on Grace XPO-2485A 20 μm silica, PV=1.4 mL/g SiO2 with the following procedure.

1. 1.3 mL of MAO (30 w-%) was contacted with 2.35 mL of toluene for 30 min and then added dropwise on silica. Efficient mixing was achieved by vortex mixing with 800 rpm.
2. The resultant reaction mixture was heated up to 80° C. and reaction was continued for 90 min.
3. Reaction mixture was cooled down to room temperature and 0.061 mmol complex (dimethylsilyl-(2-methyl-6-tert-butyl-inden-4-yl)-cyclopentadienyl zirconium dichloride) dissolved in 0.6 mL of toluene was added onto MAO treated silica to give a catalyst of Al/Zr ratio 100. After addition of complex, the resultant solution was kept for 60 min at room temperature with 500 rpm vortex mixing.
4. Finally, formed catalyst was dried under N2 flow at +50° C. Drying phase lasted 3 h at 300 rpm vortex mixing.

7. Heterogeneous Polymerisation Conditions

Polymerisations were carried out in a Büchi 2 L stainless steel autoclave reactor equipped with a paddle stirrer and a continuous supply of ethylene. Ethylene (>99.95%), nitrogen (>99.999%) and isobutane (>97%), 1-hexene (>99%) are further treated with sets of purifiers removing selectively $O_2$, $H_2O$, CO, $CO_2$ and acetylene.

First, the reactor was inertized with evacuation and nitrogen flushing. Next, the polymerization medium (1.2 L isobutane) was added to the reactor. Catalyst was weighed and catalyst feeder was closed tightly in a glove box. An appropriate amount of the catalyst (approximately 100 mg) prepared was charged to a feeding vessel in glove box and the catalyst injected to the stirred reactor under N2 pressure. The reactor was then heated to +80° C. after which the polymerisation was started by adding 25 mL of 1-hexene with continuous feed of ethylene. The reactor pressure was adjusted to the targeted value using the ethylene partial pressure 8 bars. Polymerization was continued for one hour at 80° C. During polymerization, the temperature of the reactor, stirring rate, and reactor pressure were maintained constant. The ethylene consumption and the reactor temperature were recorded.

The polymerization was stopped by cutting off the ethylene flow and degassing the reactor. After the pressure was completely released and medium evaporated (approx 30 minutes) the reactor was opened. Resultant polymer product was dried in fume hood over night.

Polymerization results are presented in Table 4.

For comparative purposes, a reference catalyst containing metallocenes complex (n-BuCp)$_2$HfBz$_2$ was synthesized and tested under the same conditions. In reference catalyst synthesis, only complex amount was changed to (0.077 mmol) give Al:M ratio of 150. In polymerization, about 200 mg of catalyst was used in reference polymerization.

As can be seen from Table 4, the Mw of the polymer formed by this catalyst of the invention is much higher and comonomer content equal compared to that formed under identical conditions by the prior art metallocenes. Catalyst activity is further increased with catalyst synthesis method C. Table 4 also shows measured Al/M ratio based on inductive coupling plasma (ICP) measurement.

ICP analysis: The elemental analysis of a catalyst was performed by taking a solid sample of mass, M, cooling over dry ice. Samples were diluted up to a known volume, V, by dissolving in nitric acid ($HNO_3$, 65%, 5% of V) and freshly deionised (DI) water (5% of V). The solution was then added to hydrofluoric acid (HF, 40%, 3% of V), diluted with DI water up to the final volume, V, and left to stabilise for two hours.

The analysis was run at room temperature using a Thermo Elemental IRIS Advantage XUV Inductively Coupled Plasma—Atomic Excitation Spectrometer (ICP-AES) which was calibrated immediately before analysis using a blank (a solution of 5% $HNO_3$, 3% HF in DI water), a low standard (10 ppm Al in a solution of 5% $HNO_3$, 3% HF in DI water), a high standard (50 ppm Al, 50 ppm Hf, 20 ppm Zr in a solution of 5% $HNO_3$, 3% HF in DI water) and a quality control sample (20 ppm Al, 20 ppm Hf, 10 ppm Zr in a solution of 5% $HNO_3$, 3% HF in DI water).

The content of hafnium was monitored using the 282.022 nm and 339.980 nm lines and the content for zirconium using 339.198 nm line. The content of aluminium was monitored via the 167.081 nm line, when Al concentration in ICP sample was between 0-10 ppm and via the 396.152 nm line for Al concentrations between 10-100 ppm.

The reported values, required to be between 0 and 100, or further dilution is required, are an average of three successive aliquots taken from the same sample and are related back to the original catalyst using equation 1.

$$C = \frac{R \times V}{M} \qquad \text{Equation 1}$$

Where:

C is the concentration in ppm, related to % content by a factor of 10,000

R is the reported value from the ICP-AES

V is the total volume of dilution in ml

M is the original mass of sample in g

If dilution was required then this also needs to be taken into account by multiplication of C by the dilution factor.

TABLE 4

| COMPLEX | Catalyst preparation (B or C) | Al:M (mol:mol) | Polymerization Yield (g) | Activity (kgPE/ gcat · h) | BD (kg/m$^3$) | MFR21 (g/10 min) | Mw (g/mol) | Mn (g/mol) | Mw/Mn | 1-Hexene (wt-%) |
|---|---|---|---|---|---|---|---|---|---|---|
| SiMe$_2$(2-Me-6-t-Bu-Ind)CpZrCl$_2$ | B | 100 | 38.6 | 0.38 | — | 0.06 | 447 000 | 136 300 | 3.3 | 2.8 |
|  | C | 110 | 91.8 | 0.92 | 395 | 0.03 | 536 000 | 172 400 | 3.1 | 2.7 |
| REF (n-BuCp)$_2$HfBz$_2$ | B | 150 | 251.1 | 1.25 | 444 | 2.12 | 213 000 | 94 900 | 2.2 | 2.7 |
|  | C | 160 | 155.7 | 1.42 | 430 | 2.57 | 217 000 | 89 500 | 2.4 | 2.9 |

The invention claimed is:

1. A complex comprising a ligand of formula (I):

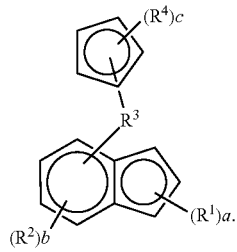

wherein
each $R^1$, which may be the same or different, is hydrogen, an optionally substituted $C_{1-20}$ hydrocarbyl group, $N(R^5)_2$, silyl, siloxy; an optionally substituted heteroaryl group, an optionally substituted heterocyclyl group or two $R^1$ groups on adjacent carbon atoms taken together to form an optionally substituted 5- to 8-membered fused ring;

each $R^2$, which may be the same or different is hydrogen, is hydrogen, an optionally substituted $C_{1-20}$ hydrocarbyl group, $N(R^5)_2$, silyl, siloxy; an optionally substituted heteroaryl group, or an optionally substituted heterocyclyl group;

$R^3$, which binds the 5-membered ring of the top ligand and to the 6-membered ring of the indenyl group, is —(Si$(R^5)_2)_p$—, where p is 1 or 2, —(C($R_5)_2)_n$— where n is an integer of 2 or more;

each $R^4$ which are the same or different, is hydrogen, an optionally substituted $C_{1-20}$ hydrocarbyl group, $N(R^5)_2$, silyl, siloxy, an optionally substituted heteroaryl group, an optionally substituted heterocyclyl group or two $R^4$ groups on adjacent carbon atoms taken together form an optionally substituted 5- to 8-membered fused carbon ring;

each $R^5$, which are the same or different, is hydrogen, an optionally substituted $C_{1-20}$ hydrocarbyl group, or two $R^5$ groups taken together form an optionally substituted 5- to 8-membered ring;

a is 0 to 3;

b is 0 to 3 c is 0 to 4;

complexed to a metal ion, M.

2. A complex as claimed in claim 1 wherein M is a group 4 to 6 metal ion.

3. A complex as claimed in claim 1 wherein M is Zr or Hf.

4. A complex as claimed in claim 1 comprising a ligand of formula (V)

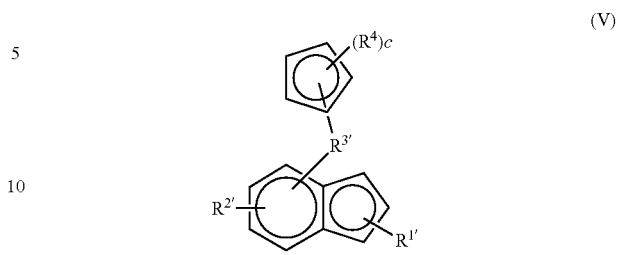

wherein $R^4$ and c are as hereinbefore defined, $R^{1'}$ is hydrogen or $C_{1-6}$-alkyl, $R^{2'}$ is hydrogen or $C_{1-6}$—alkyl and $R^{3'}$ is $SiMe_2$ or $CH_2CH_2$.

5. A complex as claimed in claim 1 wherein $R^4$ is methyl, tert butyl, two $R^4$ groups taken together form an indenyl ring or 4 $R^4$ groups taken together form a fluorenyl ring.

6. A complex as claimed in claim 1 wherein one $R^4$ group represents a $C_{1-6}$ alkyl and two other $R^4$ groups are taken together to form an optionally substituted 6-membered fused carbon ring.

7. A complex claimed in claim 1 which has a substituent in 5-position of the indenyl ligand.

8. A complex claimed in claim 1 which has a substituent in 2-position of the indenyl ligand.

9. A complex claimed in claim 1 which has a tert-butyl substituent in 5-position of the indenyl ligand.

10. A complex claimed in claim 1 which has a methyl substituent in 2-position of indenyl ligand.

11. A complex claimed in claim 1 which has the following structure

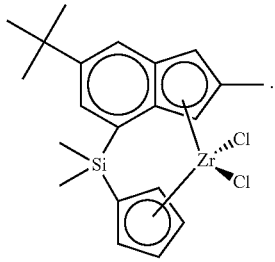

12. An olefin polymerisation catalyst comprising:
(i) a complex comprising a metal ion coordinated by at least one ligand of claim 11; and
(ii) a cocatalyst.

13. A supported catalyst which contains a complex as claimed in claim 1.

14. A supported catalyst as claimed in claim 13 in which the support is contacted in the first stage with cocatalyst and then in the second stage the complex is added into cocatalyst treated carrier.

15. A process for the polymerisation of at least one olefin comprising polymerizing said at least one olefin in the presence of the catalyst of claim 14.

* * * * *